US007653556B2

(12) United States Patent
Rovinelli et al.

(10) Patent No.: US 7,653,556 B2
(45) Date of Patent: Jan. 26, 2010

(54) COMPUTER ARCHITECTURE AND PROCESS OF PATIENT GENERATION, EVOLUTION, AND SIMULATION FOR COMPUTER BASED TESTING SYSTEM

(75) Inventors: Richard J. Rovinelli, Lexington, KY (US); Walton Sumner, II, St. Louis, MO (US); Victor W. Marek, Lexington, KY (US); Miroslav Truszczynski, Lexington, KY (US)

(73) Assignee: American Board of Family Medicine, Inc., Lexington, KY (US)

( * ) Notice: Subject to any disclaimer, the term of this patent is extended or adjusted under 35 U.S.C. 154(b) by 0 days.

(21) Appl. No.: 11/220,638

(22) Filed: Sep. 8, 2005

(65) Prior Publication Data

US 2006/0004608 A1 Jan. 5, 2006

Related U.S. Application Data

(60) Division of application No. 09/759,205, filed on Jan. 16, 2001, now Pat. No. 6,978,244, which is a continuation of application No. 08/961,185, filed on Oct. 30, 1997, now Pat. No. 6,246,975.

(60) Provisional application No. 60/029,856, filed on Oct. 30, 1996.

(51) Int. Cl.
*G06Q 10/00* (2006.01)
(52) U.S. Cl. .................. 705/2; 705/3; 600/300; 434/262
(58) Field of Classification Search ............ 705/2, 705/3; 600/300
See application file for complete search history.

(56) References Cited

U.S. PATENT DOCUMENTS

| 3,000,800 A | 11/1961 | Morchand |
| 3,484,950 A | 12/1969 | Serrell et al. |
| 3,537,190 A | 11/1970 | Serrell et al. |
| 4,360,345 A | 11/1982 | Hon |
| 4,547,161 A | 10/1985 | Manning |

(Continued)

FOREIGN PATENT DOCUMENTS

EP 367709 5/1990

OTHER PUBLICATIONS

Goldman, B., "Robert Still is my favorite patient (and software)," Computers Informatique, 1990, Can Med Assoc J, 244-246.*

(Continued)

*Primary Examiner*—Gerald J. O'Connor
*Assistant Examiner*—Lena Najarian
(74) *Attorney, Agent, or Firm*—Irah H. Donner; Wilmer Cutler Pickering Hale and Dorr LLP

(57) ABSTRACT

A computer implemented simulation and evaluation method simulates interventions to a patient by a user, and evaluates the interventions responsive to predetermined criteria and the interventions. The method includes defining a test area to evaluate the user to at least one of predetermined criteria and a user profile, selecting genetic information of the patient responsive to the test area, and generating a patient history responsive to the test area and the genetic information. The method also includes receiving at least one intervention input by the user, and evaluating the user responsive to the intervention and predetermined criteria.

65 Claims, 17 Drawing Sheets

U.S. PATENT DOCUMENTS

| | | | |
|---|---|---|---|
| 4,797,104 A | 1/1989 | Laerdal et al. | |
| 4,978,305 A | 12/1990 | Kraft | |
| 5,002,491 A | 3/1991 | Abrahamson et al. | |
| 5,006,987 A | 4/1991 | Harless | |
| 5,011,413 A | 4/1991 | Ferris et al. | |
| 5,033,969 A | 7/1991 | Kamimura et al. | |
| 5,059,127 A | 10/1991 | Lewis et al. | |
| 5,103,408 A | 4/1992 | Greenberg et al. | |
| 5,141,439 A | 8/1992 | Cousins | |
| 5,163,131 A | 11/1992 | Row et al. | |
| 5,180,309 A | 1/1993 | Egnor | |
| 5,195,033 A | 3/1993 | Samph et al. | |
| 5,204,813 A | 4/1993 | Samph et al. | |
| 5,211,564 A | 5/1993 | Martinez et al. | |
| 5,219,291 A | 6/1993 | Fong et al. | |
| 5,240,419 A | 8/1993 | deGyarfas | |
| 5,341,292 A * | 8/1994 | Zamenhof | 600/425 |
| 5,385,474 A * | 1/1995 | Brindle | 434/267 |
| 5,596,653 A * | 1/1997 | Kurokawa | 382/128 |
| 5,657,255 A | 8/1997 | Fink et al. | |
| 5,704,791 A * | 1/1998 | Gillio | 434/262 |
| 5,711,297 A * | 1/1998 | Iliff | 600/300 |
| 5,769,074 A * | 6/1998 | Barnhill et al. | 600/300 |
| 5,791,907 A * | 8/1998 | Ramshaw et al. | 434/262 |
| 5,800,178 A * | 9/1998 | Gillio | 434/262 |
| 5,845,255 A * | 12/1998 | Mayaud | 705/3 |
| 5,853,292 A * | 12/1998 | Eggert et al. | 434/262 |
| 5,882,206 A * | 3/1999 | Gillio | 434/262 |
| 5,931,160 A * | 8/1999 | Gilmore et al. | 128/204.21 |
| 6,076,083 A * | 6/2000 | Baker | 706/52 |
| 6,108,635 A | 8/2000 | Herren et al. | |
| 6,186,145 B1* | 2/2001 | Brown | 128/897 |
| 6,248,063 B1* | 6/2001 | Barnhill et al. | 600/300 |
| 6,692,258 B1 | 2/2004 | Kurzweil et al. | |
| 6,978,244 B2 | 12/2005 | Rovinelli et al. | |
| 2002/0033802 A1* | 3/2002 | Rosenberg | 345/156 |

OTHER PUBLICATIONS

Eliot, C. and Woolf, B. P., "Iterative Development and Validation of a Simulation-Based Medical Tutor," Department of Computer Science, University of Massachusetts, Lecture Notes in Computer Science, 1996, Springer Berlin.*

Altman, Russ B. et al. "A Programming Course in Bioinformatics for Computer and Information Science Students," Knowledge Systems Laboratory Report KSL-95-64 (1995).

Anjewierden, Anjo et al. "Shelley—Computer-Aided Knowledge Engineering," Knowledge Acquisition (1992), pp. 109-125

Ash, David et al. "Action-Based Fault Hierarchies for Real-Time Responses," Knowledge Systems Laboratory Report KSL 92-05 (1992).

Balla, J. I. et al. "Obstacles to Acceptance of Clinical Decision Analysis" BJM, vol. 298, Mar. 4, 1989.

Barnett, G. O. "The Use of a Computer-based System to Teach Clinical Problem-solving," Computers in Biomedical Research, Academic Press, New York 1974. vol. 4, pp. 301-319.

Barnett, G. O. et al. "Computers in Medical Evaluation: Present and Future," Proceedings of the Seventh Annual Symposium on Computer Applications in Medical Care, IEEE Press, Washington, DC 1983, pp. 11-13.

Barroso, L.A. et al. "RPM: A Rapid Prototyping Engine for Multiprocessor Systems." IEEE Computer, Feb. 1995, pp. 26-34.

Baud, Robert H. et al. "Knowledge Sources for Natural Language Processing," 1996 AMIA, Inc., pp. 70-74.

Becker, W. J. "Canadian Specialty Examinations: Considerations for the Future," Annals RCPSC, vol. 27, No. 7, Oct. 1994.

Bergeron, B. M.D. "Iliad: A Diagnostic Consultant and Patient Simulator," Computing, vol. 8, 1991. pp. 46-53.

Berman, Lewis et al. "Automated Integration of External Databases: A Knowledge-Based Approach to Enhancing Rule-Based Expert Systems," Computers and Biomedical Research 26, (1993), pp. 230-241.

Bhandsali, Sanjay et al. "Synthesis of UNIX Programs using Derivational Analogy," Knowledge Systems Laboratory Report KSL-92-02 (1992).

Bishop et al. "The Unified Medical Language System (UMLS)," Computing, vol. 9, No. 4, 1992.

Bishop, Charles W. "Alternate Approaches to a UMLS," Medical Decision Making, vol. 11, No. 4, Oct.-Dec. 1991 Supplement.

Bishop, Charles W. et al. "Representing Medical Knowledge: Reconciling the Present or Creating the Future?," M.D. Computing, vol. 9, No. 4, 1992.

Board of Directors of the American Medical Informatics Association. "Standards for Medical Identifiers, Codes, and Messages Needed to Create an Efficient Computer-stored Medical Record," Journal of the American Medical Informatics Association, vol. 1, No. 1, Jan./Feb. 1994, pp. 1-7.

Board of Directors of the American Medical Informatics Association. "Standards for Medical Identifiers, Codes, and Messages Needed to Create an Efficient Computer-stored Medical Record," Journal of the American Medical Informatics Assocociation, vol. 1, No. 1, Jan./Feb. 1994.

Born, Andreas et al. "A Blackboard-Approach to a Knowledge Based Tutoring System for Linear Programming," nstitute fur Informatik/ WWZ, Switzerland.

Boxer, A. "Where Buses Cannot Go," IEEE Spectrum, Feb. 1995. pp. 41-45.

Bradshaw, J. M. et al. "Knowledge Acquisition Techniques for Decision Analysis Using AOTL and Aquinas," Knowledge Acquisition (1991) 3, pp. 49-77.

Breuker, J. et al. "Models of Expertise in Knowledge Acquisition, In: Gida and Tasso(eds, Topics in Expert System Design: Methodologies and Tools," North Holland Publishing, 1989.

Buekens, F. et al. "The Explanatory Role of Events in Causal and Temporal Reasoning in Medicine," Methods of Information in Medicine 1993; 32: 274-278.

Campbell, James R. et al. "Phase II Evaluation of Clinical Coding Schemes: Completeness, Taxonomy, Mapping, Definitions and Clarity," Dept. of Internal Medicine, Univ. of Nebraska.

Campbell, Keith E. et al. "Creation of a Systematic Domain for Medical Care: The Need for a Comprehensive Patient-Description Vocabulary," Knowledge Systems Laboratory Report KSL-91-60 (1991).

Campbell, M. D. et al. "Galapagos: Computer-Based Support for Evolution of a Convergent Medical Terminology," 1996 AMIA Inc., pp. 269-273.

Cason, Gerald J. "Test Results Depend on Response Format," Office of Educational Development, Univ. of Arkansas for Medical Sciences, vol. 6, No. 8, Dec. 1980.

Cawley, M. G. et al. "Data Representation for Subsequent Image Interpretation," Med. Inform. (1991), vol. 16, No. 2, pp. 125-136.

Chandrasekaran, B. "Generic Tasks in Knowledge-Based Reasoning: High-Level Building Blocks for Expert System Design," Ohio State University, IEEE, Fall 1986.

Charniak, Eugene. "Bayesian Networks without Tears," AI Magazine, 1991, pp. 50-63.

Christensen, Caryn et al. "Framing Bias Among Expert and Novice Physicians," Academic Medicine, vol. 66, No. 9, Sep. Supplement 1991.

Chung, Jaesam. "An Advance toward Instructional Management: Prescriptive Knowledge Base of Learner Control," Indiana University, pp. 1-9.

Cimino, J. J. "Review Paper: Coding Systems in Health Care," Methods of Information in Medicine 1996; 35: pp. 273-284.

Cimino, James J. et al. "Knowledge-based Approaches to the Maintenance of a Large Controlled Medical Terminology," Journal of the American Medical Informatics Association, vol. 1, No. 1, Jan./Feb. 1994, pp. 35-50.

Clauser, Brian et al. "Scoring a Performance-Based Assessment Modeling the Judgments of Experts," Journal of Educational Measurement, Winter 1995, vol. 32, No. 4, pp. 397-415.

Clyman, Stephen G. et al. "Status Report on the NBME's Computer-Based Testing," Academic Medicine, vol. 65, 1990. pp. 235-241.
Combs, David M. et al. "From Expert Models to Expert Systems: Translation of an Intermediate Knowledge Representation," Knowledge Systems Laboratory Report KSL-88-58, (1988).
Computer Organization and Architecture, Stallings, William. MacMilliam Publishing Co. 3.sup.rd ed. 1993.
Concato et al., Monte Carlo Methods in Clinical Research: Applications in Multivariable Analysis, Aug. 1997, Journal of InvestigativeMedicine, vol. 45 No. 6, pp. 394-400.
Cook, John. "Coleridge: Composition Learning Environment for Reflection about Intentions and Dialogue Goals in Education," School of Technology and Information Studies, Thames Valley University, Ealing, London.
Cooper, Gregory F. "A Diagnostic Method that Uses Causal Knowledge and Linear Programming in the Application of Bayes' Formula," Computer Methods and Programs in Biomedicine, vol. 22, (1986) 223-237.
Culhane, Charles. "Streamlining for Managed Care," American Medical Newsletter.
Data Communications Principles, Gitlin, R.D., J.F. Hayes and S.B. Weinstain. Plenum Press, 1992.
Data Network Design, Spohn, Darren L. McGraw-Hill, Inc. 1993.
David, J. K. et al. "Second Generation Expert Systems: A Step Forward in Knowledge Engineering," Second Generation Expert Systems. Springer Verlag, New York, NY, 1993. pp. 3-23.
Davis, R. "Expert Systems: Where are We and Where Do We Go From Here," A1 Magazine, vol. 3, 1983. pp. 3-22.
Dawes, Ron M. et al. "Clinical Versus Actuarial Judgment," Science, Mar. 31, 1989, vol. 243, pp. 1668-1674.
Day, Susan C. et al. "The Validity of an Essay Test of Clinical Judgment," Academic Medicine, vol. 65, No. 9, Sep. Supplement 1990.
Diamond, George A. et al. "Analysis of Probability as an Aid in the clinical Diagnosis of Coronary-Artery Disease," The New England Journal of Medicine, vol. 300, No. 24, Jun. 14, 1979.
Dolan, James G. et al. "The Analytic Hierarchy Process in Medical Decision Making: A Tutorial," Medical Decision Making, vol. 9, No. 1, Jan.-Mar. 1989.
Doughty, Ken. "Auditing the Disaster Recovery Plan," EDPACS, Sep. 1993, vol. XXI, No. 3.
Egar, John W. et al. "Graph-Grammar Productions for the Modeling of Medical Dilemmas," Knowledge Systems Laboratory Report KSL-92-15, (1992).
Elstein, Arther S. et al. "Medical Problem Solving," Evaluation & The Health Professions, vol. 13, No. 1, Mar. 1990.
Elstein, Arthur S. "Beyond Multiple-choice Questions and Essays: The Need for a New Way to Assess Clinical Competence," Academic Medicine, vol. 68, No. 4, Apr. 1993.
Ericsson, Ka A. "Protocol Analysis: Verbal Reports as Data," Simon HA. MIT Press. Cambridge, MA 1984.
Eriksson, Henri et al. "Conceptual Models for Automatic Generation of Knowledge-Acquisition Tools," Knowledge Systems Laboratory Report KSL-92-28 (1993).
Eriksson, Henrik et al. "Generation of Knowledge-Acquisition Tools from Domain Ontologies," Knowledge Systems Laboratory Report KSL-93-56, (1994).
Eriksson, Henrik et al. "Task Modeling with Reusable Problem-Solving Methods," Knowledge Systems Laboratory Report KSL-92-43 (1993).
Eriksson, Henrik. "Metatool Support for Custom-tailored, Domain-oriented Knowledge Acquisition," Knowledge Acquisition (1992), vol. 4, pp. 445-476.
Eskenasi, Ayram. "Incorporating Student Models in Adaptive Testing Systems," Educational & Training Technology International, May 1993, vol. 30, No. 2, pp. 135-143.
Evaluating Preclinical Medical Students by Using Computer-Based Problem-Solving Examinations,: Stevens, RH, et al. Academic Medicine vol. 64, pp. 685-687.
Fact Sheet, UMLS Semantic Network, U.S. Dept. of Health and Human Services, Nov. 1991.
Fact Sheet, Unified Medical Language System .TM., U.S. Dept. of Health and Human Services, Jan. 1993.

Farr, Brad R. et al. "Representation of Preferences in Decision-Support Systems," Computers and Biomedical Research 25, 324-335 (1992).
Fatemeh, Zahedi. "A Method for Quantitative Evaluation for Expert Systems" European Joumal of Operational Research, 48 (1990) pp. 136-147.
Felciano, R. M. et al. "Multimedia Clinical Simulation based on Patient Records: Authoring, User Interface, Pedagogy," Knowledge Systems Laboratory Report KSL-94-43 (1994).
Frawley, K. A. "Do Computerized Patient Records Risk Invading Patient Privacy More than Paper Records?," Nov. 5, 1993.
Friedman, Carol et al. "The Canon Group's Effort: Working Toward a Merged Model," Journal of the American Medical Informatics Association, vol. 2, No. 1, Jan./Feb. 1995.
Friedman, R. B. "A Computer Program for Simulating the Patient-Physician Encounter," J Med Educ 1973, vol. 48, pp. 92-97.
Frost, R. D. et al. "Integrated Clinical Decision Support Using an Object-Oriented Database Management System" Methods of Information in Medicine 1993; 32: 154-160.
Generate, Simmons R. "Test and Debug: A Paradigm for Combining Associational and Causal Reasoning in: David M, Krivine JP, Simmons R., Second Generation Experts Systems" Springer Verlag, New York, NY, 1993. pp. 79-92.
Genersereth, M. "Diagnosis Using Hierarchical Design Models," Proceedings of National Conference on AI, 1982.
Gennari, John H. et al. "Mapping Domains to Methods in Support of Reuse," Knowledge Systems Laboratory Report KSL-93-57, (1994).
Gennari, John H. et al. "Reuse with Protege-II: From Elevators to Ribosomes," Knowledge Systems Laboratory Report KSL-94-71 (1995).
Gibbons, A. S. et al. "The Future of Computer-Managed Instruction (CMI)," Educational Technology, May 1993, pp. 7-11.
Gilardoni, Luca et al. "Hierarchical Pattern Matching for Knowledge Based News Categorization," Quinary SpA, Milano Italy.
Gonella, J. S. et al. "Disease Staging Clinical Criteria," (eds.). 4.sup.th ed. Ann Arbor, Michigan: Medstat Systems, 1994.
Goodkovsky, V. A. et al. "Pop Class Intelligent Tutoring Systems: Shell, Toolkit & Design Technology," Moscow State Institute for Physics and Engineering.
Goodyear, O. M. et al. "Integrating a Medical Database and Advisory System," Med. Inform. (1991), vol. 16, No. 3, pp. 315-321.
Green, Larry A. et al. "How Representative of Typical Practice Are Practice-Based Research Networks?," Arch Family Med. vol. 2, Sep. 1993.
Gudtafson, David G. et al. "Decision Theoretic Methodology for Severity Index Development Methodology," Medical Decision Making, vol. 6, No. 1, Jan.-Mar. 1986.
Hakman, M. et al. "KBSIM: A System for Interactive Knowledge-based Simulation," Computer Methods and Programs in Biomedicine, vol. 34, (1991), pp. 91-113.
Haladyna, Thomas M. "A Taxonomy of Multiple-Choice Item-Writing Rules," Applied Measurement in Education, 2(1), 37-50 (1989).
Harless, W. G. et al. "Merit—an application of Case, Deland EC (ed)," Information Technology in Health Science Education, Plenum Press, New York 1978, pp. 565-569.
Hartz, Arthur et al. "Stochastic Thresholds," Medical Decision Making, vol. 6, No. 3, Jul.-Sep. 1986.
Heckerling, P. S. et al. "The Effect of Incomplete Knowledge on the Diagnoses of a Computer Consultant System," Med. Inform. (1991), vol. 16, No. 4, pp. 363-370.
Heckerman, D. E. et al. "Toward Normative Expert Systems: Part I the Pathfinder Project," Knowledge Systems Laboratory Report KSL-92-66 (1992).
Hersh, William R. et al. "A Performance and Failure Analysis of Saphire with a Medline Test Collection," Journal of the American Medical Informatics Association, vol. 1, No. 1, Jan./Feb. 1994.
Herskovits, Edward et al. "Kutato: An Entropy-Driven System for Construction of Probabilistic Expert Systems from Databases," Knowledge Systems Laboratory Report KSL-90-22, (1990).
Herzog, Christian. "Understanding Students' Solutions in SYPROS," AI-ED 95—Poster Session.

Hietala, Pentti et al. "A Framework for Building Agent-based Learning Environments," University of Tampere, Dept. of Computer Science, Finland.

Hilden, Jorgen et a. "A Pittfall in Utility Assessment—Patients' Undisclosed Investment Decisions," Medical Decision Making, vol. 12, No. 1, Jan.-Mar. 1992.

Horvitz, Eric J. "Rational Metareasoning and Compilation for Optimizing Decisions under Bounded Resources," Knowledge Systems Laboratory Report KSL-89-81 (1990).

Huanying, Gu et al. "Utilizing OODB Schema Modeling for Vocabulary Management," CIS Dept. & CMS NJIT, Newark, NJ pp. 274-278.

Hughes, Christopher. "The Representation of Uncertainty in Medical Expert Systems," Med. Inform. (1989), vol. 14, No. 4, pp. 269-279.

Ikeda, Mitsuru et al. "Ontological Issues of CSCL Systems Design," ISIR, Osaka University, Osaka Japan, pp. 242-249.

Ikeda, Mitsuru et al. "Ontological Issues of CSCL Systems Design," Osaka University, Osaka Japan.

Isaacs, E. et al. "Graphical Access to Medical Expert Systems: IV. Experiments to Determine the Role of Spoken Input," Methods of Information in Medicine 1993; 32: pp. 18-32.

Jain, Nielsh L. et al. "Ranking Radiotherapy Treatment Plans Using Decision-Analytic and Heuristic Techniques," Computers and Biomedical Research, vol. 25, pp. 374-383 (1992).

Jambaud, Piereet et al. "Contribution to Negotiation Studying: A Knowledge Items Approach," LIRMM, UMR CNRS-UM2 n 9928, Montpellier Cedex.

Jimison, Holly B. et al. "Patient-Specific Explanation in Models of Chronic Disease," Knowledge Systems Laboratory Report KSL-92-60 (1992).

Johannson, B. G. et al. "An Object oriented approach to Interpret Medical Knowledge Based on Arden Syntax," Proceedings of Annual Symposium of Computer Appl. Med. Car., 1992. pp. 52-56.

Johansson, B. et al. "Database and Knowledge Base Integration—A Data Mapping Method for Arden Syntax Knowledge Modules," Methods of Information in Medicine, 1996; 35: 302-308.

Jonassen, David H. "Constructivist Uses of Expert Systems to Support Learning," Journal of Computer-Based Instruction, Summer 1993, vol. 20, No. 3, pp. 86-94.

Kahn, M. G. et al. "Representation and Use of Temporal Information in ONCOCIN," Knowledge Systems Laboratory Report KSL-85-8 (1987).

Kahn, Michael G. et al. "Model-Based Interpretation of Time-Varying Medical Data," Knowledge Systems Laboratory Report KSL-89-34, (1989).

Kahn, Michael G. et al. "TQuery: A Context-Sensitive Temporal Query Language," Computers and Biomedical Research 24, 401-419 (1991).

Kassirer, Jerome P. et al. "Decision Analysis: A Progress Report," Annals of Internal Medicine, 1987; 106:275-291.

Katz, Irvin R. "From Laboratory to Test Booklet: Using Expert-Novice Comparisons to Guide Design of Performance Assessments," presented at 1994 Annual Meeting of AERA.

Kelly, G. A. "The Psychology of Personal Constructs," Norton Press, New York, NY, 1995.

Klein, David A. et al. "Interactive Diagnosis and Repair of Decision-Theoretic Models," Knowledge Systems Laboratory Report KSL-90-19 (1992).

Kleinmuntz, Benjamin. "Computers as Clinicians: An Update," Computer Biol. Med., vol. 22, No. 4, pp. 227-237, 1992.

Kolstad, Rosemarie K. "The Failure of Distractors on Complex Multiple-Choice Items to Prevent Guessing," Educational Research Quarterly, vol. 8, No. 2, 1983.

Koubek, Richard J. "The Implementation and Evaluation of a Theory for High Level Cognitive Skill Acquisition Through Expert Systems Modeling Techniques," Ergonomics, 1989, vol. 32, No. 11, pp. 1419-1429.

Kreiter, Clarence D. "Effectiveness of Multiple True-False Items," Applied Measurement in Education, 2(3), 207-216.

LaDuca, Anthony. "Framing the Primary Care Physician," AAFP Primary Care Competencies Conference, Jun. 4, 1994.

Lane, C. D. et al. "Graphical Access to Medical Expert Systems: II. Design of an Interface for Physicians," Knowledge Systems Laboratory Report KSL-85-15 (1986).

Lanzola, G. et al. "A Specialized Framework for Medical Diagnostic Knowledge-Based Systems," Computers and Biomedical Research, vol. 25, pp. 351-365 (1992).

Leman, Stephane et al. "A Multi-Agent Approach to Model Student Reasoning Process," Iremia, Universite de La Reunion, La Reunion, France, pp. 258-264.

Lewinson, Lisa, "Representing Medical Knowledge—The Arden Syntax," PC AI, Jul./Aug. 1994.

Li, Zhongmin et al. "Developing a Research Reference Interface for Knowledge-Based Instructional Design Tools," Educational Technology/Aug. 1991.

Lim, Ian et al. "Rule Based Artificial Intelligence Expert System for Determination of Upper Extremity Impairment Rating," Computer Methods and Programs in Biomedicine, 39 (1993), pp. 203-211.

Lindberg, D. A. et al. "The Unified Medical Language System," Methods of Information in Medicine 1993; 32: 281-291.

Linster, Marc et al. "Use of KADS to Create a Conceptual Model of the ONCOCIN Task," Knowledge Systems Laboratory Report KSL-92-36, (1992).

Linster, Marc. "Towards a Second Generation Knowledge Acquisition Tool," Knowledge Acquisition (1989) 1, pp. 163-183.

Lowe, Henry J. et al. "Understanding and Using the Medical Subject Headings (MeSH) Vocabulary to Perform Literature Searches," JAMA, Apr. 13, 1994, vol. 271, No. 14.

Marek, Victoret et al. "Algorithms for Knowledge Acquisition and Patient Generation" University of Kentucky, Mar. 29, 1996.

Mays, Eric et al. "Scalable and Expressive Medical Terminologies," 1996 AMIA, Inc., pp. 259-263.

McLeish, Mary et al. "Issues in the Development of Intelligent Tutoring Systems," Dept. of Computing & Information Science, Univ. of Guelpoh, Ontario, May 1987.

McSherry, D. M. G. "Intelligent Dialogue Based on Statistical Models of Clinical Decision-Making," Statistics in Medicine, vol. 5, 497-502 (1986).

Mehrez, Abraham et al. "Quality-adjusted Life Years, Utility Theory, and Healthy-years Equivalents," Medical Decision Making, vol. 9, No. 2, Apr.-Jun. 1989.

Merola, A. J. et al. "Computer-supported Independent Study in the Basic Medical Sciences in: DeLand EC (ed.)," Information Technology in Health Science Education, Plenum Press, New York, 1973.

Miaoulis, G. et al. "New Role of a Medical Documentation System," Med. Inform. (1992), vol. 17, No. 3, pp. 165-178.

Midoro et al. "Interactive Video and Artificial Intelligence: Convenient Marriage," PLET 25, 4.

Miller, R. A. et al. "Quick Medical Reference (QMR) for Diagnostic Assurance," Computing, vol. 5, 1986. pp. 34-49.

Millis, M. D. et al. "PSY/JD: An Advisory System for Legal Aspects of Decision Making in the Psychiatric Emergency Room," Knowledge Systems Laboratory Report KSL-90-54 (1990).

Mode, C. J. "A Mathematical Overview of a Computer Simulation Model of Maternity Histories with Illustrative Examples," IMA Journal of Mathematics Applied in Medicine & Biology (1984), vol. 1, pp. 107-121.

Motta, Enrico et al. "Methodological Foundations of KEATS, the Knowledge Engineer's Assistant," Knowledge Acquisition (1991) vol. 3, pp. 21-27.

Mullins, H. C. et al. "The Efficacy of SNOMED, Read Codes, and UMLS in Coding Ambulatory Family Practice Clinical Records," 1996 AMIA, Inc., pp. 135-139.

Musen, M. A. et al. "PROTEE-II: Computer Support for Development of Intelligent Systems from Libraries of Components" MEDINFO 95 Proceedings, 1995 IMIA.

Musen, Mark A. "Automated Support for Building and Extending Expert Models," Knowledge Systems Laboratory Report KSL-86-26 (1989).

Musen, Mark A. "Languages for Knowledge Acquisition: Building and Extending Models," Knowledge Systems Laboratory Report No. KSL-89-07 (1989).

Musen, Mark A. et al. "A Component-Based Architecture for Automation of Protocol-Directed Therapy," Knowledge Systems Laboratory Report KSL-95-28 (1995).

Musen, Mark A. et al. "A Problem-Solving Model for Protocol-Based Care: From e-ONCOCIN to EON," Knowledge Systems Laboratory Report KSL-91-61 (1991).

Musen, Mark A. et al. "PROTEGE II: Computer Support for Development of Intelligent Systems From Libraries of Components," Knowledge Systems Laboratory Report KSL-94-60.

Musen, Mark A. et al. "T-Helper: Automated Support for Community-Based Clinical Research," Knowledge Systems Laboratory Report KSL-92-08 (1992).

Musen, Mark A. et al. "Use of a Domain Model to Drive an Interactive Knowledge-Editing Tool," Knowledge Systems Laboratory Report KSL-86-24, (1987).

Musen, Mark et al. "Rationale for Knowledge Base Redesign in a Medical Advice System," Knowledge Systems Laboratory Report KSL 85-17.

Naeymi-Rad, Frank. "A Feature Dictionary Supporting a Multi-domain Medical Knowledge Base," Computer Methods and Programs in Biomedicine, vol. 30 (1989), pp. 217-228.

Norman, Joseph. "Building the Computer-Based Patient Record," Knowledge Systems Laboratory Report KSL-95-24 (1995).

Nowland, W. A. et al. "From Termiunology to Terminology Services," 1994 AMIA, Inc.

Okamoto, Toshio et al. "The Intelligent Learning Support System on the Distributed Cooperative Environment," The Graduate School of Information Systems, University of Electro-Communications, Tokyo, Japan.

Paquette, Gilbert et al. "An Intelligent Support System for Course Design," Educational Technology, Nov.-Dec. 1994, pp. 50-57.

Pauker, Stephen G. et al. "Medical Progress—Decision Analysis," Pauker, The New England Journal of Medicine, vol. 316, No. 5, Jan. 29, 1987.

Perreault, Leslie E. "Automatic Test Case Generation Modeling Patient States and Physician Actions," Knowledge Systems Laboratory Report KSL-87-63, (1987).

Piemme, Computer-assisted learning and evaluation in medicine, Jul. 1998, The Journal of the American Medical Association, vol. 260 No. 3, pp. 367-373.

Pinciroli, F. et al. "Object-orientated DBMSTtechniques for Time-oriented Medical Record," Med. Inform. (1992), vol. 17,No. 4, pp. 231-241.

Polaschek, Jeanette X. et al. "A Computer Program for Statistically Based Decision Analysis," Knowledge Systems Laboratory Report KSL-90-50 (1990).

Pole, P. M. et al. "Mapping the Galen Core Model to SNOMED-III: Initial Experiments," 1996. AMIA, Inc., pp. 100-104.

Poon, Alex et al. "Augmented Transition Networks as a Representation for Knowledge-Based History-Taking Systems," Knowledge Systems Laboratory Report KSL-92-20, (1992).

Poses et al. "Evaluating Physicians' Probabilistic Judgments" Medical Decision Making, vol. 8, No. 4, Oct.-Dec. 1988.

Puerta, Angel R. et al. "Model-Based Generation of User Interfaces," Knowledge Systems Laboratory Report KSL-94-51 (1994).

Puerta, Angela R. et al. "Modeling Tasks with Mechanism," Knowledge Systems Laboratory Report KSL-92-30, (1992).

Rassinoux, Anne Marie et al. "Modeling Principles for QMR Medical Findings," 1996 AMIA, Inc., pp. 264-268.

Rector, A. L. et al. "A Framework for Modeling the Electronic Medical Record," Methods of Information in Medicine 1993, 32: 109-119.

Rector, A. L. et al. "Goals for Concept Representation in the Galen Project," 1994 AMIA, Inc.

Rector, A. L. et al. "Medical-concept Models and Medical Records: An Approach Based on Galen and Pen&Pad," Journal of the American Medical Informatics Association, vol. 2, No. 1, Jan./Feb. 1995.

Reshetar, R. A. et al. "An Adaptive Testing Simulation for a Certifying Examination," Presented at the Annual Meeting of the American Educational Research Association, San Francisco, CA, Apr. 1992.

Rikken, Floor et al. "Specifying Adverse Drug Reactions Formulating Contexts Through CLARIT Processing of Medical Abstracts," Dept. of Social Pharmacy and Pharmacoepidemiology, University of Groningen, The Netherlands.

Rocha, Roberta A. et al. "Coupling Vocabularies and Data Structures: Lessions from LOINCJ," 1996 AMIA, Inc., pp. 90-94.

Rothenfluh, Thomas E. et al. "Reusable Ontologies, Knowledge-Acquisition Tools, and Performance Systems: PROTEGE-II Solutions to Sisyphus-2," Knowledge Systems Laboratory Report KSL-93-65 (1994).

Rothwell, David J. et al. "Managing Information with SNOMED: Understanding the Model," 1996. AMIA, Inc., pp. 80-83.

Rovinelli, Richard J. "Research and Developmental Issues for a Computer-Based Testing Project for the American Board of Family Practice," Psychometric Consultant.

Rubinstein, R. Y. "Simulation and the Monte Carlo Method," Wiley and Sons, Inc., New York, NY, 1981.

Russ, Thomas A. "A System for Using Time Dependent Data in Patient Management," Medinfo 86, Elsevier Science Publishers B.V., 1986.

Ryan, Margaret. "Distance Health Care is Latest Medicine," Electronic Engineering Times, pp. 55-56, Apr. 29, 1996.

Sager, Naomi et al. "Natural Language Processing and the Representation of Clinical Data," Journal of the American Medical Informatics Association, vol. 1, No. 2, Mar./Apr. 1994, pp. 142-160.

Santos-Gomez, Lucinio et al. "Empirical Evaluation of Decision Tables for Constructing and Comprehending Expert System Rules," Knowledge Acquisition (1992) vol. 4, pp. 427-444.

Satomura, Y. et al. "Automated Diagnostic Indexing Natural Language Processing," Med. Inform. (1992), vol. 17, No. 3, pp. 149-163.

Schroder, Martin. "Knowledge-based Processing of Medical Language: A Language Engineering Approach," Uni. of Hamburg, Germany.

Schwartz, William B. et al. "Artificial Intelligence in Medicine," Sounding Board, vol. 316, No. 11, pp. 685-688.

Seidel, Robert J. "An Historical Perspective and a Model for Evaluation of Intelligent Tutoring Systems," Journal of Educational Computing Research, vol. 10(2) pp. 103-128, 1994.

Shahar, Yuval et al. "A Temporal-Abstraction System for Patient Monitoring,"Knowledge Systems Laboratory Report KSL-92-14 (1992).

Shahar, Yuval et al. "Knowledge-Based Temporal Abstraction in Clinical Domains," Knowledge Systems Laboratory Report KSL-95-23 (1995).

Shahar, Yuval et al. "Resume: A Temporal-Abstraction System for Patient Monitoring," Knowledge Systems Laboratory Report KSL-92-84, (1992).

Shahar, Yuval et al. "Temporal-Abstraction Mechanisms in Management of Clinical Protocols," Knowledge Systems Laboratory Report KSL-91-19 (1991).

Shahar, Yuval. "A Framework for Knowledge-Based Temporal Abstraction," Knowledge Systems Laboratory Report KSL-95-29 (1995).

Shea, Judy A. et al. "An Adaptation of Item Modeling for Developing Test-Item Banks," Teaching and Learning in Medicine, vol. 4, No. 1, pp. 19-24 (1992).

Shwe, Michael et al. "An Empirical Analysis of Likelihood-Weighting Simulation on a Large, Multiply-Connected Belief Network," Knowledge Systems Laboratory Report KSL-90-23 (1992).

Simmons, David et al. "The Roles of Knowledge and Representation in Problem Solving, in Second Generation Expert Systems," Springer Verlag, New York, NY 1993. pp. 27-45.

Sittig, D. F. et al. "Evaluating a Computer-Based Experiential learning Simulation: A Case Study Using Criterion-Referenced Testing," Computer Nurs. vol. 13, 1995. pp. 17-24.

Sleeman, D. "Intelligent Tutoring Systems: A Review," School of Education & Dept. of Computer Science, Stanford University.

Solomon, D. J. et al. "A Pilot Study of the Relationship between Expert's Ratings and Scores Generated by the NBME's Computer-Based Examination System," Academic Medicine, vol. 67, 1992. pp. 130-132.

Spector, J. Michael et al. "Intelligent Frameworks for Instructional Design," Educational Technology, Oct. 1992, pp. 21-27.

Spyns, P. "Natural Language Processing in Medicine: An Overview," Methods of Information in Medicine 1996; 35: pp. 285-301.

Stein, Adam et al. "Knowledge Acquisition for Temporal Abstraction," 1996 AMIA, Inc., pp. 204-208.

Stillman, P. L. et al. "Ensuring the Clinical Competence of Medical School Graduates Through Standarized Patients," Arch Int Med 1978, vol. 147, pp. 1049-1052.

Stocking, M. L. "An Alternative Method for Scoring Adaptive Tests, Research Report," RR-94-98, 1994.

Stonebraker, Michael. "The Design of the Postgres Storage System," EECS Dept., University of California, Berkeley, CA.

Stuart-Buttle, C. D. G. et al. "A Language of Health in Action: Read Codes, Classifications and Groupings," 1996. AMIA, Inc., pp. 75-79.

Suchman, L. A. et al. "Understanding Practice: Video as Medium for Reflection and Design, IN: Greenbaum, J, Kyng M (eds)," Design at Work: Cooperative Design of Compute Systems. Lawrence Earlbaum Associates 1991, pp. 65-89.

Sumner, W. "A Review of Iliad and QMR for Primary Care Providers," Archives of Family Medicine, vol. 2, 1993. pp. 87-95.

Sumner, Walton et al. "A Revolution in the Assessment of Clinical Knowledge," JABFP, Jan./Feb. 1996, vol. 9, No. 1.

Sumner, Walton II et al. "Data Transformations for Patient Simulations," presented at Proceedings of the Nineteenth Annual Symposium on Computer Applications in Medical Care, New Orleans, LA, Nov. 1995.

Sumner, Walton II et al. "Describing Medicine and Generating Patients with Parallel Health State Networks," Division of General Medical Sciences, Dept. of Internal Medicine, Washington University, St. Louis, Missouri.

Sumner, Walton II et al. "Designing a Knowledge Base to Support Family Practice Certification Examinations," presented at Proceedings of the Seventeenth Annual Symposium on Computer Applications in Medical Care, Washington, D.C., 1993.

Sumner, Walton. "A Review of Iliad and QMR for Primary Care Providers," Program in Medical Information Science, Dartmouth Medical School.

Tak-Wai, Chan. "Learning Companion Systems, Social Learning Systems, and Intelligent Virtual Classrooms," Dept. of Computer Science and Information Engineering, National Central University, Taiwan.

Tecuci, Gheorghe et al. "A Framework for Knowledge Base Refinement Through Multistrategy Learning and Knowledge Acquisition," Knowledge Acquisition (1994) 6, pp. 137-162.

"The Furor Over Data on Doctors: You Bet Your Life. Do You Know the Odds?," New York Times, May 29, 1994.

The Irwin Handbook of Telecommunications, Green, James Harry. Irwin Professional Publishing, 2.sup.nd ed., 1992.

Tsuji, S. et al. "Graphical Access to Medical Expert Systems: I. Design of a Knowledge Engineers Interface," Knowledge Systems Laboratory Report KSL-85-11 (1986).

Tu, S. W. et al. "A methodology for Determining Patients Eligibility for Clinical Trials," Knowledge Systems Laboratory Report KSL-92-78 (1992).

Tu, S. W. et al. "Episodic Skeletal-Plan Refinement Based on Temporal Data," Knowledge Systems Laboratory Report KSL-87-70 (1989).

Tu, Samson W. et al. "Ontology-Based Configuration of Problem-Solving Methods and Generation of Knowledge-Acquisition Tools: Application of Protege-II to Protocol-Based Decision Support," Knowledge Systems Laboratory Report KSL-94-22 (1994).

Van der Lei, Johan et al. "A Model for Critiquing Based on Automated Medical Records," Knowledge Systems Laboratory Report KSL-91-18 (1991).

Van der Lei, Johan et al. "Comparison of Computer-Aided and Human Review of General Practitioners' Management of Hypertension," Lancet 338; 1504-1508, Dec. 14, 1991.

Van der Lei, Johan et al. "Critiquing Physician Decision Making Using Data from Automated Medical Records: Assessing the Limitations," Fourteenth Annual Symposium on Computer Applications in Medical Care, pp. 559-563, Washington, DC, Nov. 1990.

Van Marcke, Kris et al. "Learner Adaptivity in Generic Instructional Strategies," Knowledge Technologies N.V., pp. 323-337.

Van Marcke, Kris. "A Generic Task Model for Instruction," Knowledge Technologies N.V., Brussels, Belgium, pp. 171-194.

Wallace, Scott. "The Computerized Patient Record," TE, May 1994.

Webster, Laurie et al. "Exercise Countermeasure Protocol Management Expert System" Computer Methods and Programs in Biomedicine, 39 (1993) pp. 217-223.

Weinberg, A. D. "CAI at the Ohio State University College of Medicine; Tutorial Evaluation System," Computer Biology Medicine 1973. vol. 3, pp. 299-305.

Wellman, Michael P. et al. "Automated Critiquing of Medical Decision Trees," Medical Decision Making, vol. 9, No. 4, Oct.-Dec. 1989.

Widman, Lawrence E. "Expert System Reasoning About Dynamic Systems Semi-quantitative Simulation," Computer Methods and Programs in Biomedicine, 29 (1989) pp. 95-113.

Widman, Lawrence E. "Representation Method for Dynamic Causal Knowledge Using Semi-Quantitative Simulation," Medinfo 86, Elsevier Science Publishers (1986).

Wigton, Robert S. "Use of Linear Models to Analyze Physicians' Decisions," Medical Decision Making, vol. 8, No. 4, Oct.-Dec. 1988.

Woodward, Beverly. "The Computer-Based Patient Record and Confidentiality," The New England Journal of Medicine, vol. 333, No. 21, Nov. 23, 1995.

Woolf, Beverly. "Toward a Computational Model of Tutoring," ETR &D, vol. 40, No. 4, pp. 49-64.

Woolf, Intelligent Multimedia Tutoring Systems, Apr. 1996, Communications of the ACM, vol. 39 No. 4, pp. 30-31.

Yoshikawa, Masazumi et al. "Constraint Satisfaction with a Multi-Dimensional Domain," C&C Systems Research Laboratories, NEC Corporation, Japan, pp. 252-259.

Zech, Linda et al. "Computer Technology and Complex Problem Solving: Issues in the Study of Complex Cognitive Activity," EARLI, 1995 Symposium.

Zenz, Quing et al. "Mapping Medical Vocabularies to the Unified Medical Language System," 1996 AMIA, Inc., pp. 105-109.

\* cited by examiner

COMPUTER ARCHITECTURE AND PROCESS OF PATIENT GENERATION, EVOLUTION, AND SIMULATION FOR COMPUTER BASED TESTING SYSTEM

RELATED APPLICATIONS

This application is a divisional of U.S. patent application Ser. No. 09/759,205, filed Jan. 16, 2001, which is a continuation of U.S. patent application Ser. No. 08/961,185, filed Oct. 30, 1997, which claims priority from U.S. provisional patent application entitled COMPUTER ARCHITECTURE AND PROCESS FOR PATIENT GENERATION, EVOLUTION, AND SIMULATION, Ser. No. 60/029,856, to Rovinelli, et al., filed Oct. 30, 1996, the details of which are hereby incorporated by reference.

This application is related to U.S. patent application Ser. No. 11/203,230, filed Aug. 15, 2005, which is a continuation of U.S. patent application Ser. No. 10/265,599, filed Oct. 8, 2002, which is a divisional of U.S. patent application Ser. No. 09/521,242, filed Apr. 5, 2000, which is a nonprovisional of U.S. Provisional Patent Application No. 60/127,850.

FIELD OF THE INVENTION

The present invention is generally related to a computer architecture and process for patient generation, evolution, and simulation, and more particularly to a computer architecture and process for patient generation, evolution, and simulation for a computer based testing system.

BACKGROUND OF THE RELATED ART

Medical certifying organizations have traditionally relied upon paper and pencil cognitive examinations as a method for the assessment of the candidate's medical knowledge. Traditional formats such as multiple choice questions have well-defined operating characteristics and reliability for examining cognitive knowledge capabilities. See, for example, Stocking M L, An alternative method for scoring adaptive tests, Research Report RR-94-98, 1994, incorporated herein by reference.

However, these tools generally measure in only cognitive knowledge. These methods provide only primitive ability to assess a candidate's problem-solving abilities. See, for example, Stillman P L, Swanson D B, Ensuring the clinical competence of medical school graduates through standardized patients, Arch Int Med 1978, Vol. 147, pages 1049-52, incorporated herein by reference.

Several organizations have previously experimented with computer-delivery of clinical content and evaluation. In the late 1960s and 1970s, the Ohio State University developed a self-directed Independent Study Program which utilized a "Tutorial Evaluation System," for conveying curriculum content. See, for example, Weinberg A D, CAI at the Ohio State University College of Medicine, Comput Biol Med 1973, Vol. 3, pages 299-305; Merola A J, Pengov R E, Stokes B T, Computer-supported independent study in the basic medical sciences in: DeLand E C (ed). Information Technology in Health Science Education, Plenum Press, New York, 1973, incorporated herein by reference.

Co-synchronously Dr. Octo Barnett's laboratory at the Massachusetts General hospital began development of clinical simulations. See, for example, Barnett G O, The use of a computer-based system to teach clinical problem-solving, Computers in Biomedical Research, Academic Press, New York 1974; Vol. 4, pages 301-19; Barnett G O, Hoffer E P, Famiglieti K T, Computers in medical education: present and future, Proceedings of the Seventh Annual Symposium on Computer Applications in Medical Care, IEEE Press, Washington, D.C. 1983, pages 11-13, incorporated herein by reference. The clinical simulations used the MUMPS language.

At approximately the same time, investigators at the University of Illinois developed a simulation model known as (Computer-Associated Simulation of the Clinical Encounter, or "CASE"). See, for example, Harless W G, Farr N A, Zier M A, et al., MERIT—an application of CASE, Deland E C (ed), Information Technology in Health Science Education, Plenum Press, New York 1978, pages 565-69, incorporated herein by reference. This system was at one time considered by the American Board of Internal Medicine (ABIM) as at least one component of a recertification process. Friedman R B, A computer program for simulating the patient-physician encounter, J Med Educ 1973, Vol. 48, pages 92-7, incorporated herein by reference. Research supported by the ABIM demonstrated that a computerized examination system appeared feasible in professional evaluation/certification settings. Reshetar, R A, et al., An Adaptive Testing Simulation for a Certifying Examination, presented at the Annual Meeting of the American Educational Research Association, San Francisco, Calif., April, 1992, incorporated herein by reference.

Stevens and colleagues have also demonstrated the feasibility of using computer-based systems for testing problem-solving ability in undergraduate medical school curriculum applications. See, for example, Stevens R H, et al, Evaluating Preclinical Medical Students by Using Computer-Based Problem-Solving Examinations, Academic Medicine 1989, Volume 64, pages 685-87, incorporated herein by reference. Sittig and colleagues have also examined the utility of computer-based instruction in teaching naïve users basic computer techniques such as "drag and drop" and other computer operations. See, for example, Sittig D F, Jiang Z, Manfre S, et al., Evaluating a computer-based experiential learning simulation: a case study using criterion-referenced testing, Comput Nurs; 1995, Vol. 13, pages 17-24, incorporated herein by reference.

We have determined that the above described medical assessment processes suffer from two weaknesses: 1) test development requires re-generation of an examination with new material on a recurring (usually annual) basis; 2) although multiple choice questions demonstrate reliable performance in measuring cognitive knowledge, the use of this format for assessing clinical problem solving has not been supported by the literature. Another system was developed at the University of Wisconsin. This project served as the nidus for the Computer-Based Examination (CBX) developed by the National Board of Medical Examiners (NBME). See, for example, Friedman R B, A computer program for simulating the patient-physician encounter, J Med Educ 1973, Vol. 48, pages 92-7; Clyman, Stephen G., Orr, Nancy A., Status Report on the NBME's Computer-Based Testing, Academic Medicine 1990, Vol. 65, pages 235-41, incorporated herein by reference. NBME's CBX development project has been in evolution for over a decade, and has demonstrated validity in examining professional degree candidates. See, for example, Solomon D J, Osuch J R, Anderson K, et al., A pilot study of the relationship between experts' ratings and scores generated by the NBME's computer-based examination system, Academic Medicine 1992, Vol. 67, pages 130-32, incorporated herein by reference.

However, we have determined that the CBX model suffers from the problem that the clinical simulations are "hard-wired" in computer source code which must be re-coded for each new examination. Once the simulation has been used widely, the examination contents are no longer secure, necessitating continuous cycles of new simulation development.

The expert system literature describes the evolution in evaluation and training systems. Early artificial intelligence/ expert system work concentrated on "rules of thumb" or heuristics to represent problem-solving strategies identified by domain experts. See, for example, David J M, Krivine J P, Simmons R., Second generation expert systems: a step forward in knowledge engineering, in: David J M, Krivine J P, Simmons R. Second Generation Expert Systems, Springer Verlag, New York, N.Y. 1993, pages 3-23, incorporated herein by reference. We have determined that these rule-based systems were necessarily constrained to narrow domains, and that the knowledge contained in the rules was difficult to validate. Id.

In addition, early expert systems suffered from rapidly declining performance when exposed to circumstances outside narrowly defined domains. See, for example, Davis R. Expert systems: where are we and where do we go from here, AI Magazine, 1983, Vol. 3, pages 3-22; Simmons R. Generate, Test and Debug: A paradigm for combining associational and causal reasoning, in: David M, Krivine J P, Simmons R., Second Generation Expert Systems, Springer Verlag, New York, N.Y. 1993, pages 79-92, incorporated herein by reference. We have determined that this phenomenon occurred at least in part due to interactions among the many rules needed to define a domain. Recent work indicates that the robustness of such systems is enhanced by providing knowledge of different types. See, for example, Simmons R, Davis R., The roles of knowledge and representation in problem solving, In: David M, Krivine J P, Simmons R., Second Generation Expert Systems, Springer Verlag, New York, N.Y. 1993, pages 27-45, incorporated herein by reference.

We have further determined that experts generally not only relate to one dimension of knowledge when defining a rule, but also rely upon expansive knowledge of how systems work (i.e., physiology and pathophysiology in the medical domain) in performing real-world problem-solving. See, for example, Davis R., Expert systems: where are we and where do we go from here, AI Magazine, 1983, Vol. 3, pages 3-22, incorporated herein by reference. This realization has led to re-thinking regarding structure of knowledge-based systems to reflect the tasks such a system should accomplish, the methods the system should use to accomplish the tasks, and the knowledge required to support these methods. See, for example, David J M, Krivine J P, Simmons R., Second generation expert systems: a step forward in knowledge engineering, In: David J M, Krivine J P, Simmons R., Second Generation Expert Systems, Springer Verlag, New York, N.Y. 1993, pages 3-23, incorporated herein by reference.

We have also determined that knowledge-acquisition for such systems entails development of a model for the domain and instantiation (i.e., encode and enter needed information into the system's data structure) of the model with information acquired from knowledge donors. See, for example, David M, Krivine J P, Simmons R., Second generation expert systems: a step forward in knowledge engineering, In: David M, Krivine J P, Simmons R., Second Generation Expert Systems, Springer Verlag, New York, N.Y. 1993, pages 3-23; Breuker J, Weilenga B., Models of expertise in knowledge acquisition, In: Gida and Tasso (eds), Topics in Expert System Design: Methodologies and Tools, North Holland Publishing, 1989, incorporated herein by reference.

To obviate the above described weaknesses, we have determined that it is desirable to provide a computer-based testing project which will: 1) instantiate medical knowledge as object-oriented data structures known as knowledge base of family medicine; 2) utilize the medical knowledge structures to create realistic clinical scenarios (simulated patients); and 3) assess the candidate's clinical problem solving ability as the effective intervention in the clinical progress of the simulated patient through the selection of various actions made available by the testing system.

SUMMARY OF THE INVENTION

The computer-based testing system described herein represents knowledge at multiple levels of complexity. For example, reactive airways disease is represented as a series of health states: Normal (Non-reactive) Airways, Reactive Airways-Mild, Reactive Airways-Moderate, and Reactive Airways-Severe. Each health state contains identifiers which relate the particular health state to precedents and antecedents (e.g., Normal Airways serves as the precursor health state for Mild Reactive airways disease, and Mild, Moderate and Severe Reactive Airways Disease represent target health states from the Normal circumstance.)

Each health state in turn has associated findings, and specific findings. For example, the Normal Airways state, the Finding "Shortness of Breath" is instantiated with the Specific Finding "No shortness of breath." Similarly, other Findings such as Respiratory Function and Severe Asthma Attack Frequency are instantiated with corresponding normal Specific Findings (Normal Respiratory Functions, and No Severe Attacks.) This representation transports to each new health state in a manner which we have determined to be analogous to diagnosis. See, for example, Genesereth M., Diagnosis using hierarchical design models, Proc. National Conference on AI, 1982, incorporated herein by reference.

The computer-based testing system of the present invention partitions knowledge into fundamental types: Health States, Agents, Findings, Specific Findings and Patterns describe system behaviors and characteristics. Courses-of-Action describe human activities which modify and evaluate the health state information and characteristics described in the model. Subdivision of knowledge types in this manner facilitates the knowledge acquisition process. This subdivision also promotes multiple levels of knowledge abstraction, which enhances the system's ability to represent varying levels of complexity.

For example, in the Computer-Based Testing System, a pattern such as incidence is further sub-divided into sub-patterns such as incidence in females versus males, and incidence in various racial/ethnic groups.

Multiple levels of abstraction and types of knowledge impose a substantial knowledge acquisition challenge. Knowledge acquisition includes several possible methodologies, including direct questioning of domain experts/protocol analysis, see, for example, Ericsson KaA, Simon H A, Protocol Analysis: Verbal Reports as Data, MIT Press. Cambridge, Mass. 1984, incorporated herein by reference, psychometric methods, see, for example, Kelly G A, The Psychology of Personal Constructs, Norton Press, New York, N.Y. 1955, incorporated herein by reference, and ethnographic methods, Suchman L A, Trigg R H, Understanding Practice: Video as a Medium for Reflection and Design, In: Greenbaum, J, Kyng M (eds), Design at Work: Cooperative Design of Compute Systems, Lawrence Earlbaum Associates 1991, pages 65-89, incorporated herein by reference.

Advantageously, the Computer-Based Testing System of the present invention has included a blend of these approaches. Direct questioning has been used in querying family practice physicians regarding their knowledge of and approaches to specific knowledge domains (such as osteoarthritis). Additionally, knowledge acquisition has included access to appropriate scientific literature, which functionally serves to provide an ethnographic assay of actual practice. Knowledge acquisition has also entailed protocol analysis, both in terms of analyzing specific physicians' problem solving methodologies and incorporating explicit clinical processes such as those presented in published clinical guidelines (a specific example here is the otitis media with effusion guideline developed by the Agency for Health Care Policy and Research).

To facilitate development of such a system, the present invention is divided into three components: the knowledge base, the patient simulation generator, and the presentation system. The knowledge base has been designed and represented as a series of entity-relationships. The model has several fundamental entities: Patient, Health States, Findings, Courses of Action, and Agents. These entities have relationships of INTERACTS_WITH, CONTACTS, IS_RELATED, EXHIBITS, HAS, EXPOSED_TO, LEADS_TO, ASSOC_WITH, LINKS_TO, USES, IDENTIFY, MANAGE, ALTER, REVEAL, and EVALUATE.

FIG. 1 describes an overall or conceptual view of the entities and relationships included in the model. Rectangles indicate entities between entities in the model. Hexagons indicate relationships. Solid lines indicate Medical Knowledge Relationships (e.g., a course of action such as treatment with non-steroidal anti-inflammatory agents can modify specific findings such as pain in the patient with osteoarthritis.) Dotted lines indicate Simulation/Evolution relationships which define how a particular domain simulation has proceeded.

The patient simulation generator of the present invention relies upon a series of generation methods to instantiate patients for presentation to the certification/recertification candidate. The processes function to evolve the patient forward (to reflect progression of the disease process and response to interventions) and backward in time (to create a past history for the patient.) To accomplish these tasks, the system utilizes processes for:
1. Content specification—these processes define the scope of the simulation
2. Patient generation:
   Past History ("backward" generation)
   Present and Future History ("forward" generation)
3. Simulation processes (in addition to patient generation):
   Interface processes (for presentation of the patient findings developed from generation processes.)
   Book-keeping processes (for keeping track of candidates' responses and patient evolution)

The patient generation process proceeds on the basis of a specific health state identifier (coded in the database as a name and SNOMED code) passed to the process at the start of the simulation. The SNOMED International structured vocabulary is a versatile nomenclature for describing medical ideas. See, for example, Côté R A, Rothwell D J, Palotay J L, Beckett R S, Brochu L, editors, SNOMED International: The systematized nomenclature of human and veterinary medicine, 3rd ed. Northfield, Ill., College of American Pathologists, 1993, incorporated herein by reference. This nomenclature allows one to make inferences from the codes used to represent each idea. For instance, the code F-37022 represents "retrosternal chest pain." The first character, "F," indicates that the code is from a broad class of ideas called functions. The next to digits, "37," indicate that the code involves a refinement of the code F-37000, "chest pain, not otherwise specified." Similarly, code F-37020 specifies "precordial chest pain." The code F-37022 implies that retrosternal chest pain is a kind of precordial chest pain, which is a kind of chest pain, which is a kind of function.

The generation process produces a complete patient description which reflects the EXHIBITS, HAS, INTERACTS-WITH, EXPOSED-TO, IS-RELATED, and CONTACTS relationships described earlier. These generated entity relations are stored as a collection of records referred to as the "White Board" data structures. The information in these records serves as input to the patient evolution process, which in turn evolves the patient's health status and medical/personal characteristics as a function of the passage of time or physician/examinee intervention.

The original patient generation process is generally called once at the session's start; the system calls the evolution processes repeatedly in response to time progression and physician action.

The first phase of patient generation entails development of the patient's history outline. This outline describes the series of health states and risk factors the patient experienced to reach the current health state, TS. To develop TS, the system first calls the procedure GenderRace, which establishes the patient's sex and racial/ethnic origin. Next, the system establishes the patient's age and age at onset through the OnsetAge procedure. The CreatePerson process then assigns the patient a birth date and name.

Once the patient's age, sex, racial/ethnic origin, and age at onset of the condition have been established, the OutlineFirstStep procedure defines the precursor states and risk factors which serve as the substrata for evolving the patient to the current time and target health state. The OutlineGeneralStep procedure is then called iteratively until the patient has arrived at the current TS. These processes are described in greater detail below.

Logical and procedural knowledge in the database described as "reasoning elements" (RE) (for example, Bayesian network describing a generation method, Bayesian network describing a treatment plan, and the like), included in the generation methods described above, "shape selectors" which describe distributions for the n patterns by which health states evolve (patterns in turn are specified by findings and subpatterns), and courses of action (COA) which represent possible further diagnostic and management strategies which candidates might select.

The patterns and subpatterns are represented as probability distributions (discrete and continuous as appropriate for particular finding) specified through the knowledge acquisition process. At the beginning of a simulation, random number generation is used to select a "master percentile" (MP) which then serves as the reference for selecting particular patterns, findings and subpatterns from the appropriate specified distributions. These selected patterns are queried to provide description of specific findings such as hyperglycemia in response to physician/examinee requests for information which are in the form of "courses of action" for a particular health state (e.g., hyperglycemia as a manifestation of diabetes.)

Once presented with the patient description (age, race, sex, clinical findings), the candidate then selects appropriate COA's for further evaluation and/or management of the patient's health state. Selection of an interventional COA invokes pattern modifiers which evolve the patient's health state by implementing shape modifiers. These modifiers act upon the initially selected health state patterns to redefine the patient's health state or findings (e.g., a COA of insulin administration would alter the hyperglycemic finding specified in the health state descriptions for diabetes mellitus.)

As mentioned earlier, COA's also include options for further testing/diagnostic procedures. For example, the candidate might choose to select a glycosylated hemoglobin evaluation; the COA process would access the pattern for glycosylated hemoglobin instantiated at the beginning of the simulation but which might not be reported unless specifically asked for by the candidate.

A COA can modify the health state in which a patient exists at one point in time. When the candidate selects such a COA, the simulated patient evolves to a new health state patterns associated with the new health state in the knowledge base. In order to avoid "state explosion", health states closely associated with each other are represented as parallel health states not as combined health state entities.

For example, the initially generated patient for a case of osteoarthritis might demonstrate mild osteoarthritis. However, other health states, such as obesity, might influence the progress of the patient's arthritis from mild to moderate or severe disease. To avoid combinatoric health state explosion, we have implemented a concept of parallel networks of health states. In this representation, a newly-generated patient will exhibit instantiated health state patterns for the primary domain (in this case osteoarthritis) and for the parallel health states (obesity in this example) which influence the primary health state's progress.

As shown in FIG. 2, osteoarthritis can progress over time from the normal state to mild, moderate or severe osteoarthritis. For this particular illness, progress occurs in one direction only; osteoarthritis does not regress once developed, but can stabilize at a particular degree of severity. Obesity represents a parallel health state which can influence the progression of osteoarthritis. Mild, moderate, and severe obesity can influence this progress at different rates: the model permits representation of greater impact for more severe obesity states. Notice also that obesity can regress (e.g., severe obesity can revert to moderate obesity, etc.).

Any one of a number of health states might exist which could progress independently of osteoarthritis. For example, the patient who has osteoarthritis will frequently utilize non-steroidal anti-inflammatory drugs (NSAID's) for treatment. These agents can improve the symptoms of osteoarthritis, but also impact on the parallel state of peptic ulcer disease. Treatment with NSAID's can induce an ulcer, which can then evolve either on the basis of physician/examinee intervention for it, and/or for the course and treatment for other parallel health states, and time with the course and treatment of osteoarthritis.

The computer based testing system's fidelity depends upon access to a rich representation of health state-specific knowledge. This knowledge consists, as described above, in more detail below. The template includes a NAME for the health state and an associated SNOMED code. The template also includes specific descriptions of the FINDINGS, PATTERNS and SUBPATTERNS for these FINDINGS. The patterns and subpatterns are stored as a series of time and value pairs. As an example of such patterns, consider the example of Reactive Airways Disease (RAD). One finding of interest is the prevalence of RAD as a function of age, sex, and race. The prevalence for this finding appears in the knowledge base as collection of graphs illustrating the population prevalence conditioned on age, sex and race. Likewise, data such as acute exacerbation rates are represented as event rate distributions. The subpatterns also include information describing how various treatment modalities will modify the exacerbation rate and other pertinent findings such as peak expiratory flow rates and symptoms such as shortness of breath.

The present invention provides a prototypical process for developing domain-specific knowledge. The template for each domain includes, for example, the following hierarchy:

HEALTH STATE: {name assigned by the knowledge donor, e.g., "Normal Airway Reactivity"}
SNOMED CODE: {appropriate SNOMED code}
PREVALENCE: {age-sex-race specific prevalence; represented as pattern}
INCIDENCE: {age-sex-race specific incidence; represented as pattern}
FINDING: {general name for set of findings, e.g., "Asthma Attack Frequency" in reactive airways disease}
Specific
Finding: {description of specific instance of a FINDING; e.g., for the FINDING of asthma attack frequency, one specific finding is "No Attacks", associated with "Normal Airway Reactivity"}

Each HEALTH STATE affects multiple FINDINGS, which in turn have Specific Findings appropriate for that FINDING in that HEALTH STATE. Data such as incidence, prevalence, and attack rates are represented as PATTERNS (graphical functions which support the patient generation simulation processes). The information is collected in paper template form, and then transferred into computer-readable format using, for example, any standard Knowledge Acquisition (KA) tool to enter the information into an object-oriented database.

The KA "front end" may be developed, for example, in the Visual Basic® and Visual C++® programming environments. Courses-of-Action (COA), such as further evaluation and/or management strategies, are entered using a standard editor that creates text files describing appropriate evaluation/management steps to support the simulation processes. The COA editor may also be designed under the Microsoft Visual environments mentioned earlier.

The knowledge acquisition step includes the following subcomponents:
A. Health state specification
B. Enumeration of FINDINGs for the health state, and agreement among the development team members
C. Population of templates with knowledge
D. Entry of health state knowledge into knowledge base using KA tool and/or direct high level pseudo-coding
E. Debugging, including generating multiple simulations, to test system stability/credibility
F. Validation including review of generated cases by representative groups of family physicians It is a feature and advantage of the present invention to: (1) allow testing at remote sites and convenient times; (2) uniformly test an expanded range of important family practice activities, with fewer questions on exotic problems; (3) adapt tests to examinees' responses or needs; and (4) create reasonable questions at test sites to simplify administrative, economic, and especially security issues.

It is another feature and advantage of the present invention to provide an approach that does not incur high maintenance costs and produces efficient and affordable scenarios for a computer-based testing system.

It is another feature and advantage of the present invention to provide a formal model of family medicine to achieve a relevant and realistic implementation of a computer based examination.

It is another feature and advantage of the present invention to provide an examination that does not require replacement with new questions in order to preserve security of the certification process.

It is another feature and advantage of the present invention to provide a computer based testing system that may measure problem-solving capabilities.

It is another feature and advantage of the present invention to provide a computer based testing system that relies upon a knowledge base of family practice which contains "patterns" and "subpatterns" which depict in probabilistic terms disease/condition incidence, prevalence, evolution over time, and response to interventions.

The present invention is based, in part, on our discovery that prior computer based testing systems suffer from various problems, including the problem that the clinical simulations are "hard-wired" in computer source code or static data structures which must be re-coded or reinstantiated for each new examination. Accordingly, in prior art computer based testing systems, once the simulation has been used widely, the examination contents are no longer secure, necessitating continuous cycles of new simulation development.

The present invention is also based, in part, on our realization that the computer based testing system needs to be capable of efficiently generating new patient cases for each candidate examined, and capable of effectively testing a candidate's problem-solving ability. We have discovered that the above may be accomplished using a knowledge base of family practice which contains "patterns" and "subpatterns" which depict in probabilistic terms disease/condition incidence, prevalence, evolution over time, and response to interventions.

To achieve the above features and advantages, as well as other features and advantages that will be apparent from the detailed description provided below, a computer implemented simulation and evaluation method simulates interventions to a patient by a user, and evaluates the interventions responsive to predetermined criteria and the interventions. The method includes defining a test area to evaluate the user on at least one predetermined criterion, selecting genetic information of the patient responsive to the test area, and generating a patient history responsive to the test area and the genetic information. The method also includes receiving at least one intervention input by the user, and evaluating the user responsive to the intervention and predetermined criteria.

In accordance with another embodiment of the invention, a computer system and computer readable tangible medium is provided that stores the process thereon, for execution by the computer.

In accordance with another embodiment of the invention, a computer readable tangible medium is provided that stores an object including the entity relationship model thereon, for execution by the computer.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

The above objects of the invention, together with other apparent objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter forming a part hereof, wherein like numerals refer to like elements throughout, and in which there is illustrated preferred embodiments of the invention.

NOTATIONS AND NOMENCLATURE

Figure 1:
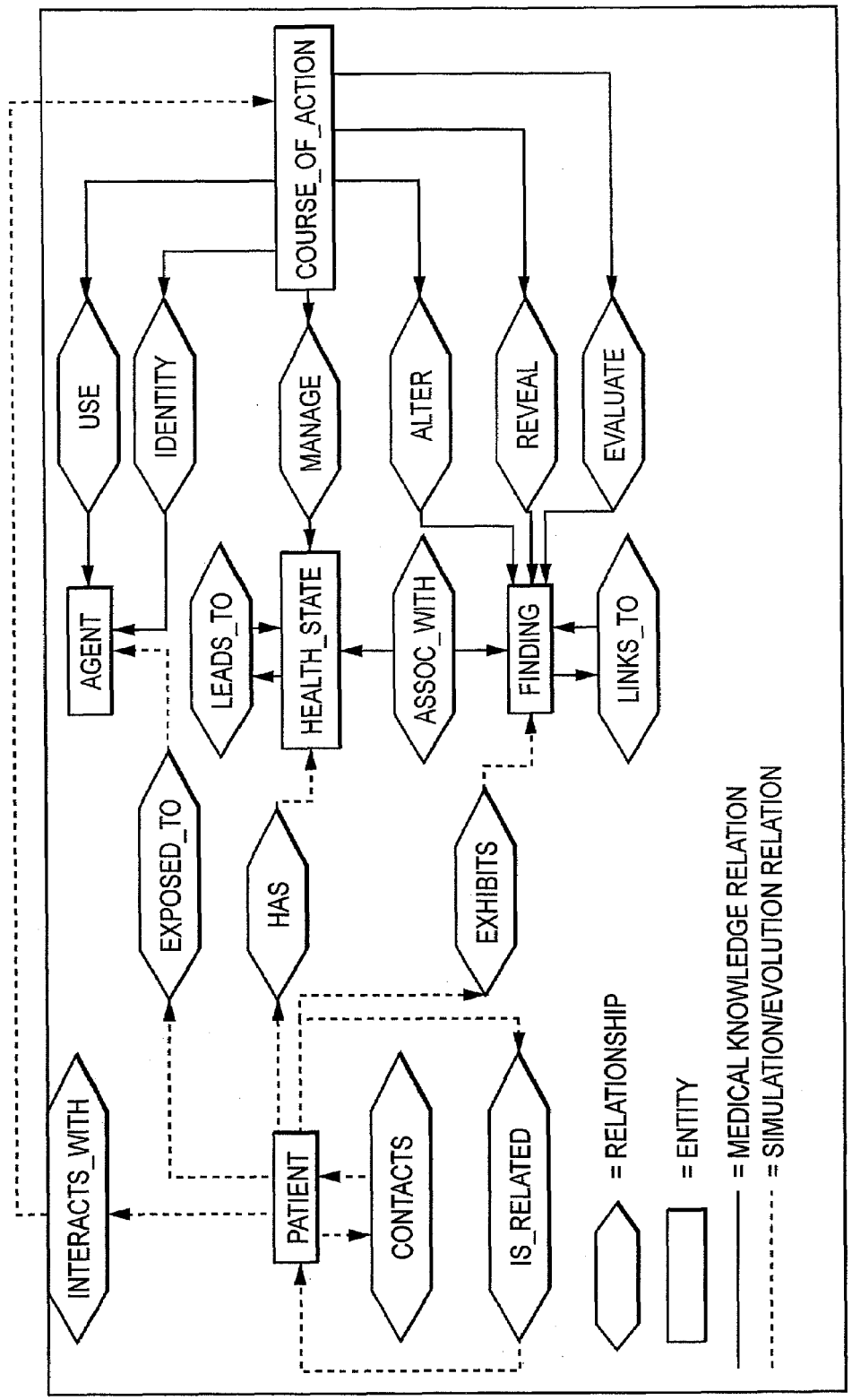
FIG. 1 is a diagram describing an overall or conceptual view of the entities and relationships in the model used in the computer based examination system of the present invention.
Figure 2:
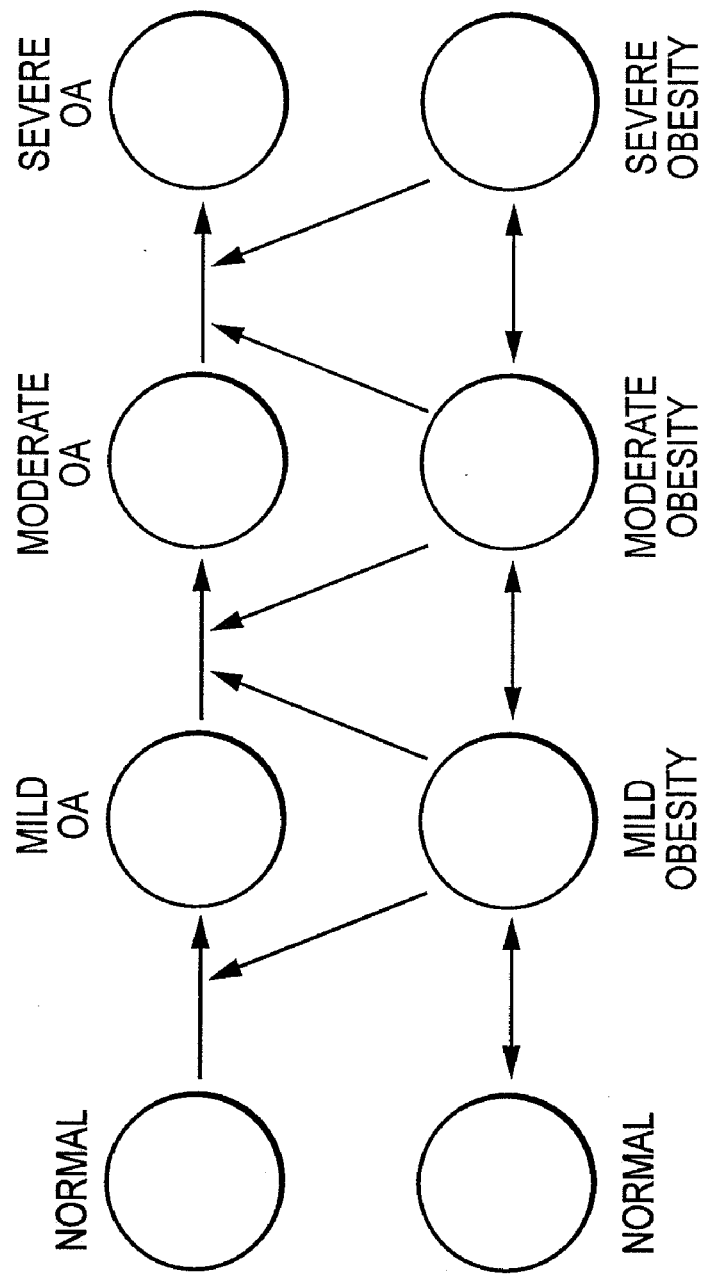
FIG. 2 is a diagram describing the progression of osteoarthritis over time from the normal state to mild, moderate or severe states of osteoarthritis.

The detailed descriptions which follow may be presented in terms of program procedures executed on a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices.

The present invention also relates to apparatus for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove more convenient to construct more specialized apparatus to perform the required method steps. The required structure for a variety of these machines will appear from the description given.

BEST MODE FOR CARRYING OUT THE INVENTION

The computer-based testing system described herein represents knowledge at multiple levels of complexity. The computer-based testing system of the present invention partitions knowledge into fundamental types: Health States, Agents, Findings, Specific Findings, Patterns and Sub-patterns describe system behaviors and characteristics. Courses-of-Action describe tasks and methods used to apply, modify, and evaluate the health state information and characteristics described in the model. Subdivision of knowledge types in this manner facilitates the knowledge acquisition process. This subdivision also promotes multiple levels of knowledge abstraction, which enhances the system's ability to represent varying levels of complexity.

For example, reactive airways disease is represented as a series of health states: Normal (Non-reactive) Airways, Reactive Airways-Mild, Reactive Airways-Moderate, and Reactive Airways-Severe. Each health state contains identifiers which relate the particular health state to precedents and antecedents (e.g., Normal Airways serves as the precursor health state for Mild Reactive airways disease, and Mild, Moderate and Severe Reactive Airways Disease represent target or sequential successor health states from the Normal circumstance.)

Each health state in turn has associated findings, and specific findings. For example, in the Normal Airways state, "Asthma Attack Frequency" appears as a Finding which is instantiated with the Specific Finding "No attacks." Similarly, other Findings such as Respiratory Function and Severe Asthma Attach Frequency are instantiated with corresponding normal Specific Findings (Normal Respiratory Functions, and No Severe Attacks.) This representation transports to each new health state in, what we have determined to be somewhat analogous to diagnosis.

Advantageously, the Computer-Based Testing System of the present invention in the knowledge acquisition process uses direct questioning in querying family practice physicians regarding their knowledge of and approaches to specific knowledge domains (such as osteoarthritis). Additionally, knowledge acquisition has included access to appropriate scientific literature, which functionally serves to provide an ethnographic assay of actual practice.

Overview of Testing/Recertification Process

The testing and/or recertification process, for example, unfolds as follows. After initial certification, examinees initiate recertification software on workstations on computer systems. The examinee begins recertifying at any convenient time and could suspend the examination at the conclusion of any simulated patient encounter. The software of the present invention presents a patient by using text, illustrations, still pictures, and video. The examinee questions and examines the simulated patient, reaches conclusions about the situation, and suggests treatment options. The simulated patient may express preferences about these options.

After receiving a treatment plan, the patient leaves, maybe follows the plan, and perhaps later returns for follow-up. In the meantime, the examinee sees other simulated patients. To discourage cheating, the software offers so many cases that a diplomate observing another examinee recertify gains little advantage with regard to test content.

The present invention maintains records of the information gathered, the hypotheses entertained, and the recommendations made for each patient. After monitoring performance on several similar cases (for instance, cases involving diagnosis and management of adult-onset diabetes mellitus), the program draws conclusions about the physician's ability to handle this class of problems. If competence has been demonstrated, the class of problems may be removed from further consideration for several years. Until competence has been demonstrated, the physician receives feed-back on specific areas for improvement and continues to see cases from this class of problems.

The testing and/or recertification process could eventually become a continuous learning experience at the office or home. Some recertification activities might qualify as continuing medical education, partially offsetting the time needed to recertify. Examinees could anticipate failure to recertify and take corrective measures years before actually failing.

The present invention provides an approach that does not incur high maintenance costs to maintain efficient and affordable examinations. The present invention also provides a formal model of family medicine to achieve a relevant and realistic implementation of this kind of computer-based examination.

In general, a model describes the kinds of information that could be collected regarding a topic. For instance, a model of a mailing address should include at least a name, street address, apartment number, city, state, and ZIP code. A database built upon this model could list these items for each entry. Not every item in the model should be described for every entry in the database; many addresses have no apartment number. Incomplete database entries still provide useful information; even if a street address is missing, the city to search can be found.

Finally, the model limits what the database could do; it could not easily list first names. A model of diagnostic medicine of the present invention includes diseases, historical and examination data, and links between diseases and data. These models represent knowledge that physicians apply to uncertain or imprecise cases. The address example suggests a list of simple observations, called a database. A diagnostic program uses a collection of more abstract information, such as a statistical summary of a database, to draw inferences about a single case. The program and its information are often called a knowledge base.

We have determined that a well-designed formal model supports automatically created case simulations, reducing the long-term cost of writing cases by hand and improving security. The formal model of the present invention considers that medicine is full of diagnostic complexities including disease interaction. Thus, diabetes could change the severity of pain experienced during an acute myocardial infarction. With this information, the knowledge base of the present invention is able to support a realistic simulation process—a simulated diabetic having an acute myocardial infarction will experience a specific discomfort. The present invention attempts to carefully define interactions for a number of health states that constitute the bulk of family medicine.

We have further determined that diagnosis and patient management are inextricably linked to time. Time receives relatively little attention in many knowledge bases and is often summarized very succinctly. For instance, a knowledge base might describe "chest pain lasting more than 30 minutes" as a symptom of acute myocardial infarction. This knowledge base could misinterpret 29 minutes of chest pain as evidence against acute myocardial infarction, and 2 years of chest pain as an indicator of acute myocardial infarction. The present invention also supports the related concepts of continuity of care and observation.

In addition to these problems, family physicians deal with a host of issues that we have determined are not routinely modeled in diagnostic software. Most of these issues reflect the overwhelming importance of patient management in family medicine.

First, family medicine occurs in a social context that is often ignored in computer-generated simulations. Knowledge bases do not model social interactions or family structure.

Second, family practice patients arrive with attitudes shaped by experience, and physicians must adjust their strategies to cope with those attitudes. Adjustments range from changing interview style to altering treatments. Variability in patient attitudes limits the likelihood that there exists one best answer for groups of patients with similar medical conditions.

Third, family physicians are not so much engaged in diagnosis as in helping patients improve the length and quality of their lines. Family physicians spend considerable time reassuring worried patients, alleviating symptoms, and preventing the onset or progression of disease.

We have determined that the final testing and/or recertification problem, evaluating the responses of diplomates, also requires a model of what family physicians do. All dichotomous evaluations, especially pass-fail tests, use arbitrary standards. The challenge is to set standards using generally agreeable and meaningful criteria. The present invention provides the flexibility to determine to whom the criteria should be agreeable—certainly to diplomates, but perhaps also to patients, insurers, or other customers. Specifying these customers will help establish meaningful criteria for certification decisions.

For instance, diplomates have an interest in maintaining respected credentials, patients want effective care, insurers desire low costs, and public health advocates have an interest in clinical guidelines. It is not at all clear how to respond to these diverse interests. The present invention delivers flexible models to describe the consequences of family practice activities, as seen by various parties, so that board certification remains a pertinent process regardless of changes in the health care system.

We have determined that a model is needed to describe the scope of family medicine in epidemiologic terms, while including the information about individual variation that differentiates individualized patient care from public health. The model will be the foundation of a family practice knowledge base storing data about family medicine. The model also supports other applications of benefit to family physicians. Specific software applications might involve medical records, structured vocabularies, medical reference tools, decision support systems, and continuing education programs.

Data structures to describe the activities of family physicians include a series of entity-relation diagrams. In an entity-relation diagram, entities usually represent things (nouns). The relations (verbs) illustrate how the entities interact. For instance, an entity-relation diagram of an address list might have an entity called "person," and an entity called "place," connected by a relation called "is at." One could read this diagram, "person is at place." The person entity would store people's names, the place entity would store addresses, and the "is at" relation would describe when and why this person is at that place. Thus, a person could now live at one place, previously live at another place, and continuously work at the first place. One person, two places, and three "is at" relations describe this address history. This address model is flexible and realistic.

We have determined that an important class of events exist in the model of family medicine, which we call "modifying relations," or modifiers. In database terms, modifiers are relations between traditional relations. Modifiers extend the conventional entity relation diagram and provide a means of managing statistically dependent events.

Model Structure

Figure 3:
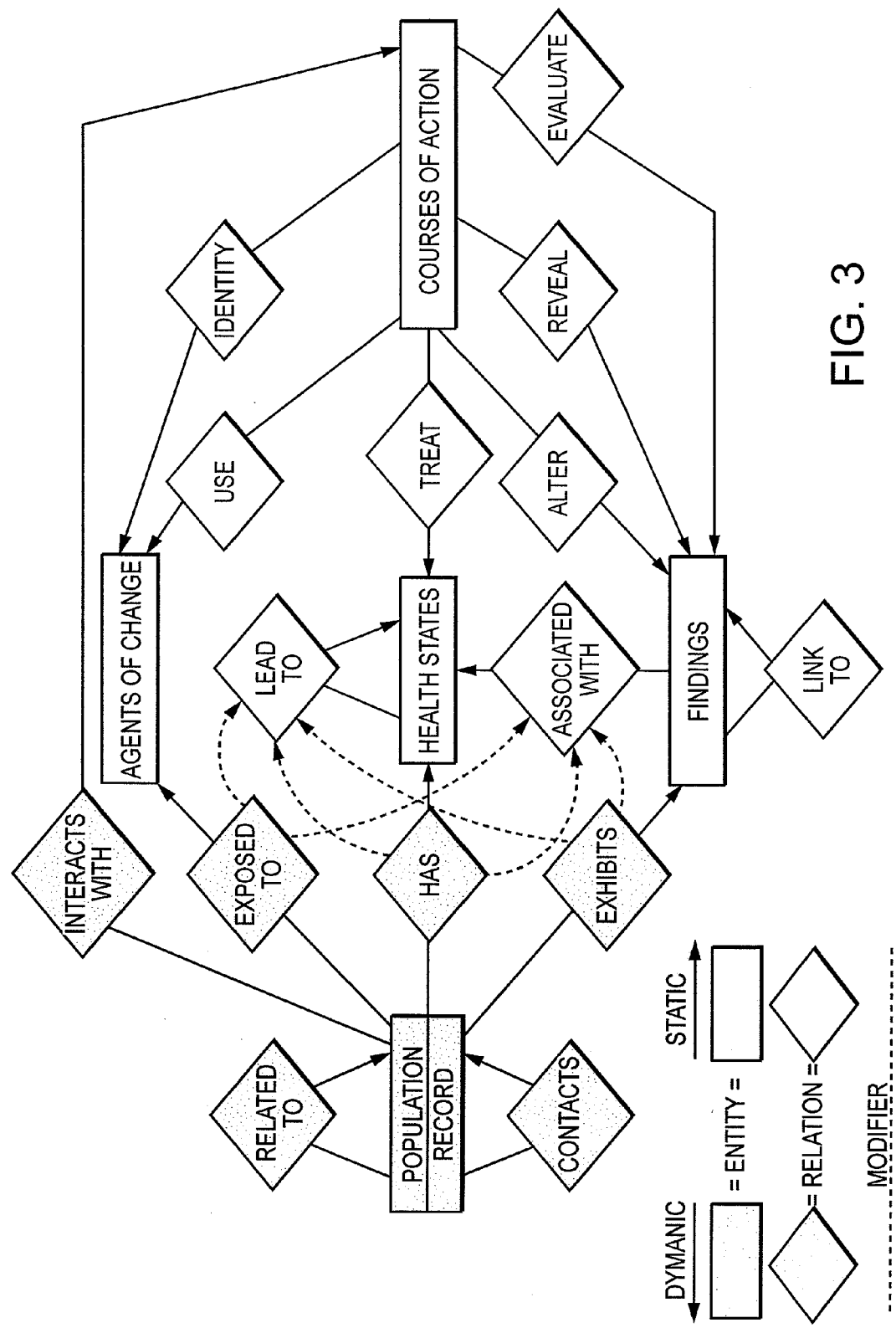
FIG. 3 is a detailed diagram of the family medicine model, including the major entities, relations and modifying relations.

The family medicine model includes the major entities, relations and modifying relations shown in detail FIG. 3. Formal concepts in the model are capitalized throughout the text. The model emphasizes diagnostic and management issues, variability in populations, and time. It describes consequences of anatomic and physiologic processes, but largely omits anatomic and physiologic reasoning as such. It is also capable of describing interpersonal relationships and is expendable to include an explicit representation of families or communities.

Modifiers (for example, Bayesian network from a Lead to relation, Bayesian network describing risk factors for progression, and the like) are relations that might change values in other relations. Dynamic entities and relations contain information relevant to patient simulations. Dynamic information for an individual patient is derived from data in other dynamic and static entities and relations. The dynamic Record entity has relations mirroring the Population's relations. Static entities and is relations contain the best available medical knowledge, similar to data in medical literature.

The following major entities appear in the design: Populations, Records, Health States, Findings, Courses of Action, and Agents of Change.

Populations represent real humans; their relations should precisely describe all data that physicians consider. Populations can be large groups with a shared characteristic, such as white males or single-parent families. An individual patient is a Population of 1; a pregnant woman is a Population of 2; a nuclear family with 2 children and 2 parents is a Population of 4.

Records model beliefs about people; a Record's relations summarize inferences about a Population. If a parent brings an infant to the office, this design represents the infant as a Population, the parent as another Population, and the parent's description of the infant as a Record. The physician can obtain historical information about the infant from two sources: the physician's medical Record of the infant, and the parent's Record of the infant. The physician can obtain current objective information by examining the infant as a Population. The data linked to Populations are absolutely precise, but can be observed, if at all, only during medical encounters. Records summarize the history of those real data imprecisely and potentially inaccurately.

Populations have Records of themselves, modeling a patient's self-image and memories. As with other Records, a patient's self-Record summarizes historical information with variable accuracy and might be the physician's only source of some historical information.

A Population is primarily a list of relations with other entities. A Record not only lists relations with other entities, but also defines encounters during which these relations were discovered. A Record can contain conflicting data acquired at different encounters.

Health States include all normal health states; classic disease presentations; early, subtle, or late disease presentations; and some disease combinations. Health States also include groups of Health States with shared characteristics, such as cardiovascular diseases and diseases of glucose intolerance. The SysteMetrics Corporation publishes Disease Staging Clinical Criteria, which define numerous stages in the development of diseases. See, for example, Gonella J S, Louis D Z, Gozum M E, editors, Disease staging clinical criteria, 4th ed. Ann Arbor, Mich.: MEDSTAT Systems, 1994, incorporated herein by reference.

Each of these stages represents a distinct Health State entity in this design. The SysteMetrics staging of diabetes mellitus defines stage 1.1 as asymptomatic diabetes, stage 1.2 as symptomatic diabetes, stage 1.3 as type I diabetes mellitus, and stage 2.1 as diabetes with end-organ damage. Each of these stages defines at least one Health State by the presence of specific objective criteria.

Stage 2.1 might be divided into a group of Health States representing each damaged end organ. To represent multiple end organ damage, one might simply superimpose these states.

Findings include genetic, physiologic, symptomatic, physical, and test-generated data, and clusters of such data. For instance, musculoskeletal chest pain could be a Finding. This Finding could be an example of a Finding called chest pains, which would represent all kinds of chest pains. Chest pains could be an example of a still larger Finding called symptoms. Findings are defined by a collection of one or more Features, whose current value can be described by a number on a scale. One Feature pertinent to pain is severity, which might be described on a 10-point scale.

Structures called Patterns describe the possible values of each Feature over time. A Pattern typically lists a series of values and corresponding percentiles at several points in time. Pediatric growth charts are the most widely used real example of Patterns. A blank growth chart illustrates at least the following observations: (1) Normal birth weights vary within a narrow range. (2) weight increases relatively rapidly in the first few months and years. (3) The absolute variation in weight (e.g., the difference between 90th and 10th percentile weights) increases after birth. (4) Most people reach a fairly constant weight by early adulthood. A pattern listing 10th and 90th percentile weights for people at age 0, 1 year, 2 years, and so on, illustrates the same concepts.

Growth charts also predict future values from past information. A child at the 50th percentile for weight now is expected to stay near the 50th percentile. If this child later reaches the 5th percentile of weight, the expected pattern is absent. The ensuing diagnostic evaluation is an effort to account for the deviation by finding a weight Pattern that explains all observations. These concepts extend easily to many other values, such as temperature. People have an average temperature of about 37° C., but some are a little cooler and some a little warmer. Normal temperature fluctuates within a narrow range during a lifetime, and most deviations from that range are considered abnormal.

Another example would be ST segments on a electrocardiogram. Following an acute myocardial infarction, ST segments usually rise by varying amounts, fall, and return to normal. The ST segment deviation from base line varies with time and can be described by a Pattern, similar to the variation in weights of growing children.

Many values change in predictable ways. Patterns might have cycles, sub-Patterns, and sub-sub-Patterns to describe these changes. The average value of a variable often changes during a lifetime, while the instantaneous value depends on a combination of annual, lunar, and circadian cycles. For instance, a nonpregnant 20-year-old woman should experience predictable lunar and circadian temperature fluctuations.

Sub-Patterns also describe consequences of other events, such as taking a drug. For instance, a dose of acetaminophen might lower a fever for 4 hours. A fever responsive to acetaminophen could be modeled by a high-temperature Pattern with a sub-Pattern indicating 4 hours of normal temperatures following acetaminophen doses. A person experiencing this fever and taking acetaminophen every 4 hours maintains a normal temperature. A physician observing this temperature Pattern would need to halt the acetaminophen to distinguish between a normal temperature and fever responsive to acetaminophen.

Sub-Patterns characterize Features and therefore Findings. For instance, one of the chest pain Findings might be "crushing substernal chest pain relieved by rest or nitroglycerin and exacerbated by exertion." This description implies a Finding with a designated location, a "crushing" Feature with some pattern, and 3 sub-Patterns describing the effect of rest, nitroglycerin, and exercise. The clinical appearance of simulated patients with this Finding might still vary, depending on the allowed variation in sub-patterns. For instance, pain might be more quickly relieved by nitroglycerin than rest or vice versa.

Finally, Patterns include Shape Selectors that help maintain consistency between variables. Shape Selectors are an example of Reasoning Elements, for example, small programs loosely based on the structure of Arden syntax medical logical modules. See, for example, Johansson B G. Wigertz O B, An Object oriented approach to interpret medical knowledge based on the Arden syntax, Proc Annu Symp Comput Appl Med Car, 1992, pages 52-56, incorporated herein by reference.

Reasoning Elements define variables; assign their values from data about the simulation; use loops, "if . . . then" statements, equations, and random numbers to reach conclusions; and finally produce some output. In Findings, the Shape Selector produces one percentile curve to represent the values of a Feature in an individual patient. For instance, although pediatric growth charts allow considerable variation in normal height and weight, one child will exhibit a precise series of values for both height and weight. Height will closely track one percentile curve, as will weight. The percentile of the height curve often limits the possible percentiles of the weight curve: healthy children at 95th percentile height rarely exhibit 5th percentile weight. Most children follow a weight percentile equal to the height percentile $\mp 20$. The weight Shape Selector can use this equation to restate the familiar height-weight growth chart.

Patterns model time and are one approach to interrelated medical observations. Time affects most numeric values in the model. Consequently, Patterns appear in nearly every entity and relation. Patterns describe the incidence of diseases at different ages, the likelihood of diseases progressing with time, and concentrations of drugs.

Courses of Action (COA) represent people's activities. Not only can these activities be medical, such as taking a blood pressure or performing a coronary artery bypass graft, but they can also include attending school, working, asking and answering questions, and following advice.

Populations invoke Courses of Action to decide when to visit a physician, how to answer questions, and whether to follow advice. Therefore, Courses of Action may advantageously be written to include missed appointments, lying to physicians, and ignoring physician advice. These actions could even depend on aspects of the physician's conduct, such as how the physician chooses to obtain information.

Courses of Action have complex internal structures. A Course of Action organizes Step, which gather, process, and modify information about Populations or Records. For example, a Step might be to obtain a blood pressure from a person. Each Step uses a Reasoning Element to accomplish its tasks. In the case of obtaining a blood pressure, the Reasoning Element would determine and report the simulated patient's systolic and diastolic blood pressure.

A group of Steps that can occur in any sequence is called a Batch. For example, when checking both right and left arm blood pressures, the order in which the arms are checked is probably unimportant, so these can be distinct Steps within a Batch. The Course of Action lists a series of Batches that must be executed in sequence, and describes any mandatory delays between Batches.

For example, to check orthostatic blood pressures, recumbent pressures would be obtained in one Batch. The patient would sit or stand in a second Batch. After a short mandatory delay, sitting or standing pressures would be obtained in a third Batch. Courses of Action also describe possible earnings, costs, pleasure, and discomfort that motivate people to seek or avoid activities.

Agents include physical, chemical, biological, behavioral, and social events capable of influencing health States or Findings. These Agents can be therapeutic, injurious, or both. Agent descriptions include data about intake, metabolism, and excretion, as applicable. For instance, a long-acting steroid is a chemical agent. Following intramuscular injection, the steroid will have predictable local and systemic concentration Patterns as the chemical dissipates from the injection site. The steroid might be metabolized to other compounds and excreted. Exposure to Agents normally occurs during a Course of Action, as this example illustrates.

The model of Agents describes their recognition, their presence, and the presence of metabolites or byproducts. Other parts of the model, such as the sub-Patterns of Findings, describe the effects of Agents.

Table 1 lists relations shown in FIG. 3. The Health States Lead to Health States relation describes how diseases evolve, and is therefore, critical for simulations. Preventive medicine scenarios might use this relation to generate patients who would benefit from screening. Case management problems can use this relation to model both the past and evolving history of a patient.

TABLE 1

| Relations Between Entities |
|---|
| Population Contacts Population |
| Population Related to Population |
| Population Interacts with Courses of Action |
| Population Exposed to Agents of Change |
| Population Has Health States |
| Population Exhibits Findings |
| Agents of Change Cause Health States |
| Health States Lead to Health States |
| Findings Associated with Health States |
| Findings Link to Findings |
| Course of Action use Agents of Change |
| Courses of Action Identify Agents of Change |
| Courses of Action Treat Health States |
| Courses of Action Alter Findings |
| Courses of Action Reveal Findings |
| Courses of Action Evaluate Findings |

Note:
These relations link entities in the model together.

Unlike traditional knowledge bases, this relation links Findings (with their Patterns) to a Health State, rather than linking a range of Finding values to a Health State. Sensitivity and specificity are represented as age dependent Patterns, rather than constants. The sensitivity of a Finding will be lower and the specificity higher in this model than in traditional knowledge bases.

The Findings Link to Findings relation describes causal associations between Finding Patterns, such as "severe cough causes abdominal muscle pain." This relation contains data about causality, mechanisms, and temporal constraints. This relation facilitates reasoning about Findings.

The Courses of Action Treat Health States relation illustrates means of curing Health States or preventing their progression. Treatments therefore modify probabilities in a lead to relation.

Courses of Action have three relations with Findings. The first, Alter, implies changing a Feature Pattern by invoking a sub-Pattern. For example, giving acetaminophen could alter a fever. The second relation, Reveal, links examining Courses of Action to the Findings they produce. For instance, a procedure called "taking a blood pressure" reveals systolic blood pressure. The third relation, Evaluate, links a Finding to a Course of Action that might be used to investigate its cause. This relation would link a Finding of systolic hypertension to a Course of Action describing its work-up.

The Population Contacts Population relation traces transmission of communicable Agents and potentially beliefs. Population Is Related to Population describes biological and social relations and the history of those relations, and traces transmission of genetic Agents. These two relations allow descriptions of arbitrarily defined families, with arbitrarily harmonious interactions.

The Population Interacts with Courses of Action relation describes why the Population began the Course of Action, what the Courses of Action cost interested parties, and how comfortable the Population was during the Courses of Action. This model allows a patient to remember an unpleasant experience and resist having it repeated. Because Courses of Action can include negative (buying a therapy) or positive (receiving a paycheck) change in wealth, this relation is also capable of being used to model patients' economic inability to follow medical advice.

The Population Exposed to Agents of Change relation describes perceptions about the exposure, knowledge of exposure, and the course of Action responsible for the exposure. This relation can describe exactly how an Agent was distributed in, metabolized by, and excreted from this Population.

The Population Has Health States relation includes the preceding Health State, a list of Findings attributable to the Health State, and the age at onset, diagnosis, and evolution of the Health State. Health States affect different individuals in different ways, and treatment often depends on the patient's impairments and perceptions. Consequently, a patient's beliefs about disease progression and perceptions of a Health State belong in the Has relation.

The Population Exhibits Findings relation has similar perception attributes. Perceptions can be divided into Dysutility and concern. Dysutility indicates a trade-off a patient would accept to return to normal. Concern indicates a trade-off a patient would accept for full reassurance that a Finding or Health State does not portend future Dysutility. For instance, a patient with a minor left-sided chest pain might rate its current Dysutility as $5 ("I would spend $5 to relieve this pain for today."), and the concern as $100 ("I would spend $100 for assurance that nothing serious caused this pain."). If the pain persists unchanged, both of these values might decline as the patient learns to cope with the discomfort and becomes confident that the symptom has no prognostic importance. Thus, patients can have changing attitudes about stable conditions. Patients would typically seek medical care when provoked to so by a Dysutility or concern.

Records have the same relations as Populations, except that the details are always more ambiguous, inaccurate, or both. For instance, a patient might have influenza starting December 15, while his Record of himself indicates that he developed influenza between December 10 and December 13. The patient's Record of himself is both ambiguous (there are 4 possible days of onset) and incorrect (none of the days is December 15).

We have further determined that the data described in the Lead to, Associated with, and Link to, relations often change with medical interventions or other events. Modifiers describe events that cause a permanent variation in the expected history of these relations. For instance, an event might make evolution to another Health State more or less likely (regular low-dose aspirin reduces the risk of acute myocardial infarction), or could permanently alter the likelihood of exhibiting a finding (cardiac transplant prohibits myocardial ischemic pain). The dashed lines in FIG. 3 show Modifiers. The following examples illustrate some modifiers (for example, Bayesian network from a Lead to relation, Bayesian network describing risk factors for progression, and the like).

Population Interacts with Courses of Action modifies Health States Lead to Health States. An appendectomy alters the progression of acute appendicitis to appendiceal rupture. For example, life-span-altering interventions always modify a Lead to relation.

Population Exhibits Findings can modify Health States Lead to Health States. For example, being overweight increases chances of developing a deep vein thrombosis or pulmonary embolism.

Population Has Health States can modify Health States Lead to Health States. Diabetes accelerates the onset of cardiovascular disease.

Population Has Health States can modify Findings Associated with Health States. Diabetic neuropathies diminish pain associated with myocardial infarction or extremity injuries.

Modifications of these relations account for many benefits ascribed to receiving medical care. Other benefits can occur when medical interventions temporarily decrease the severity of Findings.

The model described herein is intended to be a highly structured and realistic representation of family medicine that will guide the design of the family practice knowledge base and support the generation and evaluation of recertification examinations. In this model, the following are strong assumptions: (1) Health States are discrete and distinguishable on the basis of associated Findings, which are also discrete and distinguishable on the basis of the Patterns of their Features. (2) After choosing a percentile curve in a Pattern to represent some value, the percentile does not change substantially. (3) Changes in Patterns (e.g., the probability of one Health State evolving to another) can be described for important combinations of risk factors, interventions, and time of occurrence. (4) Transitions from one Pattern to another can be estimated by simple means. (5) Modifying relations do not have important interactions with one another. (6) Highly developed anatomic and physiologic models are not necessary, because associations between Findings provide the same information.

Although the model should have clear places to store nearly all interesting facts about family practice, test generation does not require a comprehensive description of all facts used in family practice. The proposed test generates plausible problems from a set of data intentionally skewed to generate interesting (i.e., discriminating) cases. The present invention provides the flexibility to avoid controversial questions by controlling skewed data. For instance, if the management of borderline diabetes is controversial, the present invention allows editing of the family practice knowledge base so that diabetics' fasting blood glucose levels are always markedly elevated. The family practice knowledge base would then be incapable of creating a borderline diabetic.

The diagram of the model illustrated in FIG. 3 reflects many family medicine concepts, and therefore, helps students, physicians and others understand the process at work in family medicine. For instance, the diagram illustrates that Populations have biological and social relations. Populations exist in Health States, which evolve into new, sometimes undesired Health States.

A major goal of family medicine is to retard or stop undesirable evolutions and promote desirable evolutions. Stopping one undesirable evolution could, however, result in a different undesirable evolution. In addition, physicians who treat symptoms will Alter Findings, but do not necessarily Treat Health States. Altering Findings usually changes current quality of life, whereas treating Health States usually changes future quality and quantity of life. Because Findings occur in the context of Health States, we have determined that physicians contemplate what Health States might be responsible for Findings, rather than Alter the Finding without considering future quality of life. The only tools available for these causes are Courses of Action. Physicians prescribe Courses of Action, but only patients Interact with Courses of Action. For example, the prescription does not guarantee that the patient follows the correct Course of Action. Agents (e.g., drugs) make a difference only when used in the context of a Course of Action.

The model's details provide further insights for students. First, time is an extremely important element of primary care. Patterns become more distinctive as time passes, simplifying diagnosis. The total risk of going from one Health State to another increases with time, increasing the value of early interventions. Second, patients have variable and evolving attitudes about Health States, Findings, and Courses of Action. The goal of medicine might not be to adhere to an endorsed Course of Action, but to optimize each patient's perception of his or her quality of life. To reach this goal, physicians adjust Courses of Action to accommodate individuals' attitudes. Third, the importance of time and attitude in optimizing the quality of a patient's lifetime suggests that continuity of care might help some patients.

The scope of family practice and the importance of protocols, time, individual variations and attitudes, and rationales distinguishes the content of the family practice knowledge base. That is, advantageously, some differential diagnosis of internally generated cases is possible using the model.

In this model, differential diagnosis largely depends on establishing the presence of Findings, which in turn depends on establishing the presence of Patterns and sub-Patterns of Features. Except in rare cases of pathognomonic values, confidence in the presence of a Pattern will increase with the passage of time.

We have also determined that the structure of an interface to medical reference systems might be enhanced using the model. Current reference systems use the structure of medical publications and lists of abstracted subject headings to facilitate searches through very large databases. These searches can yield large numbers of extraneous citations, especially for novice users.

The model suggests an alternative indexing strategy, as well as a graphical search interface. For instance, one could view a query interface similar to FIG. 3. To request a query about the effect of insulin treatment on the development of retinopathy in diabetic patients, one selects diabetes from an unrestricted list of Health States. The Lead to allows the user to select diabetic retinopathy from a list of diseases restricted to diabetic sequelae. The Modifier specifies which Course of Action or Agent of Change to consider. The computer delivers a list of references mentioning insulin in a diabetes Leads to diabetic retinopathy relation. Searching for a particular relation between two entities improves the efficiency of searches usually performed by naming the entities.

Overview of Patient Generation/Evolution Processes

Figure 4:
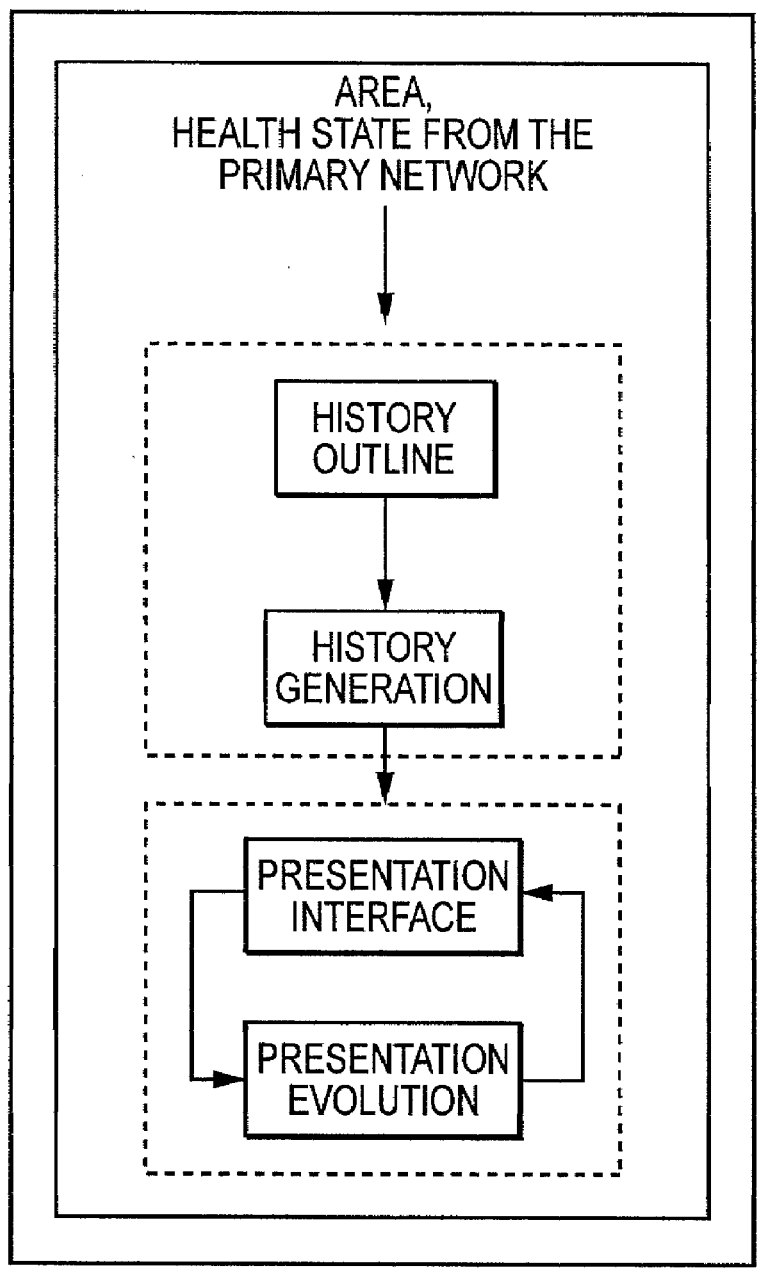
FIG. 4 is a flowchart of the overall process for the computer based examination system of the present invention.

We describe here an overview of processes used in the certification/recertification system. The processes are divided into four main groups:

1. Patient generation processes:
   history outline processes
   history generation processes 2. Simulation processes
   Presentation interface processes
   Patient evolution processes Patient generation processes are called once and produce the subject for the examination session. Simulation processes may be called repeatedly several times. The patient generation process presents the patient to the examinee, collect the examinee's responses and queries, and evolve the patient. See FIG. 4 for a pictorial overview of the system.

For the patient generation process, we assume that the area for the simulation—a specific object, say A, from the class AREA—and a health state, say H, from the primary network of the area A are given. For example, A may be the area of the adult onset diabetes and H may be the health state of symptomatic diabetes.

The patient generation process consists of two phases:
1. history outline, and
2. history generation.

The goal of the history outline phase is to generate a progression of health states and risk factors traversed by the patient on the way from the normal condition to the specified health state H. It starts with a call to the procedure that establishes sex and race of the patient being generated (referred to as procedure GenderRace). The next step establishes the age of onset of H (call to procedure OnsetAge).

The goal of the next step is to select the precursor state for the target state in the simulation as well as risk factors (circumstances) that will affect the patient under construction. This will be accomplished by a call to the procedure OutlineFirstStep.

Figure 5:
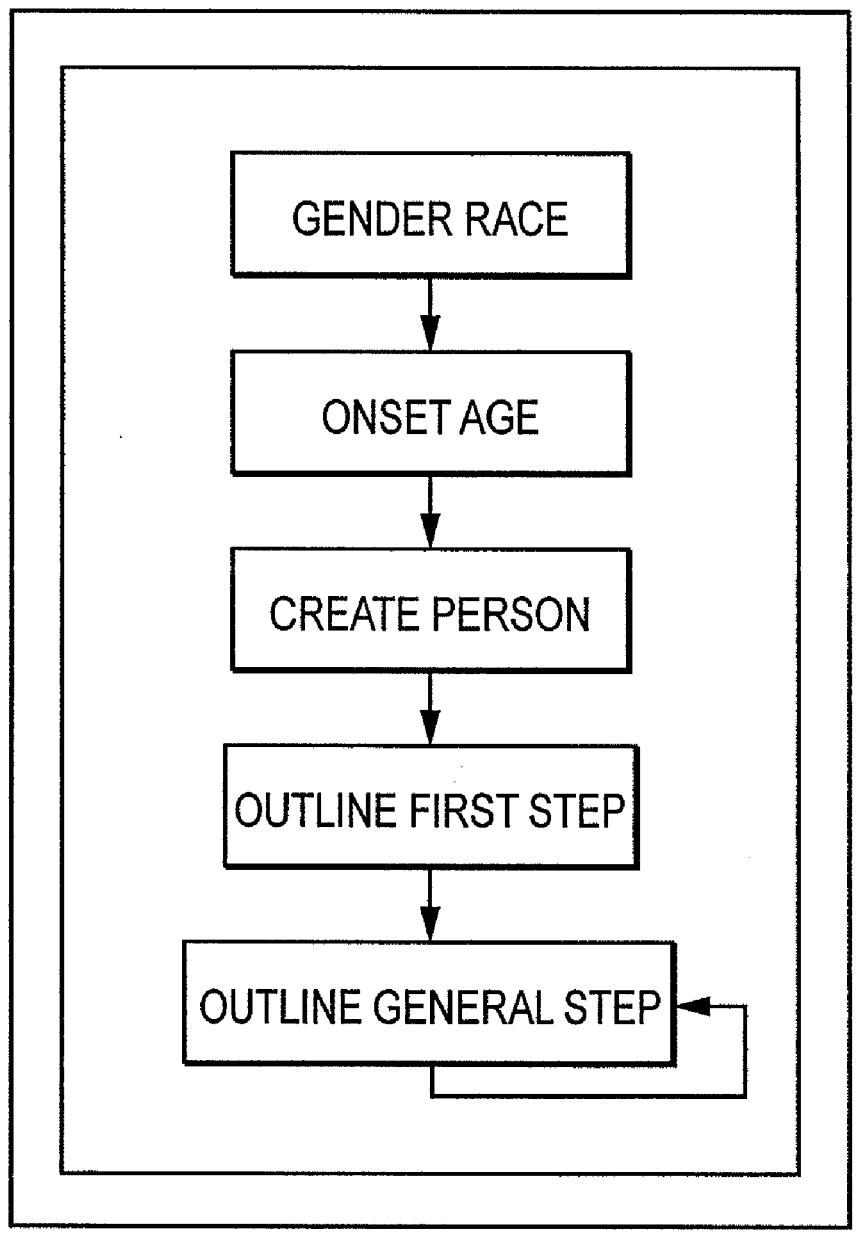
FIG. 5 is a flowchart of the history outline process which generates the patient history in the computer based examination system of the present invention.

The next procedure, OutlineGeneralStep, is called iteratively until the normal health state is reached. In each iteration, it finds the precursor health state as well as its onset time. When the normal health state is reached, the history outline phase is complete. See FIG. 5 for a flowchart of this process.

The GenderRace procedure generates sex and race of the patient under construction.

CreatePerson creates a basic description of the person. We select last, first and middle names, and age of the person, as well as two basic demographic findings: sex and race. These last data are stored as EXHIBITS tuples (since demographic findings are treated as findings).

The OutlineFirstStep procedure generates the precursor state for the target health state for the simulation, and its onset age. In addition, it selects circumstances to which the simulated patient has been subject. This procedure also creates an object HS_path, stored on the white board and containing the sequence of HAS instances for the precursors of TS, starting with the normal health state and ending with TS. This sequence will be used later in the history generation phase.

The Generating history outline, and more specifically, the OutlineGeneralStep procedure, generates the complete path of precursors of the target health state. It starts in the normal health state and terminates in the target health state TS (of course, the last but one state on the path has already been generated by OutlineFirstStep procedure).

History Generation

Figure 6:
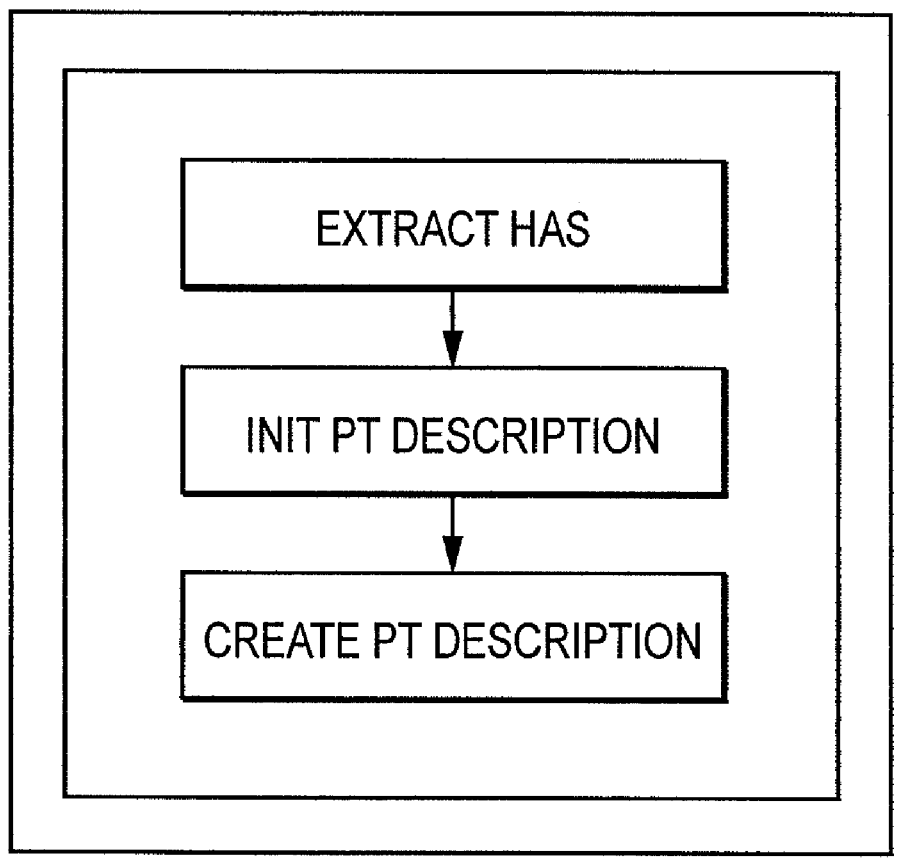
FIG. 6 is a flowchart of the history generation process which finds values for the patient history in the computer based examination system of the present invention.

The history generation phase finds values that are established in each case when they differ from normal (normal values are derived from the defaults maintained in the knowledge base). The general outline of this phase is given in FIG. 6.

The reasoning element, called generation method, describing how a given health state or a risk factor determines a finding, plays an important role in this phase. The generation method either provides a description of all relevant basic features at all relevant sites (for normal states), or determines which basic features at what sites need to be adjusted and by what specific findings. The main input for this phase is the list of associated objects attached to the object P of type PERSON (the object of the simulation).

The history generation process looks at all associated objects and modifies values of patterns describing relevant basic features so that the detailed description of the patient is consistent with the health state history as created in the earlier phase. Therefore, in this phase we focus on describing findings and their basic features. To this end, we look at all health states represented by HAS instances. We sort them according to their onset times. This results in a list in which all states normal in their areas precede all the abnormal states. The reason for this is that all normal states start at time 0. For each of these normal states we will run its generation method. This creates a list of finding names and site names to which the findings pertain, and defines the domain of all findings for which specific descriptions are created.

Next, for every finding, the patterns of its basic features are instantiated. We obtain these patterns from "normal" specific finding belonging to the finding in question. To select specific curves, we use a percentile value. This value will generally be selected from, for example, the range [0.15, 0.85] uniformly at random. Each time we need to use this value to select a specific pattern, we modify it, for example, by a randomly selected number from the range [−0.05,0.05]. In this fashion the modified value is, for example, in the range [0.10,0.90].

After all normal states are processed, patterns of all basic features of all relevant findings are instantiated for life. From now on, when processing other health states these patterns are modified. The idea is to run the generation method for a health state. As a result we get a list of sites and basic features which must be modified as well as specific findings where the new patterns can be found. If only some sites for the finding are generated, only those sites need to be modified. To modify the patterns, we use patterns captured by the appropriate specific finding. Again the basic percentile is varied and used in the selection. The selected pattern is then superimposed on the existing pattern (its values replace the old values starting with the onset age for the health state).

The generation method associated with the health state H, generates the list of relevant findings with additional information on sites and specific findings. That is, for each finding we maintain the list of sites and with each of those we associate the list of all basic features (names) corresponding to the finding. Finally, these basic features are described by their patterns.

The PatientDescription procedure selects HAS instances. It then arranges them according to onset times, generally earliest first. In this process, the procedure invokes the generation method procedures for each health state, thus creating EXHIBITS tuples describing findings associated with health states.

The InitPt Description (Initialize Patient Description) procedure initializes the list PATIENT FINDINGS, which contains all findings relevant to the primary health state as well as all secondary (modifying) health states. It creates all corresponding EXHIBITS instances and attaches them to the list associated_objects. All these findings are initialized to their normal values.

After the call to InitPtDescription, the domain of findings, sites and basic features, which subsequently will be modified, is defined. CreatePtDescription scans the list of HAS instances and adjusts findings so that the resulting patterns are consistent with the history of health states.

Patient Evolution

As explained earlier, we assume that data required by the processes is stored in the entity relationship model, white board (WB) and in the area of memory local to patient generation and evolution processes. This local memory will be denoted as LM. We start the evolution phase with the patient fully described and stored in the WB. An equivalent description exists in LM. Several HAS instances describe continuing health states (one of them—primary). After the assessment phase (requiring physical examination and history taking) the examinee proposes treatment consisting of one or more courses of action. These courses of action may alter some of the health states the patient is currently in. All selections made by the examinee are gathered in a table coa_list.

LEAD_TO data describes probabilistic information on progress from one health state to another. This data depends on modifiers. At present, we use a small generic set of modifiers: "fast progress", "moderate progress" and "slow progress". For each of these modifiers, and for an edge in the health state network between a precursor health state PS, and the target health state TS, the entity relationship model contains an estimate of the flow along that edge.

Courses of action are represented in WB by a table which describes their structure in terms of elementary courses of action. We will describe this structure below. In addition, each course of action contains a reasoning element. This reasoning element, given an edge (a pair (PS,TS)) and a set of other current health states (as modifying events), computes one of these three modifiers. Flows on the edges starting in the current health state are used in the selection process. Once the selection is made, duration risk stored in the appropriate LEAD_TO tuple is used to determine the onset time for the selected health state.

The following structure is used to represent a course of action COA in WB. The data is stored in a table with, for example, four columns (additional columns may be necessary later for evaluation purposes). The first column is labeled ECOA (elementary course of action). It lists all concrete elementary courses of action that might be used in a construction of COA. The second column describes the type of the corresponding elementary course of action. ECOAs of the same type are identified by the same integer in the second column. The third column contains one of five boolean operators: none (NOR), single (XOR), at least one (OR), some but not all (NAND), all (AND). All members of a type are assigned the same operator in column 3. The fourth column contains weights which are used in the matching process.

One of the courses of action listed with every health state is called TIME. It describes the effects of no specific action by the examinee and serves as a default course of action.

The evolution phase is accomplished by the procedure called Evolve. Evolve has three input parameters: patient P, patient's age T and the list coa_list of COAs selected by the examinee. Evolve starts by creating the list of patient P continuing health states. This is accomplished by the procedure called SelectPresentHas. SelectPresentHas selects from the list of P associated objects those HAS instances that represent continuing health states. It arranges selected HAS instances in a list.

For each health state PS described by the list of selected HAS instances, we then identify in all the courses of action that are relevant to PS. It gathers all those courses of action that are in relation MANAGE with the health state PS, in the list called, for example, coas.

At this time, the closest COA, among those found relevant to PS, to the examinee selection (described, recall, by the list coa_list) is chosen. For the course of action, say COA, target states are created for PS, corresponding modifiers and flows. This data is used for evolution.

These steps are repeated for each health state PS. When the process is completed, all successor health states are represented by means of the corresponding HAS instances. The evolution step is completed with a call to CreateDescription procedure. It generates descriptions of specific findings corresponding to the health states.

Stochastic Process for Patient History Generation

The present invention provides a method to automated authoring of major events in simulated medical histories. We have designed a knowledge base with temporal descriptions of the incidence and prevalence of health conditions and plausible intervals between health conditions. Each health condition is part of a small sequence of related and mutually exclusive health conditions. Many of these small networks exist in parallel.

We have determined that a patient's overall health can be described by a vector indicating the patient's current health condition in each network. A patient's location in one network often affects timing of transitions in other networks. The knowledge base advantageously uses modifiers (for example, Bayesian network from a Lead to relation, Bayesian network describing risk factors for progression, and the like) to describe the influence of these and other risk factors, as well as interventions, on incidence and transition times. A stochastic history outlining algorithm uses these data to construct a lifetime and recent medical history whereby a patient might develop a specified vector of health conditions.

The present invention generates a large number of plausible history outlines. The present invention automates the authoring of major events in the lives of simulated patients. The present invention applies a Monte Carlo process to multiple stochastic trees, to generate large numbers of plausible case outlines. Further automated embellishment of these outlines yields complete, usable simulated case histories.

Previous efforts to simulate patients from data have used sensitivity information stored in a diagnostic database, or Quick Medical Reference, to stochastically create a description of findings in a patient with a disease. See, for example, Bergeron B. Iliad: A Diagnostic Consultant and Patient Simulator, MD Computing 1991, Vol. 8, pages 46-53; Miller R A, Masarie F E, Myers J D, "Quick Medical Reference (QMR)" for diagnostic assurance, MD Computing 1986, Vol. 5, pages 34-49, incorporated herein by reference. However, we have determined that these simulations lack rich historical details and may generate implausible combinations of events. See, for example, Sumner W., A review of Iliad and QMR for primary care providers, Archives of Family Medicine 1993, Vol. 2, pages 87-95, incorporated herein by reference.

Some simulations generate patient details from a complete and precise mathematical model of pathophysiology. See, for example, Valdivia T D, Hotchkiss J. Crooke P, Marini J., Simulating the clinical care of patients: A comprehensive mathematical model of human pathophysiology, Proc 19th Annu Symp Comput Appl Med Care. 1995, page 1015, incorporated herein by reference. This elegant approach is feasible in intensive medical care and some restricted organ systems, but primary care problems are not so well understood at present, and therefore require empirical description.

Accordingly, we have also developed a process for generating detailed patient histories culminating in a specified set of simulated health problems. The first segment of the algorithm creates an outline of the medically important events in a patient's life, including the patient's age at the onset and termination of different health conditions or exposures to biologically active agents. The second segment of the algorithm yields a detailed description of continuously defined facts about the patient, such as physical and chemical characteristics, morphology, function, and sensations throughout life.

The history outlining algorithm essentially creates paths through temporally reversed Monte-Carlo processes, casting major events in a patient's history while guaranteeing that the history ends with specified medical conditions. See generally, Rubinstein R Y, Simulation and the Monte Carlo Method, New York, N.Y., John Wiley and Sons Inc.; 1981, incorporated herein by reference. This process is applied to a set of stochastic disease history models, each describing the evolution of one health problem.

A knowledge base stores these models, along with standard modifiers that calculate temporal constraints on disease progression, conditioned on comorbidities and treatments. This algorithm is capable of generating many plausible cases in a short period of time preceding an examination.

The "Health condition Leads To Health condition" cycle is the central component in the generation of a patient history. A health condition is a named collection of facts, which usually have prognostic implications. Typically, the facts that connote a health condition have a specified degree of variation from normal ranges, and are thought to arise from a common underlying cause. A health condition can usually be considered to be located at one or more body structures where that underlying cause is present.

Health conditions uses patterns and subpatterns to predict their prevalence and incidence, conditioned on factors such as sex and race. Prevalence and incidence are provided in a widely used structure called shape, which plots a value over time. In this situation, time indicates the simulated patient's age.

A health condition uses a generation method reasoning element to establish the facts pertaining to its instantiation. These facts may include events like drinking alcohol or driving cars, but most facts are specific instantiations of more generic medical concepts, such as symptoms or laboratory values, in specified body parts. For instance, the generic concept of "synovial fluid glucose level" might be instantiated as "normal" in "both knees." Shapes describe exactly how a value in this instantiation may reasonably evolve or fluctuate over time.

Two special classes of health conditions exist. First, normal health conditions are incident only at birth (or conception, depending on testing goals). Second, "Alive" is a health condition whose prevalence shows the proportion of a cohort that survives to any age. The age specific prevalence and incidence of all other health conditions are defined as the percentage of living individuals at that age who experience or acquire the condition, respectively.

The leads to relation connects one health condition (the precursor) to another (the target), and describes possible time intervals required for evolution from the precursor to the target. A Pattern describes a probability density function (pdf) of these time intervals, conditioned on comorbidities, treatments, and other risk factors. This duration pdf provides a time constraint mechanism. For instance, a duration pdf for the progression of mild to moderate knee osteoarthritis, given obesity, might indicate a probability density of zero in the first five years following the onset of mild osteoarthritis, a uniform probability density from year five to year twenty, and then a probability of zero. This implies that all simulated obese patients develop moderate osteoarthritis between five and twenty years after the onset of mild osteoarthritis, and forbids simulated onsets at other times.

The modifiers of a Lead to relation also provide time constraints for risk factors. This allows the model to represent the concept that obesity must exist for a period of at least 10 and up to 40 years for this duration pdf to apply.

Finally, the Lead to relation provides information about how quickly and completely to convert from the findings typical of the precursor to findings typical of the target. For instance, if each knee osteoarthritis stage is a health condition, and each stage has a typical degree of joint space narrowing, then the transition from one stage to another should be accompanied by more narrowing of the joint space. The Lead to relation can indicate that this narrowing occurs over years, and that the narrowing is nearly complete when the simulation asserts that the latter osteoarthritis stage is present.

A series of Lead to relations connect health conditions into small networks illustrating evolutionary sequences of events. These networks often suggest a disease staging scheme, such as (Stage 0) No Knee Osteoarthritis, (Stage 1) Mild Knee Osteoarthritis, (Stage 2) Moderate Knee Osteoarthritis, and (Stage 3) Severe Knee Osteoarthritis.

We call this sequence a parallel health condition network. It is "parallel" to many other networks of health conditions that exist simultaneously in a person. In general, a parallel health condition network lists transitions that occur among an exhaustive set of mutually exclusive health conditions occurring in one body part. For instance, the left knee of a patient exists in one of the health conditions in the osteoarthritis network. The right knee also exists in one of these conditions, but not necessarily the same condition found in the left knee. The patient simultaneously exists with one condition in a gastric ulcer network, a weight network, and numerous other networks.

A simulated patient's overall medical condition is therefore a vector, V, listing the current health condition from each parallel network at each involved site. A case specifies vector $V_0$, indicating the health conditions instantiated at the initial presentation of a simulated patient, and sufficient information to create a history of vectors culminating in $V_0$.

Most of the parallel networks in any given case are inactive. These define an initial, usually normal, (stage 0) condition of the parallel network. Most cases contain a few active parallel networks. Active networks presenting at stage 1 or higher represent active medical problems. Active networks presenting at stage 0 represent potential problems, such as complications resulting from an active problem or its treatment. The examinee's task is generally to identify and respond to active networks in advanced stages, while minimizing disease progression in active networks at stage 0.

Active networks can be divided into two categories. A case usually focuses on care for a primary network "P" (for instance, osteoarthritis of the knees). A comorbid network "C" usually includes health conditions that influence, or are influenced by, the stage of evolution of a primary network. For instance, obesity is a risk factor for osteoarthritis, and osteoarthritis may worsen obesity by limiting exercise. Comorbid networks that do not interact with the primary network in any important manner may serve as distractors.

For instance, an episode of urethritis might be irrelevant to osteoarthritis, but suggests Reiter's syndrome as an alternative explanation for knee pain with an effusion. An active, stage 0 comorbid network provides opportunities for complications. For instance, a simulated osteoarthritis patient presenting with a "No gastric ulcer" health condition could advance to "Gastric ulcer" after receiving steroidal nonsteroidal anti-inflammatory drugs.

When an active parallel network describes a chronic condition, acute exacerbations may be expected with some of the health conditions in the network. An exacerbation network "E" is a parallel network describing acute flares of illness that occur during a more chronic health condition. For instance, flares of knee pain with effusions may occur in patients with chronic osteoarthritis. In principle, health conditions within an exacerbation network can have their own exacerbations. The simulation process of the present invention allows exacerbation networks to contain cycles, unlike primary and comorbid networks.

A simulated patient's medical history is the sum of the events culminating in the case defining vector, $V_0$. The case provides sufficient information to create many plausible histories, but does not store histories per se. Consider a case defined to culminate in severe bilateral knee osteoarthritis and morbid obesity. The relative sequence of events on the primary and comorbid networks are not necessarily constrained. Obesity might be required to occur before the onset of mild osteoarthritis. However, the onset of morbid obesity could occur before or after the onset of moderate osteoarthritis.

The cartesian product of two active, linear parallel health condition networks, P and C, yields a two dimensional web of health condition combinations. This produce re-establishes the complexity avoided by the parallel network simplification, and calls attention to interactions between P and C. A vertex in this web is composed of the ith health condition in P and the jth health condition in C, and is represented by the vector $V_0=(P_i, C_j)$. Evolution can be assumed to occur in only one dimension at a time. If evolution in both networks can occur simultaneously in life, one can be assumed to occur first, and the other a moment later for purposes of the model. That is, the set of vectors $V_{-1}=\{(P_{i-1}, C_j)\}; (P_i, C_{j-1})\}$ are immediate precursors of vector $V_0$, but $(P_{i-1}, C_{j-1})$ is not. Similarly, the set of vectors $V_{-2}$ includes $(P_{i-2}, C_j)$, $(P_{i-1}, C_{j-1})$, and $(P_i, C_{j-2})$.

Three kinds of interaction are possible in the web formed by networks P and C. First, the networks may be completely independent, so that evolution along one dimension has no implications for evolution in the other. Second, progression through one network may depend on the concurrent condition of an independent network. For instance, the incidence of early osteoarthritis conditions is dependent on the presence of obesity. Finally, mutually dependent networks create a web in which progression through each network depends on the concurrent condition of the other network. For instance, a realistic simulation of a severe osteoarthritis history might require modeling a "vicious cycle" where obesity accelerates osteoarthritis, which in turn accelerates obesity.

The cartesian product of N parallel health condition networks similarly yields an n-dimensional web of health condition combinations, with potentially complex interactions. Data acquisition for these webs is a daunting task, but might be simplified by (1) limiting the number of dimensions, (2) ignoring improbable health condition combinations, particularly when describing vicious cycles, and (3) assuming independence for some kinds of test cases even when dependence exists in reality.

Stochastic Process History Outlining Process

The goal is to produce patient care scenarios for recertifying diplomates to manage. The data described above allow automatic generation of such cases, starting from a case specification. The case is composed of primary network P, and comorbid health condition network C. Network P is composed of health conditions $P_0, \ldots P_n$ and "lead to" relations $PL_{0 \to 1}, \ldots PL_{n-1 \to n}$. Network C is composed of health conditions $C_0, \ldots C_m$ and "lead to" relations $CL_{0 \to 1}, \ldots CL_{m-1 \to m}$.

Chronic health condition $P_j$ in network P has acute flares described by parallel network E. Network E is composed of conditions $E_0, \ldots E_q$ and "lead to" relations $EL_{0 \to 1}, EL_{1 \to 0}, \ldots EL_{q-1 \to q}, EL_{q \to q-1}$. The normal condition of network E is $E_0$, and the network may cycle through $E_0$ up to X times.

The vector $V_o = (P_i, C_j, E_k)$ summarizes the health conditions required at the presentation of the case. Health conditions $P_i$ and $E_k$ may be incident or prevalent at presentation. Incident health conditions would typically require both diagnosis and management, while prevalent health conditions would often be known diagnoses, and require only management decision. Health condition $C_j$ is usually prevalent.

The first step assigns the sex, race, and other genetically determined facts to the prospective patient. If $P_i$ is an incident health condition in the simulation, the incidence pattern for health condition $P_i$, is conditioned on sex and race. Sex and race are assigned by obtaining the area under the incidence curves for male and female patients of each race. The simulator makes a weighted random selection of the patient's sex on the basis of the results.

In the weighted random selection process, a series of positive values is normalized to one by dividing each value in the series by the sum of the series. The resulting series defines a probability distribution. To select an item according to this probability distribution, the interval from zero to one is divided into consecutive subintervals of lengths equal to the corresponding probability the series. A random number from zero to one is generated from the uniform distribution. The interval to which it belongs defines the selected item.

Because the incidence or prevalence of some illnesses, such as knee osteoarthritis, can increase dramatically with age, some correction to approximate the absolute number of cases occurring at each age may be useful, depending on the goals of the simulation. To obtain absolute numbers of incident or prevalent cases at each age in a cohort, the incidence or prevalence at each age is multiplied by the fraction of the cohort in that age interval. Formula 1 illustrates this calculation, and the general procedure for multiplying two shapes.

Formula 1. Absolute prevalence of health conditions as a function of age:

$$\text{Absolute prevalence}(P_i, n) = \text{prevalence}(P_i, n) * \text{prevalence}(\text{Alive}, n)$$

Where prevalence (health condition, n)=the prevalence of health condition at age n years.

Similarly, the joint absolute prevalence of $P_i$ and $C_j$ can be calculated by multiplying the absolute prevalence of $P_i$ by the prevalence of $C_j$ in each age interval although the prevalence of either or both health conditions may be explicitly conditioned on the presence of the other, knowledge acquisition efforts are unlikely to capture such dependencies. Calculating the joint prevalence reduces the chance of creating an unsolvable history, for instance by creating a prevalent case of $P_i$ at an age where $C_j$ does not exist, regardless of the prevalence produced in knowledge acquisition. A weighted random selection of an age of presentation can be made from the product of the age specific prevalence of all representing health conditions, and the special condition "Alive.".

Often, either $P_i$ or $E_k$ is an incident health condition, and the age of onset of the presenting health condition vector, $V_0 = (P_i, C_j, E_k)$, is determined by the preceding step. In addition, the immediately preceding health condition vector, $V_{-1}$, must be $(P_{i-1}, C_j, E_k)$ if $P_i$ is incident, because any other vector would make $P_i$ prevalent rather than incident at age N. More commonly, $E_k$ is incident and vector $V_{-1}$ must be $(P_i, C_j, E_{k-1})$. Alternatively, if $V_0$ consist only of $P_i$ prevalent health conditions, then the age of onset of $V_0$ is unknown. In general, health condition vectors contain a mixture of conditions with known ending times (e.g., precursors of incident conditions in $V_0$) and unknown ending times (e.g., prevalent conditions in $V_o$).

Assume that $P_i$ is an incident health condition at age N. The interesting vector is therefore $V_{-1} = (P_{i-1}, C_j, E_k)$, because health condition $P_{i-1}$ evolved to $P_i$ at age N. One possible precursor of vector $V_{-1}$ is $(P_{i-2}, C_j, E_k)$ which would evolve to vector $V_{-1}$ at the age of onset of health condition $P_{i-1}$.

The age of onset of $P_{i-1}$ is constrained in part by the age specific incidence of $P_{i-1}$, and N. The incidence of health condition $P_{i-1}$, conditioned on race and sex yields the number of new cases per year per number of persons at risk, in each year from birth to age N. Because the simulated patient must belong to a cohort of individuals who lived until age N, corrections to obtain an absolute incidence are usually not important.

The age of onset of health condition $P_{i-1}$ is further constrained by the plausible duration of $P_{i-1}$. For instance, if $P_{i-1}$ always progresses to $P_i$ within ten years, then a case of $P_{i-1}$ must have begun between ages (N−10) and N. The "lead to" relation $PL_{i-1 > i}$ provides a duration pdf, conditioned on pertinent facts representing some known modifier. The duration pdf is a probability distribution function defining probabilities of evolution to $P_i$ time intervals subsequent to the development of $P_{i-1}$. The duration pdf is truncated at the time equivalent to the age of presentation, N (assuming that $P_i$ could not have begun before birth), and reversed in time. The reversed duration pdf indicates at age 0 the probability that a transition from $P_{i-1}$ to $P_i$ would take N years, the simulated patient's entire life. In the year before presentation, at age N−1, the reversed duration pdf shows the probability that the transition would occur after exactly one year.

For each year from birth to the age of onset of $P_i$, the incidence of health condition $P_{i-1}$ and the reversed duration pdf are multiplied to obtain a weighting factor for the onset of P in that year. These weights are used to make a random weighted selection of one year to propose as the age of onset for the health condition $P_{i-1}$. This age represents one proposal for the age of onset of $V_{-1} = (P_i, C_j, E_k)$.

Formula 2. Weight ($W_n$) for establishing the onset of health condition $P_{i-1}$ at age n:

$$W_n = \text{Incidence}(P_{i-1}, n) * \text{DurationPDF}(P_{i-1}, N-n)$$

Where:
N=age of onset of health condition $P_i$ DurationPDF (health condition, x)=probability that health condition evolves to its successor during the time interval x−1 to x years after its onset.

In general, this procedure is repeated for each health condition with an onset time after birth (or conception) in the currently interesting vector, $V_{-1}$. The result is a proposed list of ages of onset for a subset of vectors in the set $V_{-2}$. The next step proposes ages of onset for the remaining vector in $V_{-2}$.

Assume that health condition $C_j$ is a prevalent condition in a simulated patient presenting at age N. Assume that the annual incidence of $C_j$ is constant from age N−3 to N, and that $C_j$ is equally likely to evolve to $C_{j+1}$ in 1, 2, or 3 years. The duration pdf from the "lead to" relation $CL_{j \to j+1}$ is therefore uniform over years 0 to 3. Consequently, $C_j$ beginning at age N−3 is as likely to continue to age N−2 as to age N−1, but will not be prevalent at age N in either case. Conversely, most cases of $C_j$ beginning at age N−1 would be prevalent at age N. To accommodate the uncertainty regarding the onset time of $C_{j+1}$, the duration pdf is reversed in time (as in the previous step), then converted to a cumulative probability function. The highest cumulative probability occurs just before the age of presentation.

Formula 3. Reversed cumulative probability (RCP) of duration of health condition $C_j$:

$$RCP(n) = \sum_{y=0 \text{ to } n} (DurationPDF(CL_{j \to j+1}, N - y))$$

Where:
N=age at presentation
y=a number of years between 0 and n.

For each year from birth to the age of presentation, the incidence and reversed cumulative probability of duration are multiplied to obtain a weighting factor for the onset of $C_j$ in that year, a random weighted selection chooses the year to propose as the age of onset for the health condition $C_j$. This age represents a second proposal for the age of onset of $(P_i 1, C_j, E_k)$.

Formula 4. Weight ($W_n$ for selecting age n for the onset of health condition $C_j$:

$$W_n = \text{Incidence}(C_j, n) * RCP(n)$$

At this point, the simulator has completed these steps. It found vector $V_0$ to have a single possible predecessor, $V_{-1}$. Each health condition listed in $V_{-1}$ could have been the last to develop, therefore the simulator proposed a plausible age of onset for each. The simulator used one of two algorithms to calculate age of onset of each condition, depending on whether or not it could identify the age at which the condition ended.

Each proposed age corresponds to a change in one element in vector $V_{-1}$. The collection of vectors produced by these single health condition changes is the set $V_{-2}$. Consequently, selecting the health condition to change specifies which member of the set $V_{-2}$ is part of the history of this simulation. Although only one vector in $V_{-2}$ will appear in the history of this simulation, all of the health conditions in $V_{-1}$ will be traced back to birth through vectors from sets $V_{-3}$, $V_{-4}$, etc. The question is not whether each condition has a history, but when events occurred.

A safe strategy is to instantiate the vector from $V_{-2}$ occurring at the latest age, along with any facts that had been tentatively proposed with that age and vector. If two or more vectors from $V_{-2}$ share the latest moment in age, one may be selected at random. The history generation step is repeated with the instantiated vector from $V_{-2}$ replacing $V_{-1}$ as the focus of attention.

The "lead to" relations, such as $PL_{j-1 \to i}$, may need to instantiate modifiers in order to produce a duration pdf.

Some modifiers might be defined by a history of a health-condition in an active network. Instantiations of health conditions in active networks create additional temporal constraints for these conditions. These constraints typically dictate that a comorbid health condition, $C_x$, is present at a point in time (e.g. at age N, the moment of transition from $P_{i-1}$ to $P_i$), for a period of time (e.g. at least five but not more than ten years), or both (e.g. for the past two to four years). These conditions can be evaluated for logical compatibility with incidence data and the case. For instance, the instantiation of a modifier may require that $C_x$ is present at the moment of transition from $P_{i-1}$ to $P_i$. If $x \neq j$ and $C_j$ is part of the target vector $V_0$, then this instantiation can not apply in this simulation. The probability of a modifier requiring $C_{x \neq j}$ is therefore zero. A slightly different constraint indicating that $C_x$ is concurrent with $P_{i-1}$ for five to ten years, where x=j−1, may be logically possible.

Note that the outlining algorithm will select this instantiation only if the onset of $P_{i-1}$ is proposed for an older age than the onset of $C_j$. The simulator can therefore be required to add $C_j$ at an older age than the onset of $P_{i-1}$. It is important to reconcile this age of onset of $C_j$ with incidence data for $C_j$, before the tentative instantiation.

The simulation algorithm does not require that exacerbation networks reach any particular health condition prior to changes in their parent conditions. For instance, health condition $P_i$ may permit exacerbations to reach condition $E_k$, while health state $P_{i-1}$ only allows exacerbations to reach condition $E_{k-2}$. The simulation algorithm may suggest that $E_k$ developed before $P_{i-1}$, creating an intermediate vector such as $V_i = \{P_{i-1}, \ldots E_{k-1}\}$, which is in turn instantly preceded by $V_{i2} = \{P_{i-1}, \ldots E_{k-2}\}$. The simulated medical history would indicate that the patient developed $P_i$ and $E_k$ simultaneously.

Figure 7:
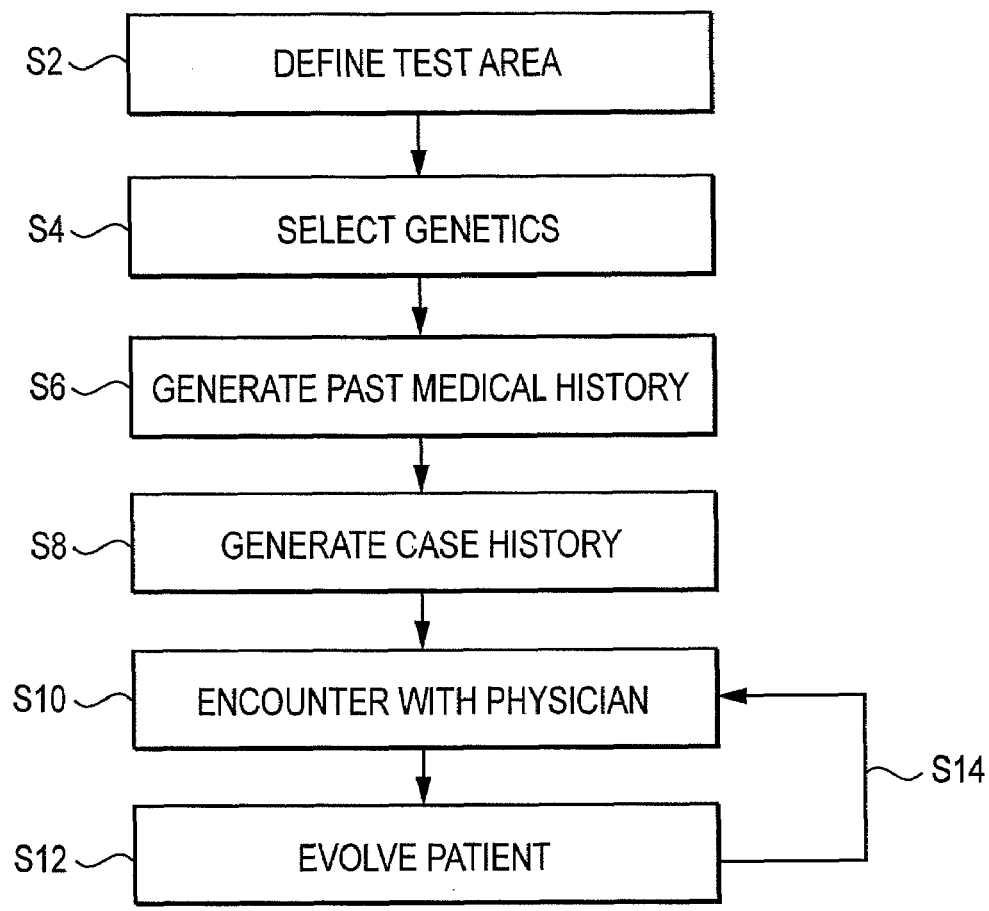
FIG. 7 is a flowchart providing an overview of the stochastic process in accordance with another embodiment of the computer based examination system of the present invention.

FIG. 7 is a flowchart providing an overview of the stochastic process. In FIG. 7, the stochastic process begins with defining a test area or subject area to be tested in Step S2. In Step S4, the sex, race, and other genetically determined facts are assigned to the prospective patient. In Step S6, the past medical history of the patient is generated, by proposing concurrent histories for each of the health conditions. In Step S8, the case history that will be accessible to the examinee is generated for use in the examination.

In Step S10, the examinee or physician encounters the patient at a predetermined stage that is suitable for the examination. The examinee makes a decision as to whether treatment or intervention is appropriate, and either performs the treatment or not. The patient is optionally evolved in Step S12 in accordance with the examinee's decision and actions performed in Step S10, and the examinee may be optionally tested again in Step S10.

Stochastic Process History Outlining Example

Consider an examination of the management of osteoarthritis. Among several cases in this area is one describing a patient with an acute flare of osteoarthritis of the knee. The case presents with established grade II chronic osteoarthritis, obesity, and No Gastric Ulcers. No other networks are active in this case. The health conditions in parallel networks are:
P: Grade 0 Knee Osteoarthritis (OA), Grade I Knee OA, Grade II Knee OA, Grade III Knee OA
C: Normal weight, Obesity, Morbid Obesity C*: No Gastric Ulcer, Grade I gastric ulcer The health conditions Grade I Knee OA and Grade II Knee OA are associated with exacerbation networks:

$^E$grade-II: Baseline Knee OA, Acute Flare of Knee OA
$^E$grade-I: Baseline Knee OA The presenting vector is $$V_0 = \{P_3, E_2, C_2, C'_1\}$$
$$= \{\text{Grade II Knee } OA, \text{Acute Flare of Knee } OA,$$
$$\text{Obesity, No Gastric Ulcer}\}$$

The "lead to" relations required for history generation are $PL_{1->2}$, $PL_{2->3}$, $PL_{3->4}$; $EL_{1->2}$, $EL_{2->1}$; and $CL_{1->2}$. The "lead to" relations required for evolution are $PL_{3->4}$; $EL_{2->1}$; $CL_{2->1}$, $CL_{2->3}$, and $C*L_{1->2}$.

The normal health condition in the Egrade$_{II}$ exacerbation network, Baseline Knee OA, may be instantiated twice. The Acute Flare of Knee OA health condition is incident, and all other conditions are prevalent.

Age-specific prevalence data about the presenting health condition in the primary network, Grade II Knee OA, conditioned on sex, race, and other essentially predetermined and generally permanent patient characteristics are provided.

The probability of generating a white female patient, given a case of Grade II Knee OA is asserted to be 63%, the fraction of all OA cases found to occur in white females.

When sex and race are selected, the state of the prevalence node is defined. The prevalence node supplies the prevalence of Grade II Knee OA in white females as a shape defined by the points {(0 years, 0%); (25 years, 0%); (35 years, 0.2%); (60 years, 5%); (100 years, 45%)}. The prevalence of Grade II Knee OA at any specific age is found by linear interpolation, so that the prevalence at age 20 is zero, and the prevalence at age 80 is 25%. The rapid rise in prevalence from age 60 to 100 suggests a high probability of generating a very old patient, because these data do not reflect the scarcity of very old people.

To correctly simulate the age distribution of patients, an absolute prevalence is calculated using formula 1. Assume that the prevalence of the special condition "Alive" for white females is a roughly sigmoid curve with a median survival around 78 years, such as {(0 years, 100%); (1 week, 99.9%); (1 year, 99.8%); (15 years, 99.5%); 20 years, 99.2%); (50 years, 95%); (60 years, 85%); (80 years, 30%); (90 years, 8%); (99 years, 05%); (100 years, 0%)}.

Formula 1: produces absolute prevalence weights including the points {(0 years, 0); (2 years, 0%); (35 years, 0.2%); (50 years, 2.9%); (60 years, 4.25%); (80 years, 7.5%); (90 years, 2.8%); (99 years, 0.2%); (100 years, 0%)}. The peak absolute prevalence (8.77%) of Grade II Knee OA therefore occurs at age 73 rather than age 100, and absolute prevalence is skewed toward younger patients, so that the median age of prevalent cases is 71. The product of the Alive and Grade II Knee OA prevalence is similarly multiplied by the prevalence of the Obesity and No Gastric Ulcer conditions. This could further skew the age distribution away from the elderly as obesity, a risk factor for death at relatively young ages, is less prevalent in older patients.

Finally, the incidence of Acute Flare of Knee OA is obtained, if it is available. Since this health condition is part of an exacerbation network, it might be safely assumed to be equally likely to occur at any age where its parent, Grade II Knee OA, is present, if the incidence of $E_k$ is not specified. In this case, no further adjustment to the prevalence product produced above is required.

In general, the incidence shape for an incident health condition can be multiplied by the product of the prevalence shapes obtained above. One year is chosen at random from the resulting distribution in a weighted random selection process. We will assume that the process selects age 70 for this patient's presentation. This means that a white woman with a history of Grade II Knee OA, Obesity, and No Gastric Ulcer, presents at age 70 with an acute flare of her osteoarthritis.

The next process generates the past medical history of the patient, by proposing concurrent histories for each of the health conditions in the presentation vector $V_0$={Grade II Knee OA, Acute Flare of Knee OA, Obesity, No Gastric Ulcer}. The first step in this process traces health condition transitions as illustrated in FIG. 8.

Figure 8:
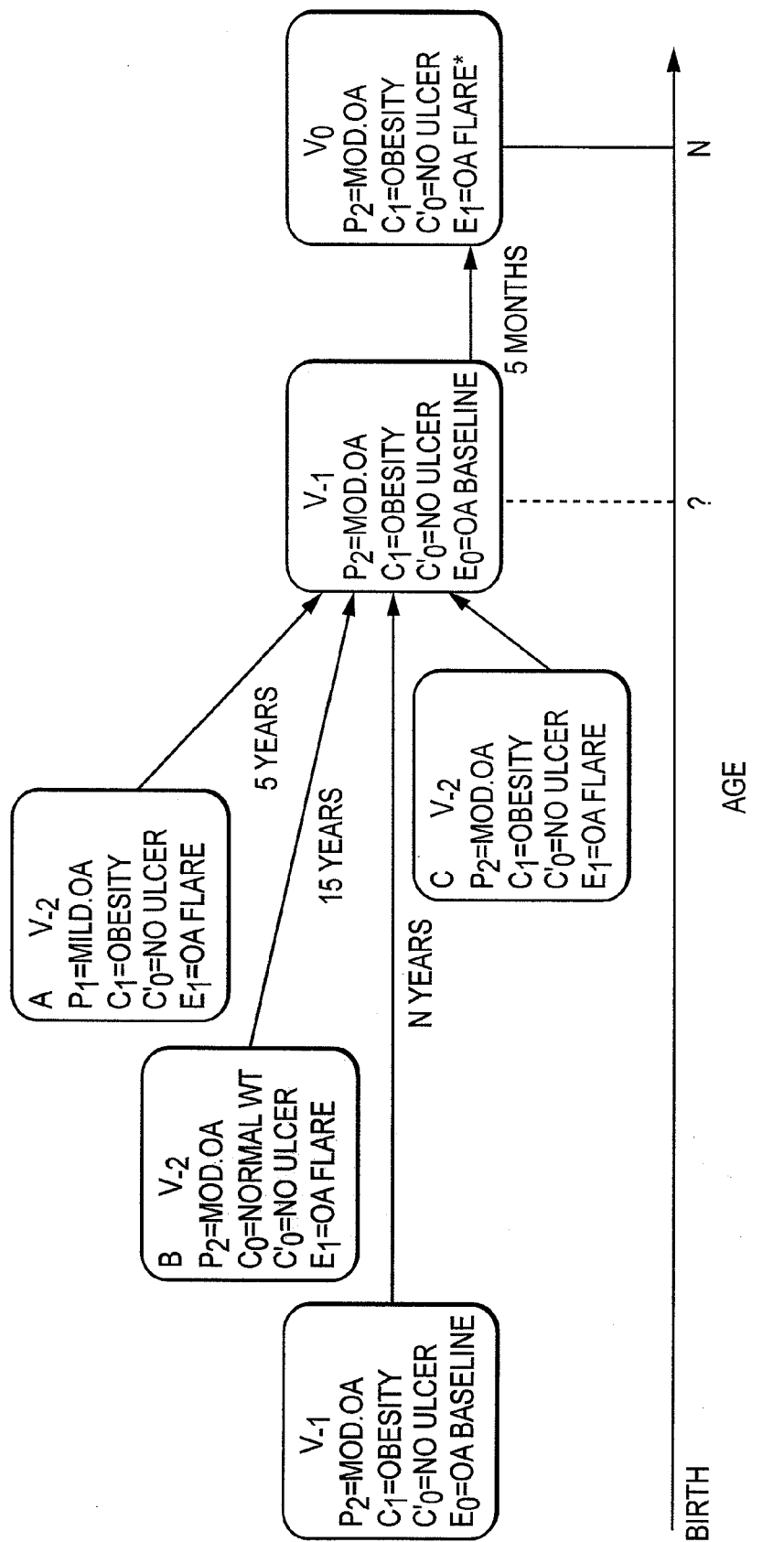
FIG. 8 is a flowchart illustrating a first step in tracing previous health conditions to generate past medical history of the patient for the stochastic process of the computer based examination system of the present invention.

As illustrated in FIG. 8, the Acute Flare of Knee OA is incident, so that its precursor, Baseline Knee OA, must be present in vector $V_{-1}$={Grade II Knee OA, Baseline Knee OA, Obesity, No Gastric Ulcer}. The age of onset of $V_{-1}$ and the preceding vector $V_{-2}$ are obtained simultaneously by predicting when each element of $V_{-1}$ might have developed, and asserting that the last predicted change did occur.

Grade II Knee OA, an element of vectors $V_0$ and $V_{-1}$, will eventually evolve to Grade III Knee OA. A history generating relation, Grade II Knee OA leads to Grade III Knee OA, describes how long this might take, perhaps 5 to 10 years. If this relation posits a shorter interval between these conditions, then the simulation is constrained to produce patients with a recent onset of Grade II Knee OA. If the history generating relation posits a longer interval, then patients may have a long established osteoarthritis condition.

Grade II Knee OA is prevalent in vector $V_0$, presenting at age 70, and with no more than 10 years allowed for evolution to Grade III knee OA, the earliest age at which the grade II condition could have appeared is 60 years. If so, this patient remained a longer time than usual in Grade II Knee OA, and the transition to Grade III Knee OA is expected shortly. The patient is most likely to have developed Grade II Knee OA between age 65 and 70, among a cohort in which no one would have progressed to Grade III Knee OA by age 70. If the incidence of Grade II Knee OA rises from age 60 to 70, the product of the reversed cumulative PDF and the incidence shapes will be further skewed towards later ages. We will assume that age 65 years is randomly selected from this product.

A similar procedure produces an age of onset for obesity. A history generating relation, Obesity leads to Morbid Obesity, describes the length of transitions, perhaps 10 to 25 years. Obesity is prevalent in $V_0$, so a reversed cumulative PDF is multiplied by the incidence of Obesity, and an onset age between 45 and 60 is proposed.

The No Gastric Ulcer element in $V_0$ is a stage 0 condition, which might evolve to stage I at some time. Since the incidence of stage 0 conditions is always between 0 and 100% at birth, but is always 0% after birth, so that the duration PDF is irrelevant to the selection of the age of onset, as long as the reversed cumulative duration PDF is non-zero at birth.

Figure 9:
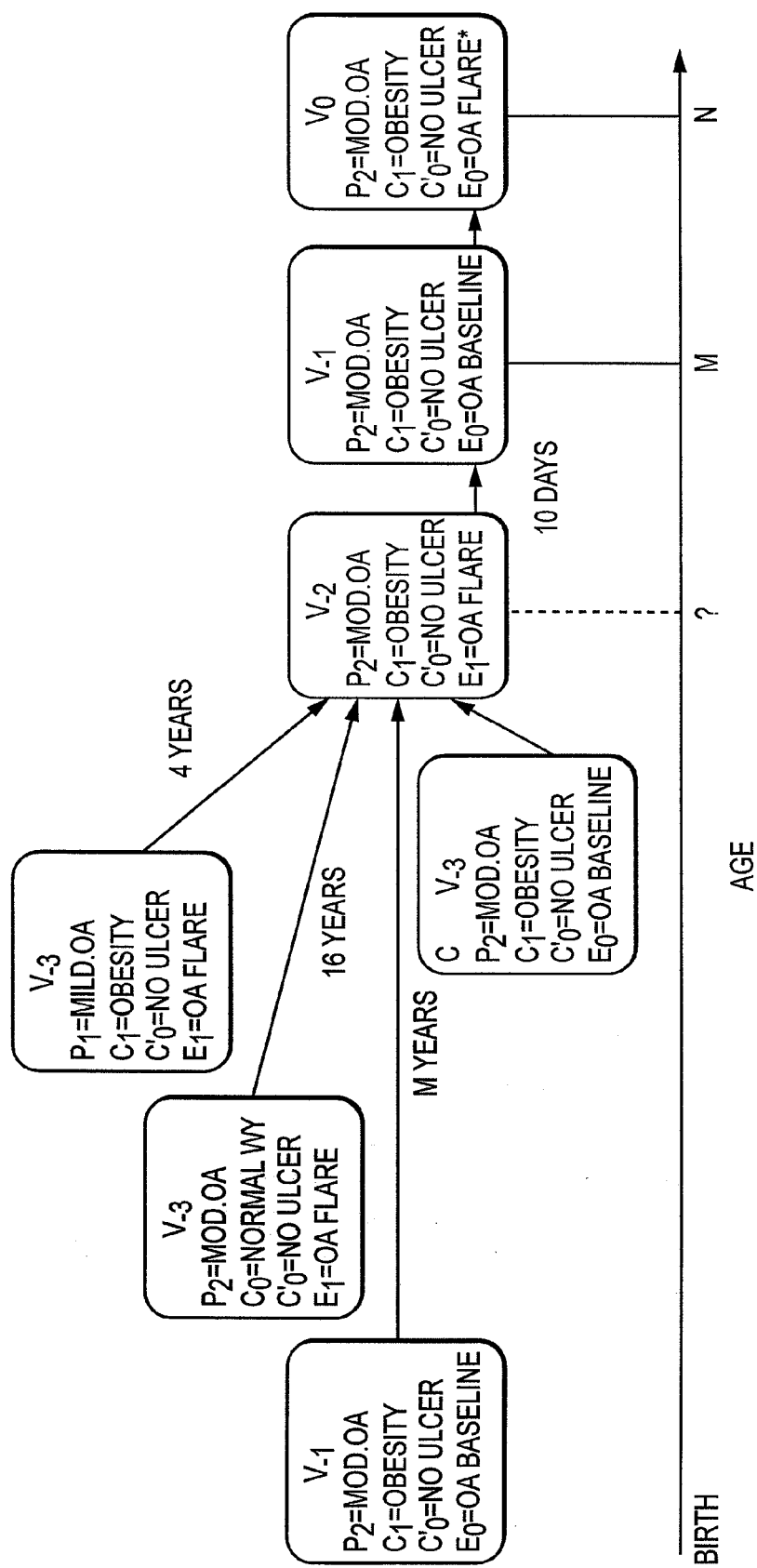
FIG. 9 is a flowchart illustrating a second step in tracing previous health conditions to generate past medical history of the patient for the stochastic process of the computer based examination system of the present invention.

Finally, the Acute Flare of Knee OA condition has a known onset time, at age 70. The history generating relation, Baseline Knee OA leads to Acute Flare of Knee OA, describes the duration of Baseline Knee OA, perhaps 3 to 12 months. If the duration of acute flares is very short, and there are no other conditions in the exacerbation network, then this PDF also describes the periodicity of flares, given the presence of Grade II Knee OA. If specific incidence data for the acute flare condition are not available, the incidence of the parent condition for the exacerbation network (Grade II Knee OA) can be substituted. The product of the reversed (but not cumulative) duration PDF and the incidence supplies a distribution from which to select an age of onset, for instance 69 years, 7 months. Since this is the oldest age proposed, it is selected and instantiated. Step 2 of this process, illustrated in FIG. 9, is analogous to Step 1 described above, and therefore, no additional discussion is described herein.

Finding Generation for Stochastic Process

Finding generation adds detailed descriptions of patients' features to the outline generated in the steps above. Beginning with a healthy newborn patient (or embryo) of the specified sex and race, the finding generation process assigns values of specific findings expected in healthy individuals. These may change when the patient develops a new health condition at the age selected by the outlining process.

The patient's detailed features are generated using modeling instructions stored as Reasoning elements with health conditions. Specific findings associated with normal health are created in a sequence indicated by these instructions. Each Specific finding is initially defined from the onset of life until age 100. For instance, the patient's height is derived from a randomly generated percentile and a set of shapes resembling a pediatric growth chart extended to age 100. The set of shapes used may be conditionally dependent on the sex, race, and any other established facts about the patient.

The finding generation process should generally create dependent findings, e.g. knee pain, after generating the findings upon which they depend, e.g. joint space narrowing. Careful selection of findings to represent may reduce some dependencies. For example, the model in general is more robust if height and body mass index are considered to be independent findings, and weight is not calculated until explicitly requested during a simulation. Therefore, the model in general is more robust if height and body mass index are considered to be independent findings, and weight is not calculated until explicitly requested during a simulation. Most findings are instantiated as a series of pairs of values and ages. Values at other ages may be found by linear interpolation.

Findings may vary with predictable circadian, lunar, and annual rhythms, described by shape subpatterns. Shape subpatterns can be combined with a shape to produce fluctuations on realistic temporal scales.

Finding distortions illustrate events having temporary effects on the shape of some value. For instance, a temperature shape during a febrile illness might be 39° C., with a distortion pattern indicating a 1° C. drop for four hours following administration of acetaminophen. The exact temperature reported at a given time would depend on the current value of the lifetime temperature shape and whether the patient consumed acetaminophen in the last four hours.

After determining patterns for all findings present at a point in time, the simulator proceeds forward in time to the next health condition vector. The simulator updates findings for the new situation. This loop continues until the computer has described the findings of the patient in the final health condition vector.

Using Pre-Generated Patients

In accordance with one design of the present invention, when the computer based examination system generates and evolves a random patient, it cannot reuse the patient information if the patient is evolved once. That is, every time the examination is executed, we need to generate a patient to continue the test. Not only does the process of generating a patient take tremendous time, but also the evolved patient cannot generally be tested again in the future.

In accordance with another design of the invention, the patient is pre-generated, evolved and stored in the Whiteboard database. The presentation system can test the patient in countless time if wanted. Furthermore, different physicians can test the same patient at the same time.

Figure 10:
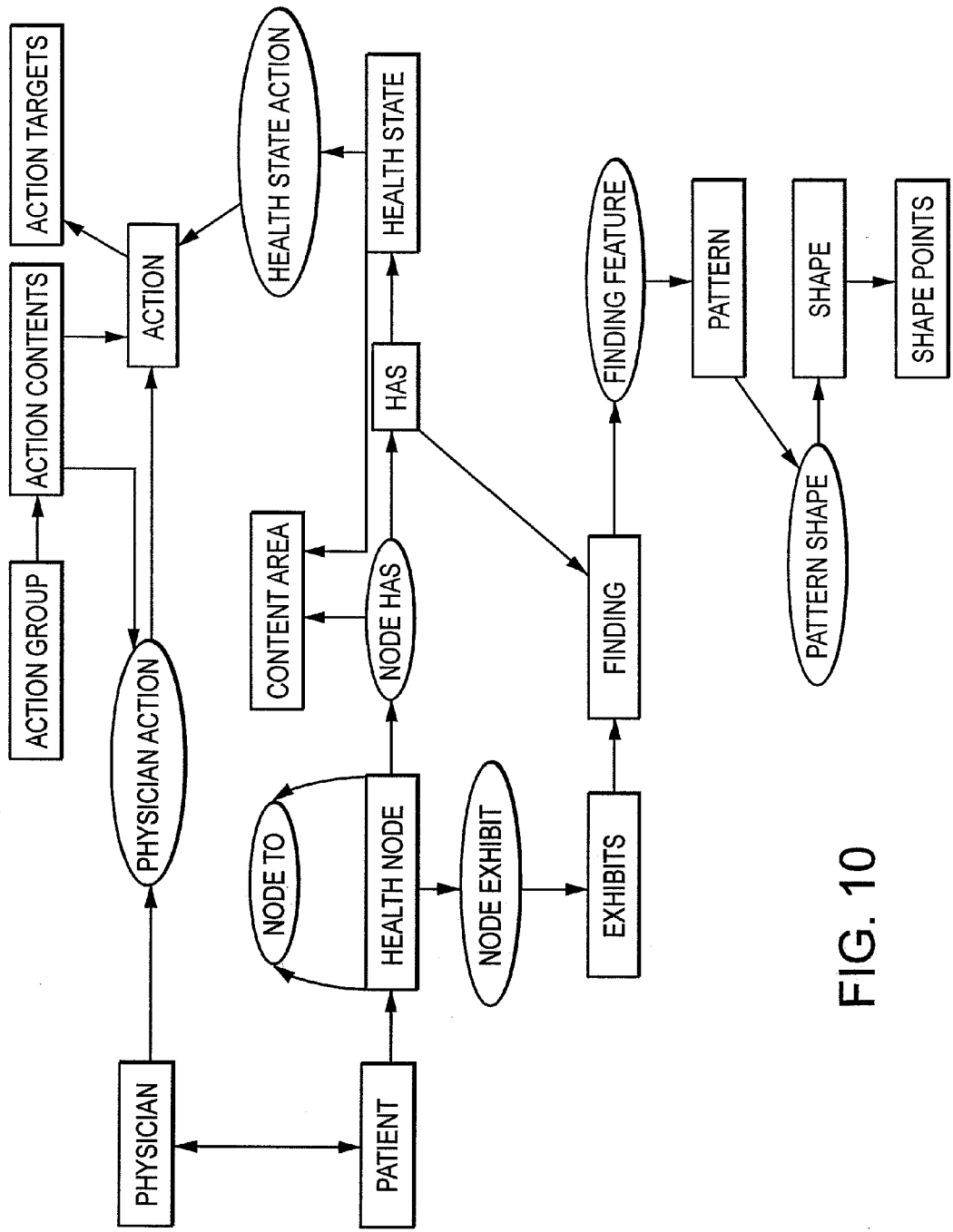
FIG. 10 is an illustration of the entity-relationship model data structure stored in the white board database when patients are not pre-generated.
Figure 11:
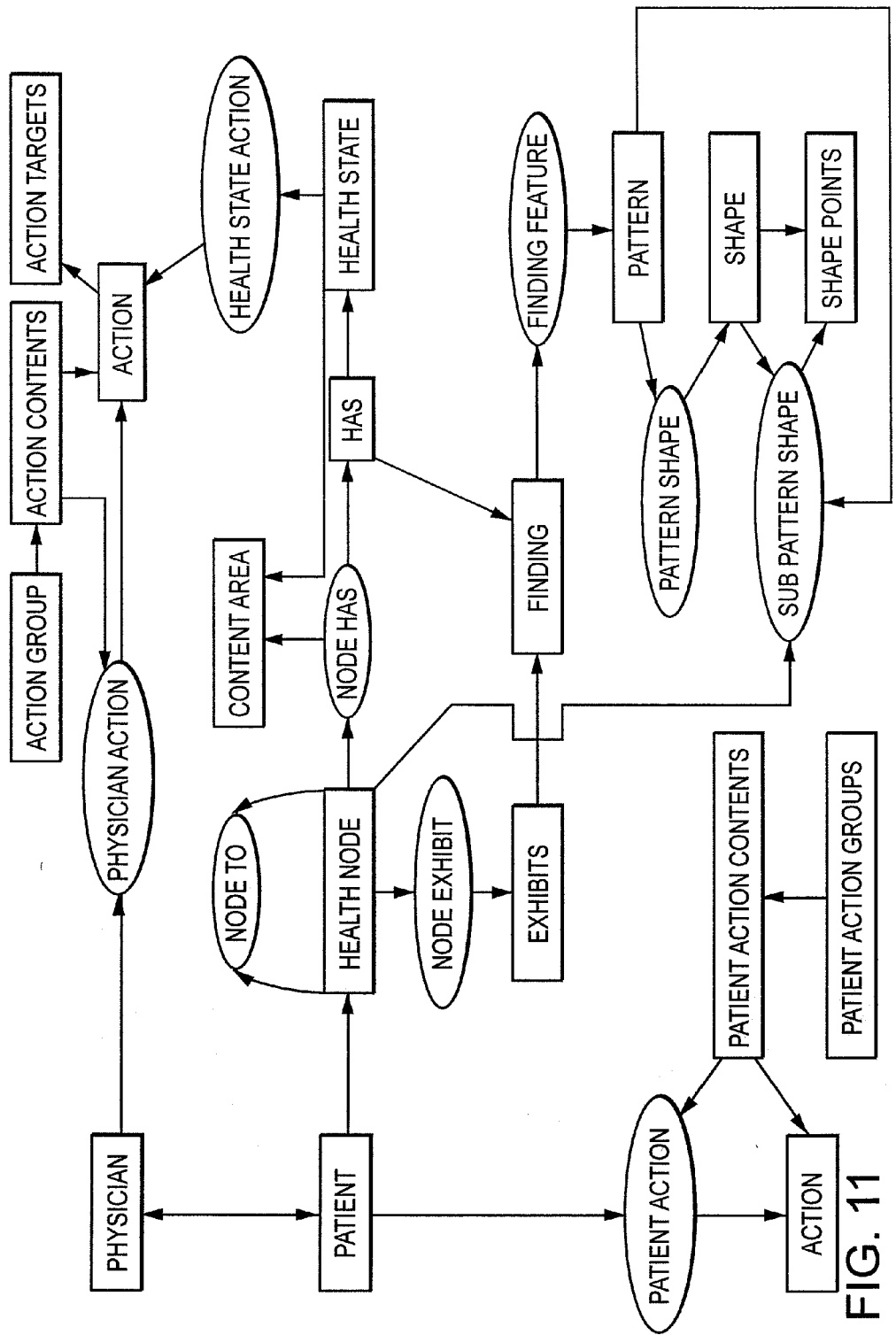
FIG. 11 is an illustration of a modified entity-relationship model data structure stored in the white board database when patients are not pre-generated.

FIG. 10 is an illustration of the entity-relationship model when patients are not pre-generated, and FIG. 11 presents the modified entity-relation diagram of the modified Whiteboard database when the patient is pre-generated. Each node represents a status of a patient with parallel health states. For example, when a patient is generated, he or she is located at node 1, the patient might be evolved to several status located at node 2, 3, 4 . . . , etc. Therefore, a patient can have many nodes.

Many nodes can share same EXHIBITS and HAS. For instance, when a patient is evolved to a severe knee problem, we first take out the most updated EXHIBITS of the previous node, modify it and then write it to the new node, and at the same time generate a new EXHIBITS for the new node. The new node will point to the EXHIBITS prior to the most updated EXHIBITS of the previous node. If nodes are in the same content area, they also share the same FINDINGS and PATTERNS, but their shapes are different, which can be found in table Pattern_Shape.

Since different physicians can use the same patient for the test at the same time, the corresponding action contents needs to be given for each physician. Therefore, every time a patient has a new node, we also generate the patient's action contents. When the physician gets to the patient with the specific node, the action contents are copied to physician_actions tables.

The table ACTIONS, HEALTHSTATE and ACTION_HEALTHSTATE are pre-generated, and a corresponding utility integrated with pre-generating COA is created. Accordingly, the evolution process for pre-generated patients is, for example, as follows:

a) Based on the parallel health states of the patient at the specific node, fetch all corresponding actionID from action_healthstate.
b) Based on the possible target of each actionID, construct all combinations that lead to different parallel health states.
c) Create a new node for each possible action combination.
d) Copy the SHAPE from old node to the new node.
e) Construct a tuple in table NodeToNode where the action combination, old nodeID and new nodeID will be stored.

Generating Patients with Parallel Health State Networks

A detailed description of parallel health state networks is now described. We have determined that parallel health state networks provide a model with a reasonable biological basis, more easily defined data, greatly improved reuse potential, and a better segmented implementation. Evolution of synergistic health problems (e.g., vicious cycles) are managed using structures from the original data model. A working patient generation process is creatable using the parallel network model.

We have determined that the number of conglomerate health states expands combinatotially, and the incidence and duration of these conglomerate health states is often a matter of speculation or is redundant with previously stored information.

We have also determined that a parallel network approach improves on the accessibility and reusability of health state data, while retaining the ability to handle the dependencies inherent in synergistic cycles.

Humans are composed of inter-dependent cells organized into tissues and organs. Some tissues directly or indirectly control the state of cells in other organs through mechanical, neurohumoral, or other processes.

An individual's health reflects the current health of all of these cells. Therefore, a very high resolution model of the life of a human body might describe the histories of the cells comprising the body, including their dependency on other cells. In clinically recognizable processes, the cells comprising one tissue share similar structure, function, and health with many of their immediate neighbors. Their health may diverge rapidly from the health of the cells in other tissues. Therefore, a model concentrating on the histories of tissues retains considerable resolution.

Each tissue can be imagined to evolve on its own standard schedule unless some local insult occurs, or an insult to another tissue alters the schedule. The normal tissue schedules proceed in parallel. For instance, bone, Islets of Langerhans, nephrons, and retinal tissue all gain and lose function at predetermined rates. If bone loses function (strength), a local pathological parallel process (fracture) becomes more likely. If Islet cells lost function (insulin secretion), distant pathological parallel processes in nephrons and retinas become more likely or progress more rapidly (diabetic nephropathy and retinopathy).

Without parallel networks, distractors, such as randomly appearing colds or a history of appendicitis might require many conglomerate states. Also, information collected for one disease domain might have to be completely replicated in other domains (for instance, obesity descriptions would occur in osteoarthritis, diabetes, hypertension, combinations of the above, and independently).

We have also determined that many therapeutic complications are acute site-specific illnesses superimposed on an antecedent illness. On the other hand, some problems interact in synergistic cycles: Osteoporosis increases the likelihood of fractures, and immobility (following a fracture) increases the rate of progression of osteoporosis. Consequently, many of the most interesting disease processes are intertwined with others. In a network of conglomerate health states, these dependencies can be explicitly described at nodes and along edges between nodes. In a parallel network model, the interacting networks must be aware of each other.

This view of health and function, we have determined, suggests a definition of parallel health state networks: A parallel health state network for a tissue describes a collection of clinically discoverable and mutually exclusive states in which that tissue may exist, and possible transitions between states. For example, the normal development of a tissue, described from a person's birth to death, is one distinct state in a network.

Physically separated cells of the same tissue type may exist in very different states. For instance, the left and right knee joints are susceptible to pathologically indistinguishable osteoarthritic changes, but one knee may exhibit more advanced changes than the other. Therefore, parallel networks require identification of involved sites.

A parallel network is, not coincidentally, a disease staging scheme. Parallel networks for chronic diseases are typically restatements of familiar staging concepts (e.g., Stage 0 or no disease, followed by Stage I or mild disease, and so on). The parallel network illustrates these as sequential stages, even in acute processes such as ankle sprains or burns. A third degree burn is always preceded by a second degree burn, if only for the briefest moment of time.

Parallel networks alter knowledge acquisition and storage requirements, as well as patient generation algorithms, when compared to conglomerate health state models. Diagnoses previously combined in a conglomerate state become distinct states in different parallel networks. The conglomerate health state of the body is described by a vector indicating the current status of all parallel networks.

Figure 12:
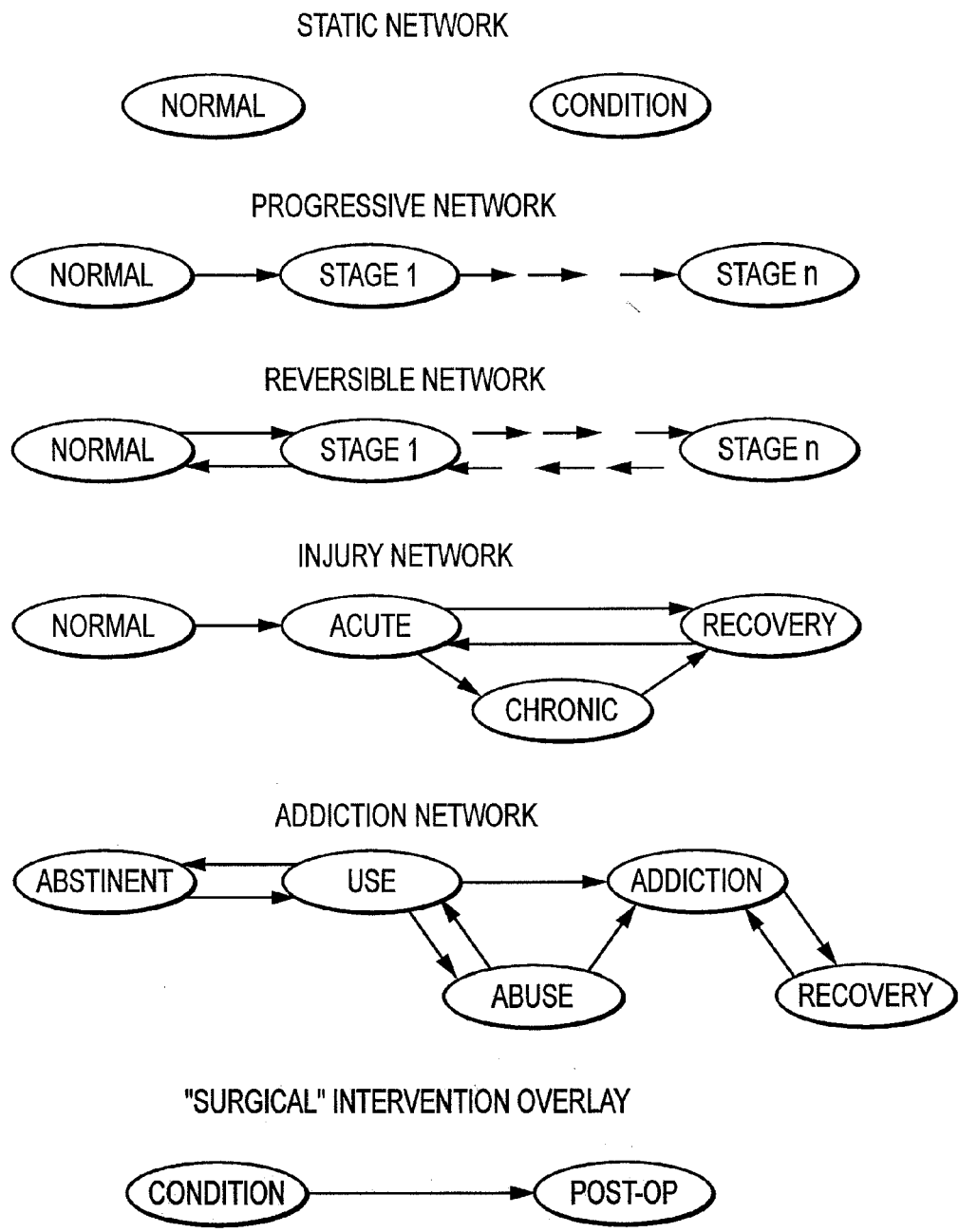
FIG. 12 is an illustration of parallel network structures for the computer based examination system of the present invention.

Illustrations of their disease domains help medical experts understand the scope of their knowledge acquisition task. Initially intricate domain models were decomposed into much less threatening parallel networks. FIG. 12 illustrates parallel network structures. The simplest network is a collection of one or more static states, typical of genetic (Down's syndrome) and some congenital conditions (anencephaly). The progressive network is a series of states with no cycles, typical of degenerative illnesses such as osteoarthritis. The reversible network illustrates chronic but reversible conditions, such as essential hypertension and weight disorders. In the injury network an acute insult evolves to either recovery or a chronic condition with a later recovery. Injury networks describe many infectious diseases and trauma.

The addiction network illustrates that a person may abstain from, use, abuse, or become addicted to something; in the current model, a previously addicted person can only be addicted or recovering, but cannot return to abstinence, use or abuse. The surgical intervention overlay illustrates that new states can be added to the above networks using irreversible therapies such as radiation or surgery.

Parallel networks of three types are identified. The primary network contains the diseases that define the domain, such as diabetes mellitus. The second type of network contains a risk factor for progression through the primary network, such as obesity. The third type of network includes complications attributed to states in the primary network or its management, such as retinopathy.

We have also determined that the following information is used to create parallel networks: 1) how long a risk factor should exist before it could influence a transition between states in a primary network, 2) the time required for transitions in the primary network, given-different combinations of risk factors, and 3) the number of passes an individual patient should be allowed to make through a cycle (e.g., from acute injury to recovery back).

The data model objects originally intended to store risk factors included a "Person HAS Health State" relation, which identified a health state, its onset and duration. In addition, HAS relations indicates a preceding HAS relation to support tracing of medical histories. These attributes are adapted to describe parallel synergistic networks.

The patient generation process uses a weighted random process to select all times and events, starting with an age of onset for a health state on the primary network. Risk factors are selected next. Unlike the conglomerate health state patient generation algorithm, any diagnoses associated with altered risk must be described in a parallel network. The plausible range of duration for each risk factor is stored in a HAS relation, and used in selecting its onset age. If the risk factor evolves independently of the primary network, the HAS relation does not indicate a preceding HAS, and the algorithm creates the risk factor history using default assumptions in its parallel network. If the primary network does interact with the risk factor, the preceding HAS relations provide time constraints that promote plausible concurrent evolution of the primary and risk factor networks.

The original history generation algorithms are used within independently evolving parallel networks. Consequently, the system continues to support conglomerate health states described as a parallel network. In contrast to the conglomerate health state model, the parallel network technique may require explicit and separate generation of the histories of the primary network and any number of risk factors.

Computer Implemented Process

Figure 13:
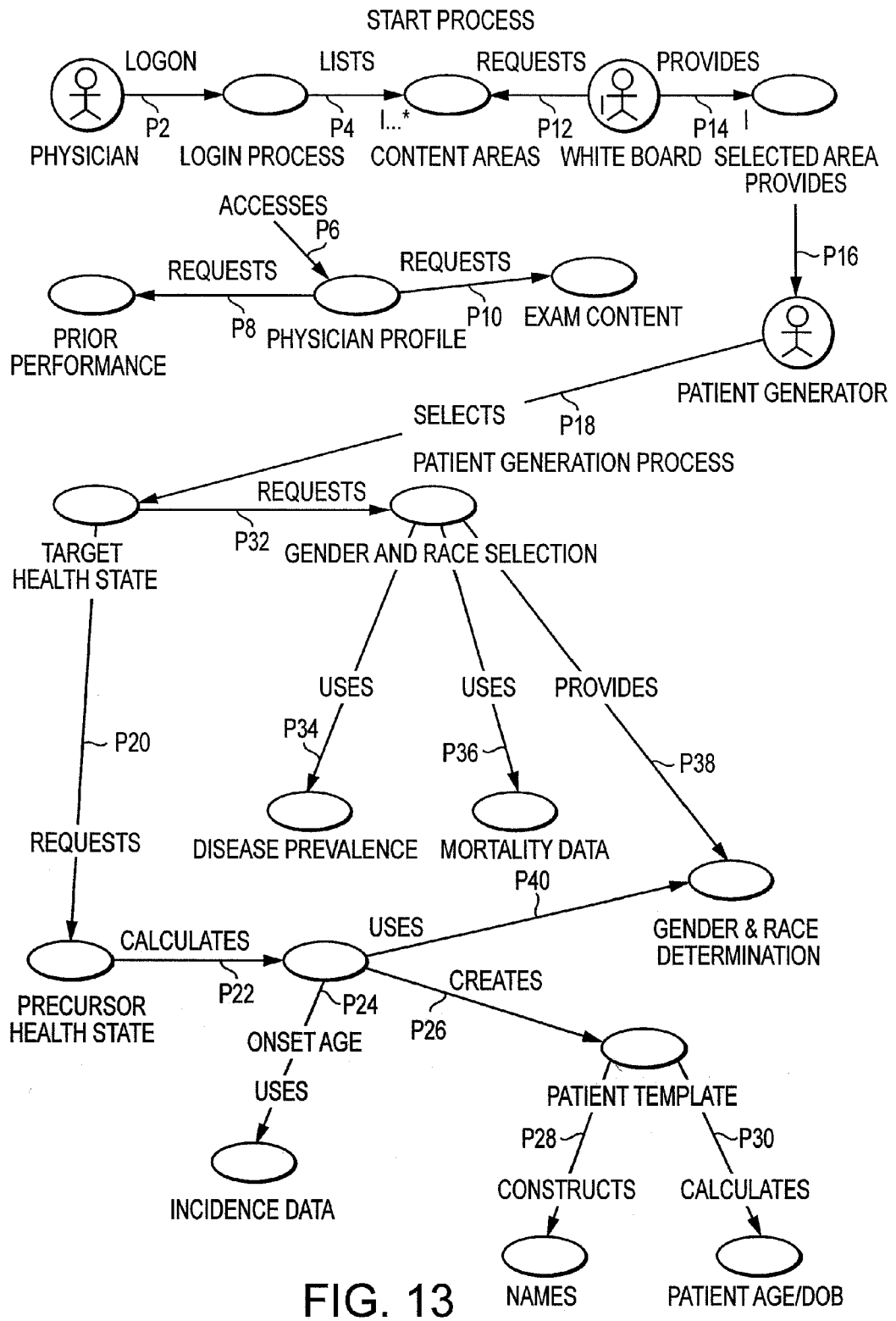
FIGS. 13-14 are detailed flowcharts of the process of the computer based examination or assessment system of the present invention.
Figure 14:
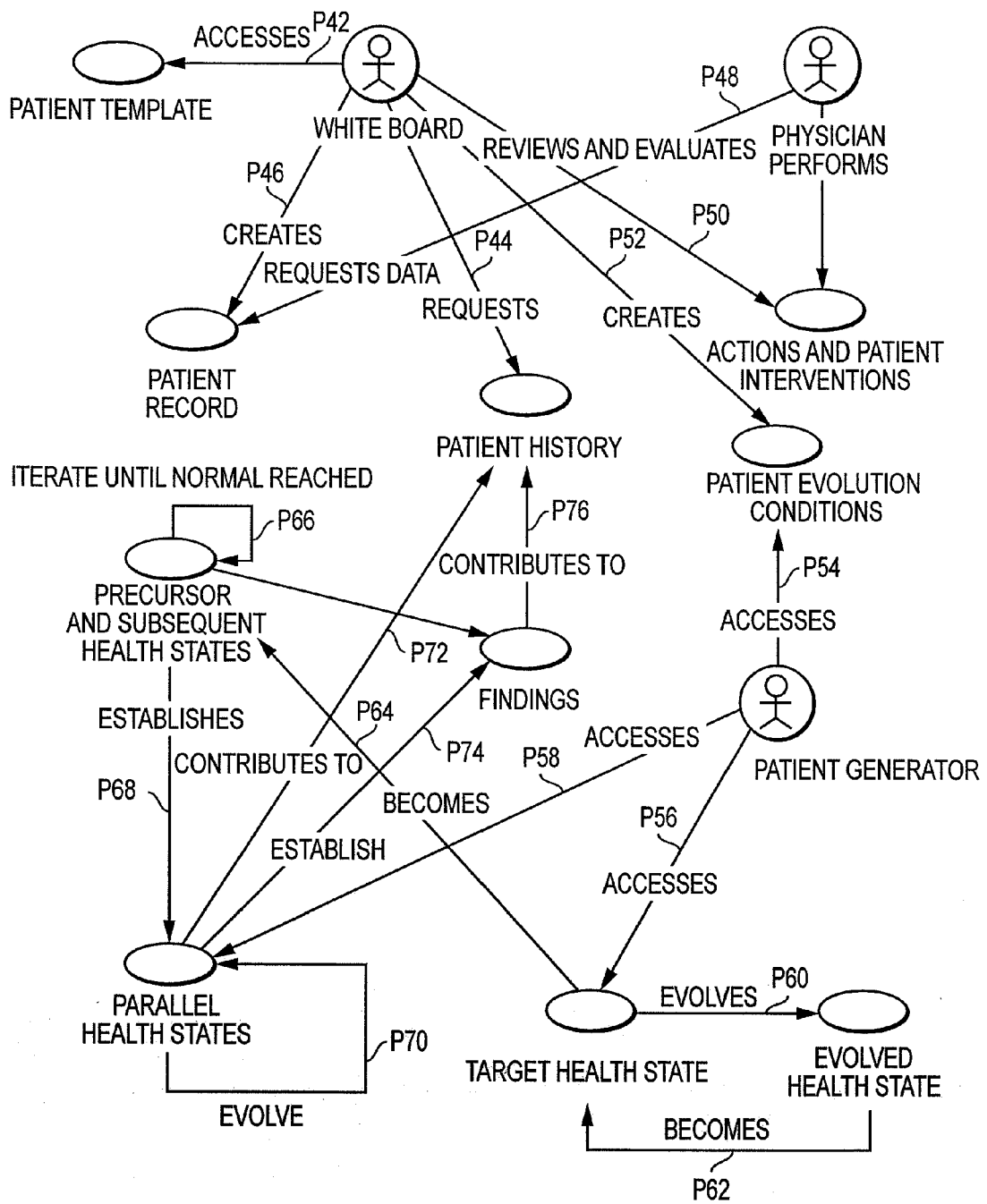

The process of the computer based examination or assessment system is described in detail in connection with FIGS. 13-14. The computer implemented process includes the overall concept that the physician is presented with an examination, and the process generates multiple instances of patients. These generated patients represent clinical scenarios that a physician would have to go through to administer proper treatment. These scenarios are stored in a white board database which stores both the database implementation (i.e. the patients stored in data structures), as well as computer codes which operate from base structures including information on physician.

There are three basic actors in the computer based examination system: physician, white board and patient generator. The physician/examinee initiates the white board action by logging in. Once the examinee logs in, then the white board makes one or more requests to the patient generator. The white board generally provides the patient simulator with the basic testing area. The patient generator then starts the process of generating the patient and evolving backwards, and optionally forwards in time for pre-generated patients. Thus, the computer based examination system includes separate programming objects in the general C++ programming sense for physician, the patient and the white board.

In general, the physician/examinee pre-registers to take the examination, and provides (or the system already has stored) detailed background information on the physician, areas of weaknesses, prior examination information, and the like. Thus, the physician logs-in to the computer based examination system in Step P2, and the system validates the physician in accordance with predetermined criteria, e.g., user ID, password, correct examination, and the like.

The physician/examinee is either presented with an optional list(s) of subject areas for examination or mandatory subject areas for examination in Step P4, responsive to information stored in the whiteboard database via requests thereto in Step P12. Alternatively, the examination areas might be hidden, and the examinee might be told that this is a diabetic problem, with certain management issues. The examinee may optionally have a series of selections, whether it is in terms of individual patients or they could be in specific areas.

In some instances, the examinee may be provided a patient with some specific statements about the patient. The computer implemented process may optionally determine whether the physician has been examined before. If the answer is yes, then the physician might require, for example, five of fifteen specific subject areas for the examination, of which one or more would be available for testing.

In addition, prior performance of the physician may also be considered using a pre-stored or generated physician profile via Step P6, and requests to the prior physician performance via Step P8. The specific exam content is then requested in Step P10 responsive to at least one of physician profile, prior performance, content areas. Accordingly, one or more of prior performance, the physician profile, the content of the examination, are used to provide a selection list of the physician to choose from in Step P14.

Depending on the above information, the patient generator process is then initiated to create a patient for the examination in Step P16. The patient generation process may be performed in Step P18 in real-time for each patient, or may be pre-generated as described above. Under the real-time scenario, the selection of a problem area in Step P14 translates into a target health state or area.

For example, if the problem area selected was diabetes, the target health state in the knowledge base would be diabetes. Using the target health state, there are generally a plurality of health states associated therewith. The computer implemented process then optionally randomly selects one of these areas as a precursor health state in Step P20. For example, a mild case of diabetes may be the precursor health state for normal health state of diabetes.

The selection of the precursor health state is based on, or calculates, onset age in Step P22 via incidence data in Step P24. The history generation computer process is a mechanism that sets up a reasonable beginning time and ending time for the patient that is being presented. The computer process chooses a target health state, precursor information, sex and race from the target health state, and establishes the age of the patient. The computer process then moves backwards in time to establish onset age when the condition occurs, and proceeds backwards in time all the way to the normal state. Next, the process moves forward in time to determine potential subsequent health states for the patient based on a variety of possible interventions performed by the examinee. Thus, the process has two stages.

Depending on the precursor information/health state, information such as the sex and race, along with disease prevalence in Step P34, mortality data Step P36 and incidence information in Step P24, are used to select the specific sex and race for the simulation.

The mortality data is based on sex and race. The sex and race is selected from the health state, incidence or prevalence data and sex and race specify mortality data. For example, if the health problem that is presented to the examinee is new to the patient, then it is incident (e.g., a recently broken bone). Alternatively, if the health problem is an old established problem such as long term diabetes, the health problem is prevalent. Thus, the incidence and prevalence is inserted into the patient case history over and over again depending on the particular problem. Accordingly, a pre-determined decision is generally made as to what types of disease are to be tested, prevalent disease or incident disease.

The sex and race selection uses the disease prevalence and mortality data in the sex and race selection process. The mortality data and disease prevalence are used to establish the reasonable ages and sexes, and also ages of on-set. For example, this mechanism prevents generation of pregnant males, 14 year old Type-II diabetics, and the like.

For example, the computer system determines, or is instructed as described previously, that the problem area is arthritis. The sex, race, and age of the patient are determined, for example, at the point in time where treatment may be necessary. The patient history is then generated back through the process/time to establish onset times of the various different health states. That is, from, for example, the point in time where the arthritis is severe, the patient history is generated at a point when the arthritis was mild, and back to when the arthritis was substantially normal.

When the sex and race selection process is completed via the combination of sex and race selection in Step P38 and onset age calculation in Step P40, a patient has been generated at a specific point in time with a specific health state problem and the characteristics of that problem. Thus, the computer process has generated the patient, moved backwards in time from the disease onset age all the way back to normal. For example, if the computer process started with a mild condition for a specific disease, the computer process goes backward one time interval to normal from mild. If the computer process begins with moderate, the computer process will move backward in time from moderate.

As a result of the computer process, a patient template is also generated in Step P26 using the onset age determination in P40 and sex and race selection in Step P38. In addition, the generated patient is given a name in Step P28, and age including a date of birth in Step P30. The physician/examinee is then provided with the history of the patient for use in diagnosing or prescribing treatment for the generated patient. The patient history includes, for example, age of the patient, race and sex. Up to this point in the computer process, the patient is created. From this point of the examination/computer process and forward, the patient and physician's interaction with that patient determine both the information provided to the physician/examinee, as well as potential evolution of the patient. Changes in the patient's characteristics is a function of physician's action or inactions using the evolutionary process described below.

The evolutionary process is performed using the knowledge base structure or entity relationship model described in detail above. The knowledge base structure has been separated from the white board structures described above for administrative purposes, but alternatively may also be combined therein. The knowledge base represents all the information that does not necessarily have to go with the patient for purposes of presentation to the examinee. The knowledge base includes information used to create the patient and provide instances of information.

However, separating the knowledge base from the white board structure has the advantage that the computer generated patients do not require as much data to be transported therewith. Accordingly, a separate structure is created called the white board structure. The white board structure advantageously includes the information required to generate the patients and to present the patients to the physician/examinee. The white board structure includes information containing patient description and all the findings that are typically generated that are not necessarily related to the problem. For example, blood pressure, blood glucose, and the like.

That is, the white board structure provides all information that is generally available to the examinee, such as information satisfying examinee queries on prior history, laboratory tests, and the like. In addition, when pre-generated patients are used, all findings associated with the patient including all pre-generated evolutionary states are also stored in the white board data structure.

For example, if the patient had moderate arthritis, the patient may generally transition to two other health states: severe arthritis, or mild arthritis. Thus, in one embodiment of the invention, the computer process pre-generates the possible health states for the patient. According to this embodiment where the patient is pre-generated, the process of evolving a patient may, in some circumstances, be more computationally efficient than to generate the patients dynamically. Thus, for pre-generated patients described above in detail, all possible states are generated ahead of time and then used by the white board structure in accordance with the pre-generated state when activated or selected by the examinee.

The white board accesses the patient template in Step P42, and generates the patient record in Step P46, responsive to requests initiated by the white board to the patient history information in Step P44. The patient record is not generally reviewable by the examinee, except on individual requests by the examinee in Step P48. The examinee requests information from the patient record in Step 48 which provides the examinee the physical view of the patient. For example, the patient's blood-pressure may be stored in the patient record for retrieval by the examinee. Other examples of information stored in the patient record include chief complaint, past medical history, past patient behavior or compliance information.

The white board will also generate examinee actions and patient interventions in Step P52 by reviewing and evaluating the physician intervention in Step P50, responsive to the patient record. The examinee actions and patient interventions contribute to the patient evolution conditions used in the patient evolution process described above in detail.

Whether the patient is pre-generated or not, the computer process/patient generator generates the initial patient, and subsequently evolves the patient, and subsequently presents same to the examinee. The patient is generated by the patient generator accessing the patient evolution conditions in Step P54, the target health state in Step P56, and any existing parallel health states in Step P58. The patient is evolved by the patient generator in Step P60 to the evolved health state, which may become the target health state in Step P62.

At this point we have a patient on the white board presented with a particular health state, which typically is the form of a chief complaint. From this time on, the examinee/physician takes control of the process, and nothing is going to happen in the computer based examination system unless the examinee/physician does something, unless the health state is time dependent and able to advance to another state automatically, such as by inaction on the part of the examinee.

For example, if the health state is an acute problem, such as a heart attack, there may be a time dependency built in that is going to force some action of the physician within a specific time before the patient experiences another heart attack. In this example, the examinee using the computer based examination system may dismiss the patient, the patient will walk out of the doctor's office/hospital, and the examinee would receive notification that the patient just showed up in the emergency room with a problem.

Alternatively, if the examine is too slow in diagnosing an illness, the inability to treat the patient in a short period of time may also result in the patient progressing to a different health state. For example, a patient that has a heart attack might progress to a more serious state if the examinee does not perform corrective measures very quickly while the patient is, for example, in the hospital. In general, allowing time to elapse without intervention is an intervention choice along with the other active interventions that an examinee might choose.

In order to determine the target health state, the "iterate until normal reached" process is initiated via Step P64 which sets one or more precursor health states to the target health state. The "iterate until normal reached" process iterates in Step P66 until the normal health state is reached backward from the target health state. For example, if a mild health state is selected, the precursor health state is normal. The "iterate until normal reached" process also establishes one or more optional parallel health states in Step P68. Precursor parallel health states are then generated as needed in Step P70, which are then used to contribute to the patient history in Step P72.

The computer based exam-nation system ensures that the age of onset for the various parallel health states is reasonable. Thus, the process of generating precursor health states for the parallel health state is a multi-dimensional process of monitoring health states to be consistent, to prevent unreasonable scenarios, time frames, and the like. If the parallel health states are related, they have to be related to each other sufficiently enough so that the evolution of health states makes sense.

The parallel health states are also used to establish the findings in Step P74, which contribute to the patient history in Step P76. While the above steps have been described in, more or less, a sequential manner, it should be clear that the various steps described herein may be performed in parallel, independently, and/or non-sequentially, as needed or for computational efficiency.

Advantageously, the computer implemented process includes the capability of utilizing parallel health states as part of the patient generation process, which is described above in detail. As part of the generation process, a decision is generally made to include or exclude those particular parallel (e.g., morbid or co-morbid) health states along with the original state of the disease.

We have determined that sometimes health problems tend to be concurrent, but they are not generally defined as being necessarily interrelated. The computer based examination system provides the feature of handling a plurality of health states, either related or not related to each other. For example, there tend to be lots of people with diabetes and high blood pressure. Accordingly, we define these two health states as related to each other. Alternatively, the plurality of health states may be considered to be substantially independent and still within the scope of the computer based examination system of the present invention.

The present invention further provides the feature of dealing with parallel health states substantially or completely independent of each other to permit dependent or independent management decisions. For example, a person that has diabetes and high blood pressure generally requires slightly different management decisions than a person who just has high blood pressure or a person who just has diabetes. For example, the physician/examinee may prescribe a more expensive anti-hypertensive drug if the patient has both diabetes and high blood pressure because of potential complications unique to the combination of health states. Thus, the computer based examination system may be used to determine whether the examinee has made the appropriate management decision. Alternatively, the computer based system may be used to collect various responses from different well recognized physicians to establish a minimum level of care for insurance companies, health care organizations, other physicians, and the like.

The present invention also provides the feature of providing distractions when attempting to diagnose the disease/illness. That is, the patient may include symptoms and/or indications that might be related to the problem seemingly presented to the examinee, but, in fact, these indications distract the examinee along an inappropriate path, such as excessive testing, over-prescribing medications, and the like. Accordingly, we have also determined that distraction makes a good argument for having parallel problems.

At this point and time, the computer based examination system selects an area for examination, and is in the process of working backwards in time. The process iterates from precursor health state down to the normal health state, where at each precursor state the process considers potential co-morbid problems. Both the precursor or subsequent health states are the primary problem, and the parallel health states generate findings. The findings are a part of the patient history. For example, a finding of obesity might be a change in weight. The process moves backwards while at the same time looking at potential parallel health states have been substantiated. The history of findings are generated at the white board level.

Now if the physician takes some action at this point in time that causes patient evolution (that is, the physician causes some action which the white board is checking at this point and time), the white board matches the action up against something that is going to cause patient evolutionary health state change. The white board then makes a request to the patient generator to evolve the health state.

If the full patient has been generated on the white board, then the patient generator is replaced with the white board itself to provide a pre-evolved patient from memory. If, however, the knowledge base is linked for a dynamic situation, then the patient generator dynamically evolves the patient. In either situation, the evolved health state becomes the target health state at this time. For example, the health state has evolved from mild to moderate arthritis, or from mild obesity to moderate obesity.

The computer implemented process also includes the possibility of treating patients with management health issues that do not generally become totally normal (e.g., long term diabetes, arthritis, and the like), as well as health conditions that may return to completely normal (e.g., broken bone, and the like).

In fact, we have determined that it is particularly likely that patients will revert to normal conditions when the patient experiences an exacerbation health state/condition for the computer based examination system. For example, we have determined that an exacerbation condition can have, for example, mild, moderate and severe states. If the patient has a moderate exacerbation, there is a chance that the patient experienced a mild exacerbation before evolving to the moderate state. There is also a chance that the patient had a severe exacerbation, is now recovering, and may return to the normal state a few minutes later.

In summary, the computer based examination system utilizes three actors, the white board the physician and the patient generator. The examinee initiates the whole process by logging in. The examinee logs into the white board, and the white board accesses various information to determine whether the examinee is valid. If the examinee is valid or verified, the white board looks up the examinee's profile to determine any background specifics on the examinee, such as specific areas needing improvement, past examination results, and the like.

The white board then determines or is provided the exam content, and then contacts the patient generator. The patient generator begins the generation process, selects the disease or subject area, and controls the actual combinations of health states and co-morbid health states via a case structure. The case structure controls both the presenting health state as well as the co-morbid health state. The case structure filters the generation process and makes a predetermination to eliminate predetermined impossible situations, or difficult or unimportant situations that are not to be used in the testing. The case structure indicates that even though a specific health state or parallel health state is in the knowledge base and even potentially legitimate, the case structure will not present that problem. Thus, the case structure simply controls which of the health states will be presented to the examinee, and which of the co-morbid health states, and possibly flare states will also be presented to the examinee simultaneously or sequentially.

The white board then retrieves the patient template including, for example, the patient history, the chief complaint, the assessment test, and the like. From this time on, the examinee performs some action by either requesting data which is controlled by the white board or by causing, directly or indirectly, some action to take place. Once an action is performed, the patient may be evolved to the next health state by the patient evolution process.

Both the request of information and the review and evaluation of the examinee's actions or intervention are generally handled by the white board for convenience, but multiple control mechanisms may also be used. If the white board sees there has been a change in health state for the patient, then the white board would then go to patient evolution process to initiate the evolution, and request the patient generator to provide information regarding the evolved patient.

The patient evolution information may optionally be pre-generated for computational efficiency. That is, even when patients are created dynamically, some predetermined evolution information may be ready for use by the computer based examination system based on the potential of the possible evolution periods/health states. For example, if the target health state was moderate, the computer based examination system may have predetermined onset time of moderate, and therefore, know the time for mild, normal, severe, and the like. In effect, the white board database/object optionally includes a complete possible look at the future appearance, as well as the past characteristics for this particular patient at a particular health state.

The underlying goal of the computer based examination system is that the evolutionary process is generally the same as the patient generation process. Both processes are generally the same, just the generation process has more steps to generate the patient. In the evolutionary situation, the computer based examination system deals with multiple possible health state successors in different parallel networks. The zero state, or state where the examination begins, generally has a primary health state like moderate arthritis, possibly a flare state such as an acute swelling in the knee, and comorbid states such as overweight.

To generate the patient history, the computer process take the moderate arthritis, the flared up knee, and the overweight condition and looks backwards in time to determine the most recent precursor state. For example, the precursor of the moderate arthritis could be mild, the precursors of the flare could be baseline or normal, and the precursor for the overweight condition could be normal weight. The computer process sets the patient's current age, for example, as age 50, and now moves backward in time.

For example, for a 50 year old person with moderate arthritis, it is likely that the arthritis began 5-10 years ago. With respect to the flared knee, it is likely that this condition began within the last couple of days. For the overweight condition, it is likely that the 50 year old person began this condition 10-15 years ago. Therefore, there is a 5-10 year interval (arthritis), a 3 day interval (flared knee), and a 10-15 year interval (overweight).

The computer process moves backward in time to that last change that should have occurred. In this situation, the first precursor health state is the flared knee which occurred 3 days ago. The clock then gets reset, and the next earliest precursor health state is determined. The whiteboard generally throws away all the previous information that was used to generate the later precursor health state, and recalculates the next earliest precursor health state until all precursor health states are generated to the normal condition for all conditions/diseases.

Switching to the forward version, the patient evolution process, the computer process looks forward in time instead of backwards in time. Therefore, considering the above example, there may be a change in 3 days (knee flare), another change in 5-10 years (arthritis), and another change in 10-15 years (overweight). The next change that will occur will be in 3 days. That is the evolutionary process which, similar to the patient history generation process, recalculates onset times for each subsequent health state. Thus, the main difference between the history generation process and the patient evolution process is the data being applied to each process.

The computer based examination system may also be used to determine whether specific physicians are practicing cost effective medicine for use by, for example, insurance companies. The system can provide objective criteria for treating patients by defining episodes of care for isolated problems. For, example, the computer system can indicate approximately the amount of money to spend on a patient with a heart attack with no other concurrent problems, for an asthmatic patient per year, and the like.

The computer based examination system and process provides a "flight simulator" where the physician can practice specific preferred forms of treatment, as appropriate. For example, if the patient has a heart attack, the examinee/physician should generally prescribe aspirin for long term usage, but many do not. Thus, the computer based examination system may also be used as a training system so that the examinees rehearse a desirable behavior such as prescribing aspirin after heart attacks. The computer based examination system can therefore also be used to increase desirable behavior when the physician interacts with a real patient.

Consequently, if a particular physician or group of physicians are determined to be expensive for an insurance company or health care group, and the computer based system shows that the physicians are likely to provide appropriate care, then it is possible that this physician or group of physicians have a particularly expensive patient population, and should therefore not be faulted. Further, the computer based examination system may also be adapted to receive the specific data collected by the physician and interventions associated therewith, to further verify that the practice is delivering the appropriate services. Thus, the computer based examination system, may be used to determine whether a particular practice is delivering services within predetermined guidelines.

Figure 15:
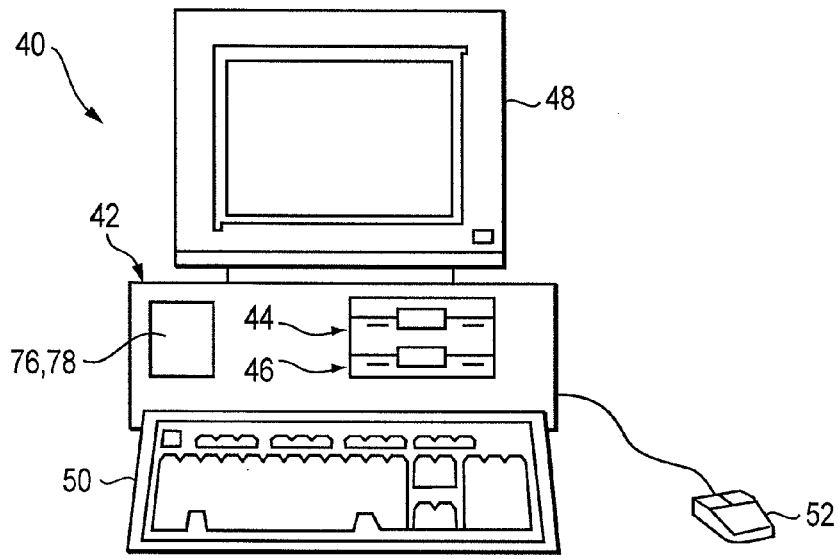
FIG. 15 is an illustration of a main central processing unit for implementing the computer processing in accordance with a computer implemented embodiment of the present invention.

FIG. 15 is an illustration of a main central processing unit for implementing the computer processing in accordance with a computer implemented embodiment of the present invention. The procedures described above may be presented in terms of program procedures executed on, for example, a computer or network of computers.

Viewed externally in FIG. 15, a computer system designated by reference numeral 40 has a central processing unit 42 having disk drives 44 and 46. Disk drive indications 44 and 46 are merely symbolic of a number of disk drives which might be accommodated by the computer system. Typically these would include a floppy disk drive such as 44, a hard disk drive (not shown externally) and a CD ROM indicated by slot 46. The number and type of drives varies, typically with different computer configurations. Disk drives 44 and 46 are in fact optional, and for space considerations, may easily be omitted from the computer system used in conjunction with the process/apparatus described herein.

The computer also has an optional display 48 upon which information is displayed. In some situations, a keyboard 50 and a mouse 52 may be provided as input devices to interface with the central processing unit 42. Then again, for enhanced portability, the keyboard 50 may be either a limited function keyboard or omitted in its entirety. In addition, mouse 52 may be a touch pad control device, or a track ball device, or even omitted in its entirety as well. In addition, the computer system also optionally includes at least one infrared transmitter 76 and/or infrared receiver 78 for either transmitting and/or receiving infrared signals, as described below.

Figure 16:
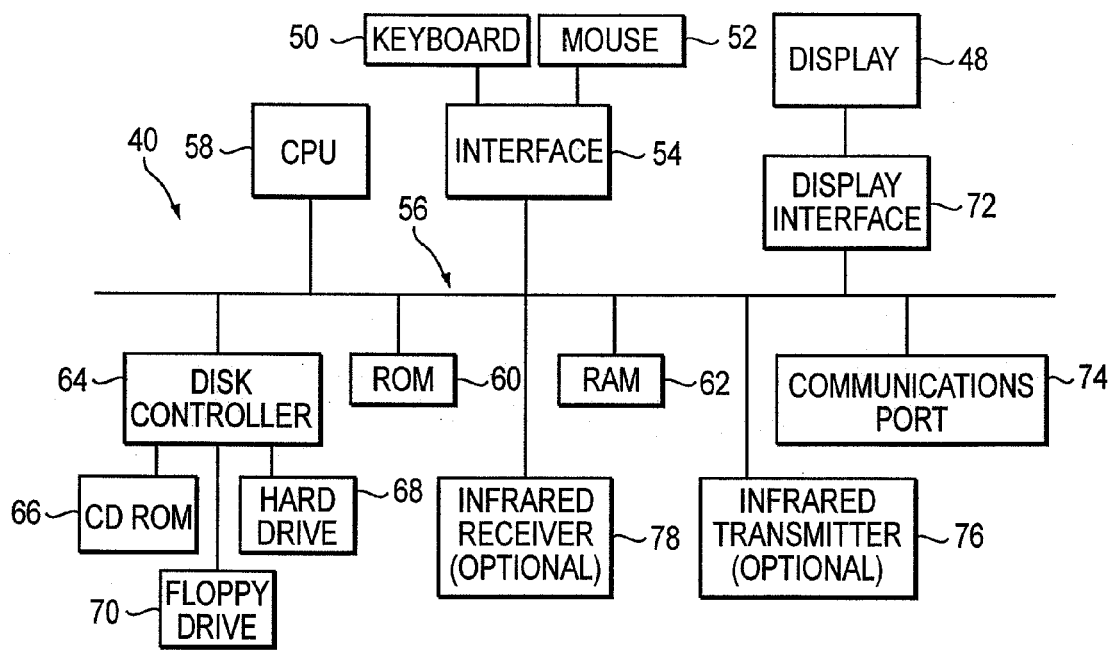
FIG. 16 illustrates a block diagram of the internal hardware of the computer of FIG. 15.

FIG. 16 illustrates a block diagram of the internal hardware of the computer of FIG. 15. A bus 56 serves as the main information highway interconnecting the other components of the computer. CPU 58 is the central processing unit of the system, performing calculations and logic operations required to execute a program. Read only memory (ROM) 60 and random access memory (RAM) 62 constitute the main memory of the computer. Disk controller 64 interfaces one or more disk drives to the system bus 56. These disk drives may be floppy disk drives such as 70, or CD ROM or DVD (digital video disks) drive such as 66, or internal or external hard drives 68. As indicated previously, these various disk drives and disk controllers are optional devices.

A display interface 72 interfaces display 48 and permits information from the bus 56 to be displayed on the display 48. Again as indicated, display 48 is also an optional accessory. For example, display 48 could be substituted or omitted. Communication with external devices, for example, the components of the apparatus described herein, occurs utilizing communication port 74. For example, optical fibers and/or electrical cables and/or conductors and/or optical communication (e.g., infrared, and the like) and/or wireless communication (e.g., radio frequency (RF), and the like) can be used as the transport medium between the external devices and communication port 74.

In addition to the standard components of the computer, the computer also optionally includes at least one of infrared transmitter 76 or infrared receiver 78. Infrared transmitter 76 is utilized when the computer system is used in conjunction with one or more of the processing components/stations that transmits/receives data via infrared signal transmission.

Figure 17:
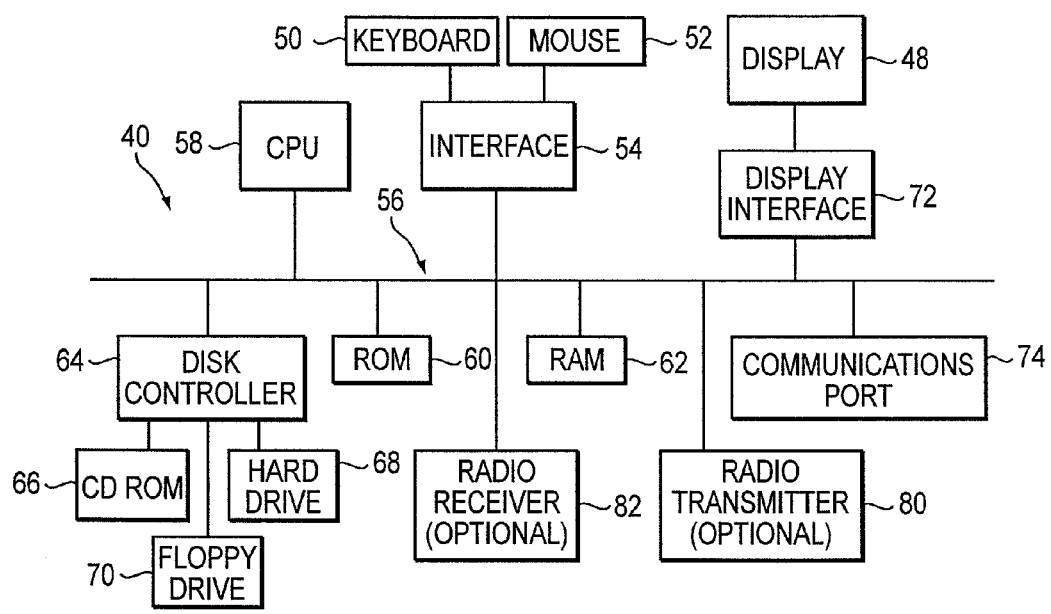
FIG. 17 is a block diagram of the internal hardware of the computer of FIG. 16 in accordance with a second embodiment.

FIG. 17 is a block diagram of the internal hardware of the computer of FIG. 15 in accordance with a second embodiment. In FIG. 17, instead of utilizing an infrared transmitter or infrared receiver, the computer system uses at least one of a low power radio transmitter 80 and/or a low power radio receiver 82. The low power radio transmitter 80 transmits the signal for reception by components of the process, and receives signals from the components via the low power radio receiver 82. The low power radio transmitter and/or receiver 80, 82 are standard devices in industry.

Figure 18:
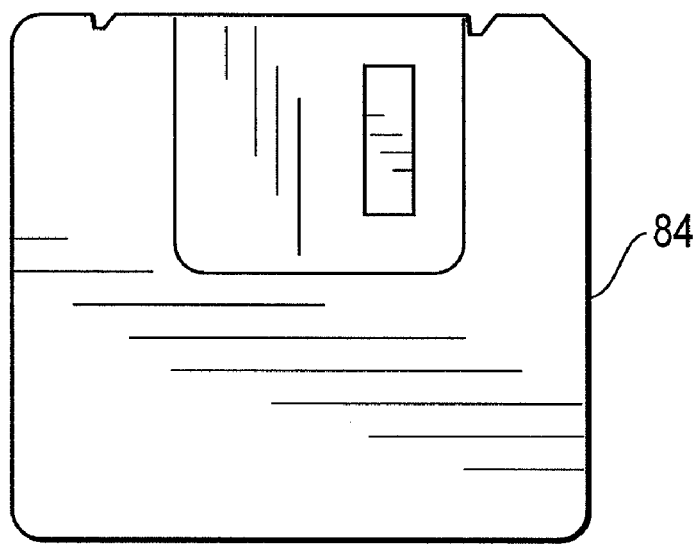
FIG. 18 is an illustration of an exemplary memory medium which can be used with disk drives illustrated in FIGS. 15-17.

FIG. 18 is an illustration of an exemplary memory medium which can be used with disk drives illustrated in FIGS. 15-17. Typically, memory media such as floppy disks, or a CD ROM, or a digital video disk will contain, for example, a multi-byte locale for a single byte language and the program information for controlling the computer to enable the computer to perform the functions described herein. Alternatively, ROM 60 and/or RAM 62 illustrated in FIGS. 16-17 can also be used to store the program information that is used to instruct the central processing unit 58 to perform the operations associated with the process.

Although processing system 40 is illustrated having a single processor, a single hard disk drive and a single local memory, processing system 40 may suitably be equipped with any multitude or combination of processors or storage devices. Processing system 40 may, in point of fact, be replaced by, or combined with, any suitable processing system operative in accordance with the principles of the present invention, including sophisticated calculators, and hand-held, laptop/notebook, mini, mainframe and super computers, as well as processing system network combinations of the same.

Conventional processing system architecture is more fully discussed in *Computer Organization and Architecture*, by William Stallings, MacMillam Publishing Co. (3rd ed. 1993); conventional processing system network design is more fully discussed in *Data Network Design*, by Darren L. Spohn, McGraw-Hill, Inc. (1993), and conventional data communications is more fully discussed in *Data Communications Principles*, by R. D. Gitlin, J. F. Hayes and S. B. Weinstain, Plenum Press (1992) and in *The Irwin Handbook of Telecommunications*, by James Harry Green, Irwin Professional Publishing (2nd ed. 1992). Each of the foregoing publications is incorporated herein by reference.

Alternatively, the hardware configuration may be arranged according to the multiple instruction multiple data (MIMD) multiprocessor format for additional computing efficiency. The details of this form of computer architecture are disclosed in greater detail in, for example, U.S. Pat. No. 5,163, 131; Boxer, A., Where Buses Cannot Go, IEEE Spectrum, February 1995, pp. 41-45; and Barroso, L. A. et al., RPM: A Rapid Prototyping Engine for Multiprocessor Systems, IEEE. Computer February 1995, pp. 26-34, all of which are incorporated herein by reference.

In alternate preferred embodiments, the above-identified processor, and in particular microprocessing circuit 58, may be replaced by or combined with any other suitable processing circuits, including programmable logic devices, such as PALs (programmable array logic) and PLAs (programmable logic arrays). DSPs (digital signal processors), FPGAs (field programmable gate arrays), ASICs (application specific integrated circuits), VLSIs (very large scale integrated circuits) or the like.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

For example, while the above discussion has separated the various functions into separate functionality, the functions may be combined, physically and/or logically, and various functions may be combined together. While combining various functions may make implementation details more cumbersome, nevertheless, the functions described herein may still be accomplished to advantageously provide some or all of the benefits of the invention described herein.

As an additional example, the foregoing discussion focused exclusively on medical applications of the current invention. Advantageously, the invention applies equally well to creating simulations of other complex systems, particularly complex systems in which an empiric description is easier to obtain than a comprehensive mathematical description. The concepts in the invention correspond to generic concepts that apply to complex systems in general. The labels in the current invention and the generic concept are listed in the table below.

The Population (or Person or Simulated Patient) concept represents any complex system. Consider a nuclear power plant. All breeder reactors form a population of breeder reactors, and each individual breeder reactor is an independent complex system within that population. The Record concept again reflects the knowledge of the system held by either people or computers. The breeder reactor may have its own Record of itself stored in a computer that supervises its operations. The public media and the Department of Energy will maintain other Records regarding the plant. Any of these records may contain inaccuracies.

The Health State concept corresponds to a generic System State. As with Health States, the System States often apply to specific parts of the plant. The Body Site concept corresponds to a generic Physical Component, such as the plant (like the body), the core (like the heart), and pipes (like the throat, blood vessels, or urethra). Each System State will apply to some of these components. For instance, it may be reasonable to describe the integrity of any pipe by naming its System State from a group of Pipe leak states. Obviously, one pipe may be leaking or ruptured while another pipe is intact, exactly as we have found with Health States occurring at Body Parts. A System State might include an error in a supervising computer's code, leading the complex system to respond inappropriately in some situation. This roughly corresponds to mental illness manifested by maladaptive behavior.

The Lead to relation again connects System States into parallel networks. Lead to relations again contain Modifiers which describe events that make transitions between System States more or less rapid. For instance, an earthquake might cause a fatigued pipe to twist, leak, and finally rupture, just as a sports injury can cause an ankle tendon to stretch, tear, and finally rupture.

Findings again represent observable facts about the Complex System, such as the temperature of a reactor's core, the water level of the core, or the flow rate of water through a pipe. System States will be defined primarily by the Specific Findings present. The exact Findings required will be provided by a generation method, such as a Bayesian network that reproduces experts logic about the clusters of Findings required to classify a Physical Component of a Complex System as existing in a particular System State. The simulation program asserts that the System State required for the simulation is present, then solves for all unknown nodes in this Bayesian network.

Courses of action again represent activities by humans, another external system, or the system itself. Generally, these will be efforts to restore or maintain equilibrium of the system, or to intentionally prepare the systems for a change of State. For instance, preparing the breeder reactor for a scheduled shutdown and maintenance is a course of action similar to preparing a patient for surgery. Agents again represent inputs to the system that influence its Findings or progression, such as cooling rods, water, fuel, or repairs to computer code.

Thus, we believe that the current invention has broad applicability beyond the domain of medical simulations. It is especially likely to be useful when the behavior of a system is so complex that an understanding of the system defies mathematical description. For instance, this invention is not well suited to simulating the flight of an airplane, which is fully described by physical laws. However, it might be excellent for simulating maintenance of the airplane, which is likely to reflect obscure design decisions and even unknown, but empirically observed, interactions between design decisions.

| Label in this invention | Generic concept | Nuclear power plant example |
| --- | --- | --- |
| Population Record | Complex system Record | Nuclear power plant Press releases, DOE documentation |
| Health State | System State | Overheated core, Leaking pipe |
| Body site | Physical comp. | Plant, Core, Pipe |
| Lead To | Lead to | Intact pipe leads to Leaking pipe |
| Modifier | Modifier | Bayesian network describing how age and Earthquake modify the pipe lead to |
| Finding | Finding | Core temperature, Water level |
| Gener. method | Generation method | Bayesian network describing an intact nuclear plant |
| Course of Act. | Course of Action | Manual shutdown, automated shutdown |
| Agent | Agent | Carbon rod, Water, Uranium, Earthquake |

Further, as indicated herein, the present invention may be applied across a broad range of programming languages that utilize similar concepts as described herein. The present invention may also be used in a distributed environment/architecture, optionally using thin client technology.

What is claimed is:

1. A computer system for training a user to treat a simulated patient having at least one present health state, comprising:
    (a) a computer generating the simulated patient and a history for the simulated patient, wherein said generating comprises evolving the simulated patient backwards in time to generate a progression of health states and risk factors traversed by the simulated patient from a specified health condition to a normal health condition; and
    (b) the computer iterating through a prescribed treatment protocol prescribed by said user, wherein said iterating comprises evolving the simulated patient forward from at least one present health state to at least one subsequent health state responsive to at least one of time and at least one intervention input by the user, and using parallel networks of health states to model transitions that occur among a set of mutually exclusive health conditions in at least one body part comprising at least one of the following interactions: (1) independent interaction between parallel networks so that patient evolution between first and second parallel networks are unrelated to each other; (2) unilateral interaction between the parallel networks so that patient evolution on a first parallel network is unrelated to patient evolution on a second parallel network, and patient evolution on the second parallel network is related to the patient evolution on the first parallel network; and (3) mutually dependent interaction between the parallel networks so that patient evolution between the first and second parallel networks are related to each other.

2. A computer system according to claim 1, further comprising: (c) accessing a profile for said user; (d) selecting a training area to evaluate said user based on at least the user's profile; (e) dynamically generating multiple instances of patients responsive to said training area.

3. A computer system according to claim 1, further comprising: (c) evolving the patient to the at least one subsequent health state responsive to the at least one intervention; and (d) evaluating the user responsive to the at least one intervention input by the user.

4. A computer system according to claim 1, further comprising: (c) evolving the patient to the at least one subsequent health state responsive to the at least one intervention and the patient history; and (d) evaluating the user responsive to at least one of the at least one intervention input by the user, and the at least one subsequent health state.

5. A computer system according to claim 1, further comprising: (c) evolving the patient to the at least one subsequent health state responsive to the at least one intervention and the patient history; (d) receiving at least one other intervention input by the user; (e) evolving the patient responsive to the at least one other intervention from the at least one subsequent health state to at least one other subsequent health state; and (I) evaluating the user responsive to at least one of the at least one other intervention, the at least one subsequent health state, and the at least one other subsequent health state.

6. A computer system according to claim 1, wherein the method uses an entity relationship model.

7. A computer system according to claim 6, wherein the entity relationship model comprises population, record, agents of change, health states, findings and courses of action.

8. A computer system according to claim 7, wherein the findings include specific findings, patterns and sub-patterns describing patient behaviors and characteristics.

9. A computer system according to claim 8, wherein the patterns describe one or more features over time.

10. A computer system according to claim 8, wherein the sub-patterns describe consequences of patient related events.

11. A computer system according to claim 8, wherein the patterns model time and characterize interrelated medical observations.

12. A computer system according to claim 8, further comprising performing a differential diagnosis responsive to the findings, the patterns and the sub-patterns.

13. A computer system according to claim 8, wherein confidence in a presence of the patterns increases with passage of time.

14. A computer system according to claim 7, wherein the courses of action describe tasks and methods used to apply, modify, and evaluate health state information and characteristics described in the entity relationship model.

15. A computer system according to claim 7, wherein the courses of action describe patient activities, including at least one of medical and non-medical activities.

16. A computer system according to claim 7, wherein the courses of action describe potential interventions input by the user including at least one of diagnostic and management strategies.

17. A computer system according to claim 7, wherein the courses of action comprise one or more elementary courses of action used to construct at least one course of action, one or more types of elementary courses of action corresponding to the one or more elementary courses of action, and weighting factors corresponding to the one or more elementary courses of action.

18. A computer system according to claim 6, further comprising evolving the patient responsive to the at least one intervention, entity relations and the patient history to at least one subsequent health state.

19. A computer system according to claim 6, wherein the at least one intervention by the user is considered by the entity relationship model in evolving the patient from a first health state to a subsequent health state.

20. A computer system according to claim 6, wherein the entity relationship model includes one or more of the following relations between entities:
Population Contacts Population
Population Related to Population
Population Interacts with Courses of Action
Population Exposed to Agents of Change
Population Has Health States
Population Exhibits Findings
Agents of Change Cause Health States
Health States Lead to Health States
Findings Associated with Health States
Findings Link to Findings
Course of Action use Agents of Change
Courses of Action Identify Agents of Change
Courses of Action Treat Health States
Courses of Action Alter Findings
Courses of Action Reveal Findings
Courses of Action Evaluate Findings.

21. A computer system according to claim 8, wherein the entity relationship model links the findings with the patterns to a health state, rather than linking a range of finding values to the health state.

22. A computer system according to claim 8, wherein the patterns include sensitivity and specificity represented as age dependent, rather than as constants.

23. A computer system according to claim 1, wherein said generating the patient history is executed once for each simulation to generate the patient history used in said computer implemented simulation and evaluation method.

24. A computer system according to claim 3, further compromising repeating said evolving, and said evaluating a plurality of times.

25. A computer system according to claim 1, further comprising generating the patient history using a Monte Carlo process to generate a plurality of potential patient histories.

26. A computer system according to claim 6, wherein the entity relationship model utilizes tree structures to describe a probability density function conditioned on comorbidities, treatments, risk factors, and the interventions.

27. A computer system according to claim 6, wherein the entity relationship model includes diagnostic complexities and disease interactions.

28. A computer system according to claim 1, wherein at least one of the parallel networks comprises a single health state.

29. A computer system according to claim 1, wherein the parallel networks of health states describe at least one of a chronic condition and non-chronic condition.

30. A computer system according to claim 29, wherein the non-chronic condition includes acute exacerbations describing acute flares of illness that occur during a more chronic health condition.

31. A computer system according to claim 1, wherein at least one of the parallel networks comprises at least one health state.

32. A computer system according to claim 3, further comprising repeating said evolving responsive to: (1) parallel health states of the patient; and (2) a target health state and health state combinations that lead to different parallel states.

33. A computer system according to claim 1, wherein the parallel networks of health states comprise: (1) a primary network including primary health conditions defining a health domain; (2) a risk factor network including risk factors for progression through the primary network; and (3) complications attributed to treating the primary health conditions in the primary network.

34. A computer system according to claim 33, wherein the parallel networks of health states are generated using the following information: (1) how long at least one of the risk factors exists before influencing a transition between primary health conditions in the primary network; (2) time required for transitions in the primary network, considering different combinations of the risk factors; and (3) number of transitions the patient is allowed to make between a specified health state and a normal health state.

35. A computer system according to claim 6, wherein the entity relationship model is based on knowledge data, further comprising acquiring the knowledge data by at least one of questioning domain experts, access to scientific literature, and protocol analysis.

36. A computer system according to claim 6, wherein patterns, having a shape and reflecting probability distributions, describe at least one entity or relationship, and wherein said evolving is responsive to at least one of the patterns.

37. A computer system according to claim 36, wherein the patterns have at least one of cycles, sub-patterns and sub-sub-patterns, and wherein said evolving is responsive to at least one of the cycles, sub-patterns and sub-sub-patterns.

38. A computer system according to claim 7, wherein each health state is part of a network of related and mutually exclusive health states, and a plurality of health state networks exist in parallel, further comprising defining the parallel networks as active or inactive, and defining the active networks as primary or comorbid.

39. A computer system according to claim 38, further comprising adding one or more new states to the network using one or more irreversible interventions.

40. A computer system according to claim 38, further comprising defining an overall health of a patient by a vector indicating the patient's current health state in each network.

41. A computer system according to claim 1, further comprising:
  accessing a profile of the user;
  defining the at least one present health state and the history for the patient responsive to the user profile including prior performance of the user;
  generating the patient and the history for the patient responsive to the at least one present health state and the user profile; and
  iterating through the prescribed treatment protocol with said user for the simulated patient, and evolving the patient from the at least one present health state to at least one subsequent health state responsive to at least one of time and at least one intervention input by the user.

42. A computer system according to claim 41, further comprising generating an initial patient history state in response to the profile of the user who is being evaluated on the basis of the at least one intervention input by the user.

43. A computer system according to claim 1, wherein said generating the history further comprises generating the history by determining at least one precursor health state for the at least one present health state and one or more risk factors.

44. A computer system according to claim 43, wherein said determining the at least one precursor health state further comprises determining one or more risk factors.

45. A computer system according to claim 43, further comprising repeating said determining iteratively until a substantially normal health state is reached.

46. A computer system according to claim 1, wherein said generating the history for the patient further comprises establishing for the patient at least one of an age, sex, racial/ethnic origin, and age of onset of the present health state, and wherein said evolving is responsive to the patient history.

47. A computer system according to claim 1, wherein said evolving further comprises creating a list of possible subsequent health states; identifying all courses of action relevant to each of the possible subsequent health states; and selecting an identified course of action closest to the at least one intervention input by the user.

48. A computer system for training a user to treat a simulated patient having at least one present health state, comprising:
  a computer generating the simulated patient and a history for the simulated patient, wherein said generating comprises evolving the simulated patient backwards in time to generate health states traversed by the simulated patient from a specified health condition to a normal health condition; and
  the computer iterating through a prescribed treatment protocol prescribed by said user, wherein said iterating comprises evolving the simulated patient from at least one present health state to at least one subsequent health state using at least one of the responsive to at least one of time and at least one intervention input by the user, and using at least one of the first and second parallel networks to model transitions that occur among a set of mutually exclusive health conditions in at least one body part comprising at least one of the following interactions: (1) independent interaction between parallel networks so that patient evolution between first and second parallel networks are unrelated to each other; (2) unilateral interaction between the parallel networks so that patient evolution on a first parallel network is unrelated to patient evolution on a second parallel network, and patient evolution on the second parallel network is related to the patient evolution on the first parallel network; and (3) mutually dependent interaction between the parallel networks so that patient evolution between the first and second parallel networks are related to each other.

49. A computer system for training a user to treat a simulated patient having at least one present health state, comprising:
  a computer generating the simulated patient and a history for the simulated patient and evolving the simulated patient backwards in time to generate health states traversed by the simulated patient from a specified health condition to a normal health condition using a parallel network model comprising at least one health state, wherein the at least one health state of the simulated patient at a given time is described as part of a different network comprising a plurality of related and mutually exclusive health states and transitions therebetween, and wherein a plurality of networks exist in parallel; and
  the computer iterating through a prescribed treatment protocol prescribed by said user, wherein said iterating comprises evolving the simulated patient from at least one present health state to at least one subsequent health state responsive to at least one of time and at least one intervention input by the user, and using at least one of first and second parallel networks to model transitions that occur among a set of mutually exclusive health conditions in at least one body part comprising at least one of the following interactions: (1) independent interaction between parallel networks so that patient evolution between first and second parallel networks are unrelated to each other; (2) unilateral interaction between the parallel networks so that patient evolution on a first parallel network is unrelated to patient evolution on a second parallel network, and patient evolution on the second parallel network is related to the patient evolution on the first parallel network; and (3) mutually dependent interaction between the parallel networks so that patient evolution between the first and second parallel networks are related to each other.

50. A computer system for training a user to treat a simulated patient having at least one present health state, comprising:

a computer generating the simulated patient and a history for the simulated patient responsive to evolving the simulated patient backwards in time to generate health states traversed by the simulated patient from a specified health condition to a normal health condition using a parallel network model comprising at least one health state; and the computer iterating through a prescribed treatment protocol prescribed by said user, wherein said iterating comprises evolving the simulated patient from at least one present health state to at least one subsequent health state using at least one of first and second parallel networks responsive to at least one of time and at least one intervention input by the user, and using at least one of the first and second parallel networks to model transitions that occur among a set of mutually exclusive health conditions in at least one body part comprising at least one of the following interactions: (1) independent interaction between parallel networks so that patient evolution between first and second parallel networks are unrelated to each other; (2) unilateral interaction between the parallel networks so that patient evolution on a first parallel network is unrelated to patient evolution on a second parallel network, and patient evolution on the second parallel network is related to the patient evolution on the first parallel network; and (3) mutually dependent interaction between the parallel networks so that patient evolution between the first and second parallel networks are related to each other.

51. A computer system according to claim 48, 49, or 50, further comprising: accessing at least one profile for said user; selecting a training area to evaluate said user based on at least the user's profile; dynamically generating multiple instances of patients responsive to said training area.

52. A computer system according to claim 48, 49, or 50, wherein the method uses an entity relationship model.

53. A computer system according to claim 52, wherein patterns model time and characterize interrelated medical observations.

54. A computer system according to claim 52, further comprising evolving the patient responsive to the at least one intervention, entity relations defined by the entity relationship model and the patient history to at least one subsequent health state.

55. A computer system according to claim 53, wherein the entity relationship model links the findings with the patterns to a health state, rather than linking a range of finding values to the health state.

56. A computer system according to claim 48, 49, or 50, wherein said generating the patient history is executed for each simulation to generate the patient history used in said computer implemented simulation and evaluation method.

57. A computer system according to claim 48, 49, or 50, further comprising generating the patient history comprising a progression of health states and risk factors traversed by the patient from a normal health condition to a specified health condition.

58. A computer system according to claim 48, 49, or 50, further comprising generating the patient history backwards in time from a specified health condition to a normal health condition including successive precursor health states and onset times therebetween.

59. A computer system according to claim 48, 49, or 50, wherein the networks of health states are parallel networks used to model transitions that occur among a set of health conditions responsive to the at least one intervention by the user.

60. A computer system according to claim 59, further comprising repeating said evolving responsive to: (1) parallel health states of the patient; and (2) a target health state and health state combinations that lead to different parallel states.

61. A computer system according to claim 59, wherein the parallel networks of health states comprise: (1) a primary network including primary health conditions defining a health domain; (2) a risk factor network including risk factors for progression through the primary network; and (3) complications attributed to treating the primary health conditions in the primary network.

62. A computer system according to claim 52, wherein patterns, having a shape and reflecting probability distributions, describe at least one entity or relationship, and wherein said evolving is responsive to at least one of the patterns.

63. A computer system according to claim 48, 49, or 50, further comprising generating an initial patient history state in response to the profile of the user who is being evaluated on the basis of the at least one intervention input by the user.

64. A computer system according to claim 48, 49, or 50, wherein said generating the history further comprises generating the history by determining at least one precursor health state for the at least one present health state and one or more risk factors.

65. A computer system according to claim 48, 49, or 50, wherein said evolving further comprises creating a list of possible subsequent health states; identifying courses of action relevant to each of the possible subsequent health states; and selecting an identified course of action closest to the at least one intervention input by the user.

* * * * *